US008841422B2

(12) United States Patent
Qiu et al.

(10) Patent No.: US 8,841,422 B2
(45) Date of Patent: Sep. 23, 2014

(54) HUMAN ANDROGEN RECEPTOR ALTERNATIVE SPLICE VARIANTS

(75) Inventors: Yun Qiu, Ellicott City, MD (US); Zhiyong Guo, Timonium, MD (US); Xi Yang, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 13/403,029

(22) Filed: Feb. 23, 2012

(65) Prior Publication Data

US 2012/0156770 A1 Jun. 21, 2012

Related U.S. Application Data

(63) Continuation-in-part of application No. 12/562,031, filed on Sep. 17, 2009, now Pat. No. 8,133,724.

(60) Provisional application No. 61/097,571, filed on Sep. 17, 2008.

(51) Int. Cl.
    *C07K 16/28* (2006.01)
    *C07K 16/30* (2006.01)
    *C12N 15/113* (2010.01)
    *C07K 14/72* (2006.01)

(52) U.S. Cl.
    CPC .......... *C07K 14/721* (2013.01); *C12N 15/1138* (2013.01); *C12N 2310/14* (2013.01)
    USPC ............ 530/388.22; 530/387.3; 530/387.7; 530/388.1; 530/388.15; 530/389.1; 530/350

(58) Field of Classification Search
    None
    See application file for complete search history.

(56) References Cited

U.S. PATENT DOCUMENTS

| 6,821,767 B1 | 11/2004 | French et al. |
| 7,060,463 B2 * | 6/2006 | Towler et al. |
| 2005/0181462 A1 | 8/2005 | Hara et al. |
| 2011/0110926 A1 | 5/2011 | Luo et al. |

FOREIGN PATENT DOCUMENTS

| JP | 2003102333 | 4/2003 |
| WO | WO 9107423 A1 * | 5/1991 |

OTHER PUBLICATIONS

Hu et al., Ligand-independent androgen receptor variants derived from splicing of cryptic exons signify hormone-refractory prostate cancer, Cancer Res. 69(1):16-22, Jan. 1, 2009.*
Zhu, X. et al., Identification of an exon 3 deletion splice variant androgen receptor mRNA in human breast cancer, Int. J. Cancer, 72:574-580, 1997.
Gottlieb, B. et al., The androgen receptor gene mutations database (ARDB): 2004 update, Human Mutation, 23:527-533, 2004.

(Continued)

*Primary Examiner* — Claire Kaufman
(74) *Attorney, Agent, or Firm* — Roylance, Abrams, Berdo & Goodman, L.L.P.

(57) ABSTRACT

The present invention relates to novel androgen receptor splice variants (AR3, AR4, AR4b, AR5 and AR8) and variants and fragments thereof which have a role in the progression of androgen independent prostate cancer. The invention further relates to compositions and methods which can be used to identify and treat prostate cancer based on these novel androgen receptor splice variants, as well as methods for screening agents which modulate the activity and/or expression of the androgen receptor splice variants. Vectors, host cells and recombinant methods for producing the same and transgenic animals are also provided.

4 Claims, 31 Drawing Sheets

(56) References Cited

OTHER PUBLICATIONS

Guo, Z. et al., A novel androgen receptor splice variant is up-regulated during prostate cancer progression and promotes androgen depletion-resistant growth, Cancer Res., 69(6):2305-2313, 2009.
Zhao, XY. et al., Glucocorticoids can promote androgen-independent growth of prostate cancer cells through a mutated androgen receptor, Nat. Med., 6(6):703-706, 2000.
Stratagene Cloning Systems, (1994) (Stratagene:California), p. 139.
Androgen Receptor Gene Mutations Map, Androgen Receptor Gene Mutations Database (http://androgendb.mcgill.ca/map.gif), Jul. 30, 2003, accessed Aug. 9, 2010.
Clontech 96/97 Catalog (Clontech Laboratories:USA), p. 115, 1996.
Dehm, S.M. et al., Splicing of a novel androgen receptor exon generates a constitutively active androgen receptor that mediates prostate cancer therapy resistance, Cancer Res., 68(13):5469-5477, 2008.

* cited by examiner

Figure 3
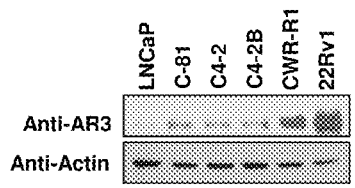
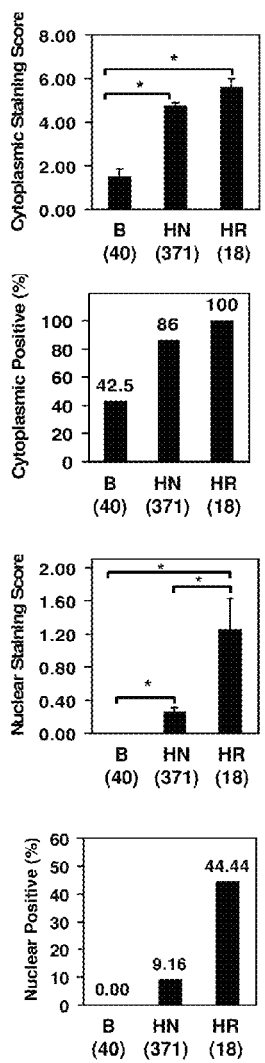
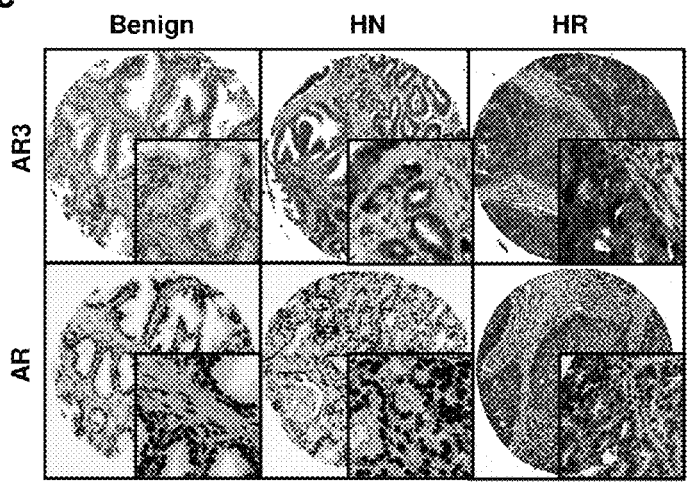
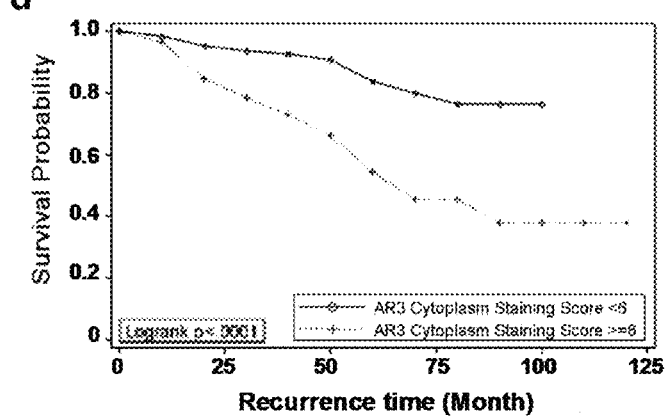

Figure 4
A
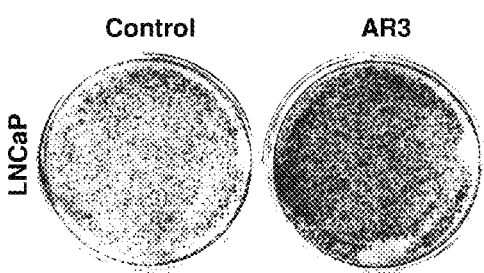
B
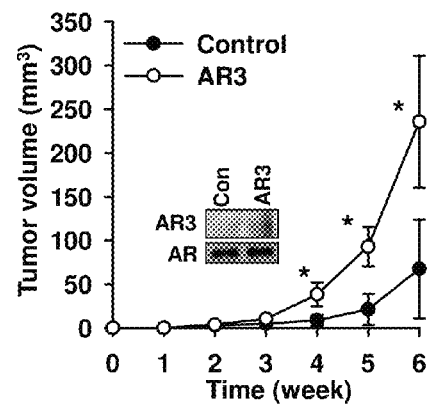
C
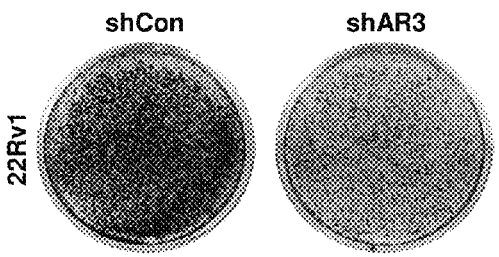
D
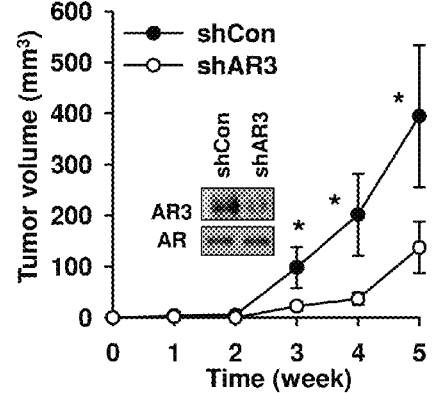
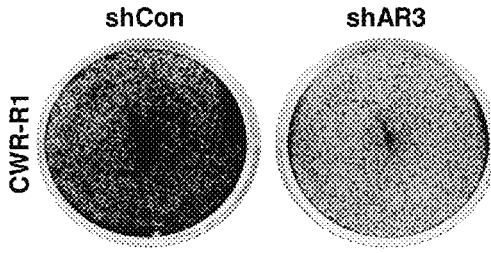
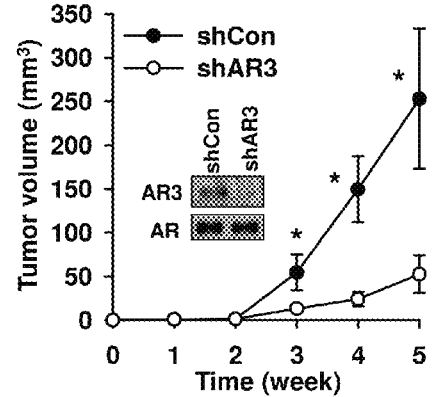

Figure 9
A
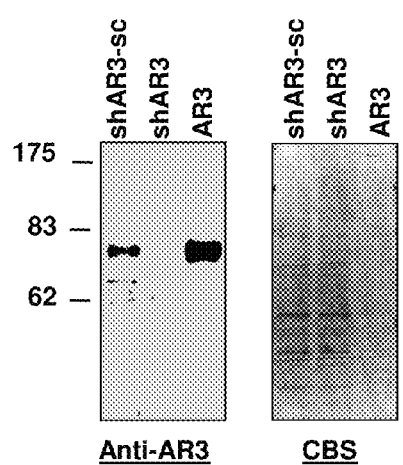
B
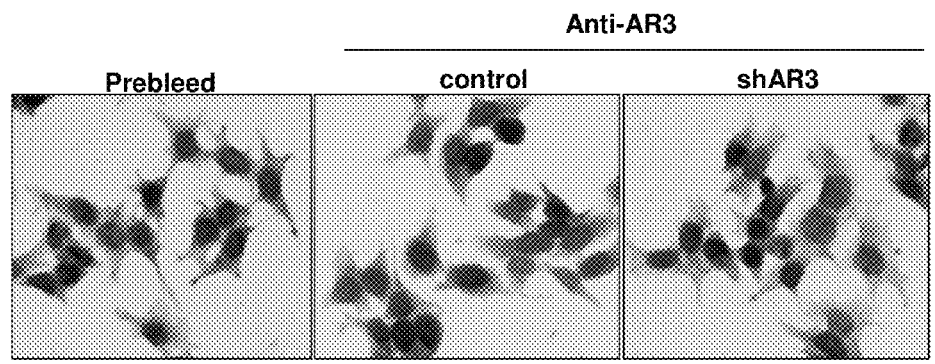

Figure 10
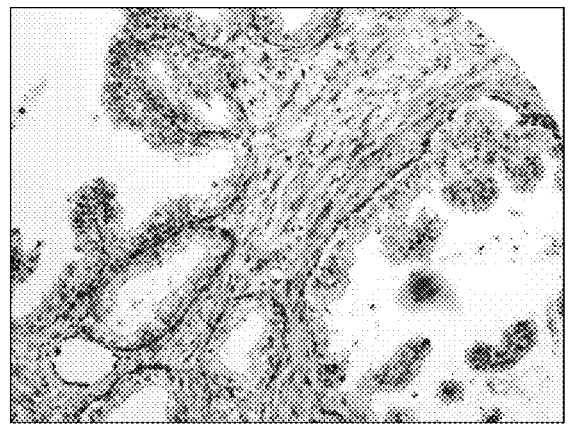
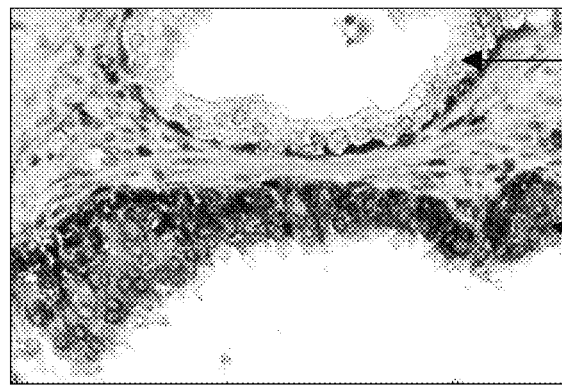

Figure 11A

Human AR3 full-length cDNA sequence

```
GACACTGAATTTGGAAGGTGGAGGATTTTGTTTTTTTCTTTTAAGATCTGGGCATCTTTT
GAATCTACCCTTCAAGTATTAAGAGACAGACTGTGAGCCTAGCAGGGCAGATCTTGTCCA
CCGTGTGTCTTCTTCTGCACGAGACTTTGAGGCTGTCAGAGCGCTTTTTGCGTGGTTGCT
CCCGCAAGTTTCCTTCTCTGGAGCTTCCCGCAGGTGGGCAGCTAGCTGCAGCGACTACCG
CATCATCACAGCCTGTTGAACTCTTCTGAGCAAGAGAAGGGGAGGCGGGGTAAGGGAAGT
AGGTGGAAGATTCAGCCAAGCTCAAGGATGGAAGTGCAGTTAGGGCTGGGAAGGGTCTAC
                                M   E   V   Q   L   G   R   V   Y
CCTCGGCCGCCGTCCAAGACCTACCGAGGAGCTTCCAGAATCTGTTCCAGAGCGTGCGC
  P   R   P   P   S   K   T   Y   R   G   A   F   Q   N   L   F   Q   S   V   R
GAAGTGATCCAGAACCCGGGCCCCAGGCACCCAGAGGCCGCGAGCGCAGCACCTCCCGGC
  E   V   I   Q   N   P   G   P   R   H   P   E   A   A   S   A   A   P   P   G
GCCAGTTTGCTGCTGCAGCAGCAGCAGCAGCAGCAGCAGCAGCAGCAGCAGCAGCAGCAG
  A   S   L   L   Q   Q   Q   Q   Q   Q   Q   Q   Q   Q   Q   Q   Q   Q   Q   Q
CAGCAGCAGCAGCAGCAGCAGCAGCAGCAGCAGCAGCAGCAAGAGACTAGCCCCAGGCAG
  Q   Q   Q   Q   Q   Q   Q   Q   Q   Q   Q   Q   Q   E   T   S   P   R   Q
CAGCAGCAGCAGCAGGGTGAGGATGGTTCTCCCCAAGCCCATCGTAGAGGCCCCACAGGC
  Q   Q   Q   Q   Q   G   E   D   G   S   P   Q   A   H   R   R   G   P   T   G
TACCTGGTCCTGGATGAGGAACAGCAACCTTCACAGCCGCAGTCGGCCCTGGAGTGCCAC
  Y   L   V   L   D   E   E   Q   Q   P   S   Q   P   Q   S   A   L   E   C   H
CCCGAGAGAGGTTGCGTCCCAGAGCCTGGAGCCGCCGTGGCCGCCAGCAAGGGGCTGCCG
  P   E   R   G   C   V   P   E   P   G   A   A   V   A   A   S   K   G   L   P
CAGCAGCTGCCAGCACCTCCGGACGAGGATGACTCAGCTGCCCCATCCACGTTGTCCCTG
  Q   Q   L   P   A   P   P   D   E   D   D   S   A   A   P   S   T   L   S   L
CTGGGCCCCACTTTCCCCGGCTTAAGCAGCTGCTCCGCTGACCTTAAAGACATCCTGAGC
  L   G   P   T   F   P   G   L   S   S   C   S   A   D   L   K   D   I   L   S
GAGGCCAGCACCATGCAACTCCTTCAGCAACAGCAGCAGGAAGCAGTATCCGAAGGCAGC
  E   A   S   T   M   Q   L   L   Q   Q   Q   Q   E   A   V   S   E   G   S
AGCAGCGGGAGAGCGAGGGAGGCCTCGGGGGCTCCCACTTCCTCCAAGGACAATTACTTA
  S   S   G   R   A   R   E   A   S   G   A   P   T   S   S   K   D   N   Y   L
GGGGGCACTTCGACCATTTCTGACAACGCCAAGGAGTTGTGTAAGGCAGTGTCGGTGTCC
  G   G   T   S   T   I   S   D   N   A   K   E   L   C   K   A   V   S   V   S
ATGGGCCTGGGTGTGGAGGCGTTGGAGCATCTGAGTCCAGGGGAACAGCTTCGGGGGGAT
  M   G   L   G   V   E   A   L   E   H   L   S   P   G   E   Q   L   R   G   D
TGCATGTACGCCCCACTTTTGGGAGTTCCACCCGCTGTGCGTCCCACTCCTTGTGCCCCA
  C   M   Y   A   P   L   L   G   V   P   P   A   V   R   P   T   P   C   A   P
TTGGCCGAATGCAAAGGTTCTCTGCTAGACGACAGCGCAGGCAAGAGCACTGAAGATACT
  L   A   E   C   K   G   S   L   L   D   D   S   A   G   K   S   T   E   D   T
GCTGAGTATTCCCCTTTCAAGGGGAGGTTACACCAAAGGGCTAGAAGGCGAGAGCCTAGGC
  A   E   Y   S   P   F   K   G   G   Y   T   K   G   L   E   G   E   S   L   G
TGCTCTGGCAGCGCTGCAGCAGGGAGCTCCGGGACACTTGAACTGCCGTCTACCCTGTCT
  C   S   G   S   A   A   A   G   S   S   G   T   L   E   L   P   S   T   L   S
CTCTACAAGTCCGGAGCACTGGACGAGGCAGCTGCGTACCAGAGTCGCGACTACTACAAC
  L   Y   K   S   G   A   L   D   E   A   A   A   Y   Q   S   R   D   Y   Y   N
TTTCCACTGGCTCTGGCCGGACCGCCGCCCCTCCGCCGCCTCCCCATCCCCACGCTCGC
  F   P   L   A   L   A   G   P   P   P   P   P   P   P   H   P   H   A   R
ATCAAGCTGGAGAACCCGCTGGACTACGGCAGCGCCTGGGCGGCTGCGGCGGCGCAGTGC
  I   K   L   E   N   P   L   D   Y   G   S   A   W   A   A   A   A   Q   C
CGCTATGGGGACCTGGCGAGCCTGCATGGCGCGGGTGCAGCGGGACCCGGTTCTGGGTCA
  R   Y   G   D   L   A   S   L   H   G   A   G   A   A   G   P   G   S   G   S
CCCTCAGCCGCCGCTTCCTCATCCTGGCACACTCTCTTCACAGCCGAAGAAGGCCAGTTG
```

Figure 11B

```
      P   S   A   A   A   S   S   S   W   H   T   L   F   T   A   E   E   G   Q   L
TATGGACCGTGTGGTGGTGGTGGGGGTGGTGGCGGCGGCGGCGGCGGCGGCGGCGGC
      Y   G   P   C   G   G   G   G   G   G   G   G   G   G   G   G   G   G   G   G
GGCGGCGGCGAGGCGGGAGCTGTAGCCCCTACGGCTACACTCGGCCCCCTCAGGGGCTG
      G   G   G   E   A   G   A   V   A   P   Y   G   Y   T   R   P   P   Q   G   L
GCGGGCCAGGAAAGCGACTTCACCGCACCTGATGTGTGGTACCCTGGCGGCATGGTGAGC
      A   G   Q   E   S   D   F   T   A   P   D   V   W   Y   P   G   G   M   V   S
AGAGTGCCCTATCCCAGTCCCACTTGTGTCAAAAGCGAAATGGGCCCCTGGATGGATAGC
      R   V   P   Y   P   S   P   T   C   V   K   S   E   M   G   P   W   M   D   S
TACTCCGGACCTTACGGGGACATGCGTTTGGAGACTGCCAGGGACCATGTTTTGCCCATT
      Y   S   G   P   Y   G   D   M   R   L   E   T   A   R   D   H   V   L   P   I
GACTATTACTTTCCACCCCAGAAGACCTGCCTGATCTGTGGAGATGAAGCTTCTGGGTGT
      D   Y   Y   F   P   P   Q   K   T   C   L   I   C   G   D   E   A   S   G   C
CACTATGGAGCTCTCACATGTGGAAGCTGCAAGGTCTTCTTCAAAAGAGCCGCTGAAGGG
      H   Y   G   A   L   T   C   G   S   C   K   V   F   F   K   R   A   A   E   G
AAACAGAAGTACCTGTGCGCCAGCAGAAATGATTGCACTATTGATAAATTCCGAAGGAAA
      K   Q   K   Y   L   C   A   S   R   N   D   C   T   I   D   K   F   R   R   K
AATTGTCCATCTTGTCGTCTTCGGAAATGTTATGAAGCAGGGATGACTCTGGGAGAAAAA
      N   C   P   S   C   R   L   K   C   Y   E   A   G   M   T   L   G   E   K
TTCCGGGTTGGCAATTGCAAGCATCTCAAAATGACCAGACCCTGAAGAAAGGCTGACTTG
      F   R   V   G   N   C   K   H   L   K   M   T   R   P   -
CCTCATTCAAAATGAGGGCTCTAGAGGGCTCTAGTGGATAGTCTGGAGAAACCTGGCGTC
TGAGGCTTAGGAGCTTAGGTTTTTGCTCCTCAACACAGACTTTGACGTTGGGGTTGGGGG
CTACTCTCTTGATTGCTGACTCCCTCCAGCGGGACCAATAGTGTTTTCCTACCTCACAGG
GATGTTGTGAGGACGGGCTGTAGAAGTAATAGTGGTTACCACTCATGTAGTTGTGAGTAT
CATGATTATTGTTTCCTGTAATGTGGCTTGGCATTGGCAAAGTGCTTTTGATTGTTCTT
GATCACATATGATGGGGCCAGGCACTGACTCAGGCGGATGCAGTGAAGCTCTGGCTCAG
TCGCTTGCTTTTCGTGGTGTGCTGCCAGGAAGAAACTTTGCTGATGGGACTCAAGGTGTC
ACCTTGGACAAGAAGCAACTGTGTCTGTCTGAGGTTCCTGTGGCCATCTTTATTTGTGTA
TTAGGCAATTCGTATTTCCCCCTTAGGTTCTAGCCTTCTGGATCCCAGCCAGTGACCTAG
ATCTTAGCCTCAGGCCCTGTCACTGAGCTGAAGGTAGTAGCTGATCCACAGAAGTTCAGT
AAACAAGGACCAGATTTCTGCTTCTCCAGGAGAAGAAGCCAGCCAACCCCTCTCTTCAAA
CACACTGAGAGACTACAGTCCGACTTTCCCTCTTACATCTAGCCTTACTGTAGCCACACT
CCTTGATTGCTCTCTCACATCACATGCTTCTCTTCATCAGTTGTAAGCCTCTCATTCTTC
TCCCAAGCCAGACTCAAATATTGTATTGATGTCAAAGAAGAATCACTTAGAGTTTGGAAT
ATCTTGTTCTCTCTGCTCCATAGCTTCCATATTGACACCAGTTTCTTTCTAGTGGAGA
AGTGGAGTCTGTGAAGCCAGGGAAACACACATGTGAGAGTCAGAAGGACTCTCCCTGACT
TGCCTGGGGCCTGTCTTTCCCACCTTCTCCAGTCTGTCTAAACACACACACACACACACA
CACACACACACACACACACACACGCTCTCTCTCTCTCCCCCCCAACACACACACA
CTCTCTCTCACACACACACACATACACACACTTCTTTCTTTCCCCTGACTCAGC
AACATTCTGGAGAAAAGCCAAGGAAGGACTTCAGGAGGGGAGTTTCCCCCTTCTCAGGGC
AGAATTTTAATCTCCAGACCAACAAGAAGTTCCCTAATGTGGATTGAAAGGCTAATGAGG
TTTATTTTTAACTACTTTCTATTTGTTTGAATGTTGCATATTTCTACTAGTGAAATTTTC
CCTTAATAAAGCCATTAATACACCCAAAAAAAAAAAAAAAA
```

Figure 12A

Putative human AR4 full-length cDNA sequence

```
GACACTGAATTTGGAAGGTGGAGGATTTTGTTTTTTTCTTTTAAGATCTGGGCATCTTTT
GAATCTACCCTTCAAGTATTAAGAGACAGACTGTGAGCCTAGCAGGGCAGATCTTGTCCA
CCGTGTGTCTTCTTCTGCACGAGACTTTGAGGCTGTCAGAGCGCTTTTTGCGTGGTTGCT
CCCGCAAGTTTCCTTCTCTGGAGCTTCCCGCAGGTGGGCAGCTAGCTGCAGCGACTACCG
CATCATCACAGCCTGTTGAACTCTTCTGAGCAAGAGAAGGGGAGGCGGGTAAGGGAAGT
AGGTGGAAGATTCAGCCAAGCTCAAGGATGGAAGTGCAGTTAGGGCTGGGAAGGGTCTAC
                                  M  E  V  Q  L  G  L  G  R  V  Y
CCTCGGCCGCCGTCCAAGACCTACCGAGGAGCTTTCCAGAATCTGTTCCAGAGCGTGCGC
 P  R  P  P  S  K  T  Y  R  G  A  F  Q  N  L  F  Q  S  V  R
GAAGTGATCCAGAACCCGGGCCCCAGGCACCCAGAGGCCGCGAGCGCAGCACCTCCCGGC
 E  V  I  Q  N  P  G  P  R  H  P  E  A  A  S  A  P  P  G
GCCAGTTTGCTGCTGCAGCAGCAGCAGCAGCAGCAGCAGCAGCAGCAGCAGCAGCAGCAG
 A  S  L  L  Q  Q  Q  Q  Q  Q  Q  Q  Q  Q  Q  Q  Q  Q  Q  Q
CAGCAGCAGCAGCAGCAGCAGCAGCAGCAGCAGCAGCAAGAGACTAGCCCCAGGCAGCAG
 Q  Q  Q  Q  Q  Q  Q  Q  Q  Q  Q  Q  E  T  S  P  R  Q  Q
CAGCAGCAGCAGGGTGAGGATGGTTCTCCCCAAGCCCATCGTAGAGGCCCCACAGGCTAC
 Q  Q  Q  Q  G  E  D  G  S  P  Q  A  H  R  R  G  P  T  G  Y
CTGGTCCTGGATGAGGAACAGCAACCTTCACAGCCGCAGTCGGCCCTGGAGTGCCACCCC
 L  V  L  D  E  E  Q  Q  P  S  Q  P  Q  S  A  L  E  C  H  P
GAGAGAGGTTGCGTCCCAGAGCCTGGAGCCGCCGTGGCCGCCAGCAAGGGGCTGCCGCAG
 E  R  G  C  V  P  E  P  G  A  A  V  A  A  S  K  G  L  P  Q
CAGCTGCCAGCACCTCCGGACGAGGATGACTCAGCTGCCCCATCCACGTTGTCCCTGCTG
 Q  L  P  A  P  P  D  E  D  D  S  A  A  P  S  T  L  S  L  L
GGCCCCACTTTCCCCGGCTTAAGCAGCTGCTCCGCTGACCTTAAAGACATCCTGAGCGAG
 G  P  T  F  P  G  L  S  S  C  S  A  D  L  K  D  I  L  S  E
GCCAGCACCATGCAACTCCTTCAGCAACAGCAGCAGGAAGCAGTATCCGAAGGCAGCAGC
 A  S  T  M  Q  L  L  Q  Q  Q  Q  E  A  V  S  E  G  S  S
AGCGGGAGAGCGAGGGAGGCCTCGGGGGCTCCCACTTCCTCCAAGGACAATTACTTAGGG
 S  G  R  A  R  E  A  S  G  A  P  T  S  S  K  D  N  Y  L  G
GGCACTTCGACCATTTCTGACAACGCCAAGGAGTTGTGTAAGGCAGTGTCGGTGTCCATG
 G  T  S  T  I  S  D  N  A  K  E  L  C  K  A  V  S  V  S  M
GGCCTGGGTGTGGAGGCGTTGGAGCATCTGAGTCCAGGGGAACAGCTTCGGGGGGATTGC
 G  L  G  V  E  A  L  E  H  L  S  P  G  E  Q  L  R  G  D  C
ATGTACGCCCCACTTTTGGGAGTTCCACCCGCTGTGCGTCCCACTCCTTGTGCCCCATTG
 M  Y  A  P  L  L  G  V  P  P  A  V  R  P  T  P  C  A  P  L
GCCGAATGCAAAGGTTCTCTGCTAGACGACAGCGCAGGCAAGAGCACTGAAGATACTGCT
 A  E  C  K  G  S  L  L  D  D  S  A  G  K  S  T  E  D  T  A
GAGTATTCCCCTTTCAAGGGAGGTTACACCAAAGGGCTAGAAGGCGAGAGCCTAGGCTGC
 E  Y  S  P  F  K  G  G  Y  T  K  G  L  E  G  E  S  L  G  C
TCTGGCAGCGCTGCAGCAGGGAGCTCCGGGACACTTGAACTGCCGTCTACCCTGTCTCTC
 S  G  S  A  A  G  S  S  G  T  L  E  L  P  S  T  L  S  L
TACAAGTCCGGAGCACTGGACGAGGCAGCTGCGTACCAGAGTCGCGACTACTACAACTTT
 Y  K  S  G  A  L  D  E  A  A  Y  Q  S  R  D  Y  Y  N  F
CCACTGGCTCTGGCCGGACCGCCGCCCCCTCCGCCGCCTCCCCATCCCCACGCTCGCATC
 P  L  A  L  A  G  P  P  P  P  P  P  P  H  P  H  A  R  I
AAGCTGGAGAACCCGCTGGACTACGGCAGCGCCTGGGCGGCTGCGGCGGCGCAGTGCCGC
 K  L  E  N  P  L  D  Y  G  S  A  W  A  A  A  A  Q  C  R
TATGGGGACCTGGCGAGCCTGCATGGCGCGGGTGCAGCGGGACCCGGTTCTGGGTCACCC
 Y  G  D  L  A  S  L  H  G  A  G  A  A  G  P  G  S  G  S  P
TCAGCCGCCGCTTCCTCATCCTGGCACACTCTCTTCACAGCCGAAGAAGGCCAGTTGTAT
```

Figure 12B

```
             S   A   A   A   S   S   S   W   H   T   L   F   T   A   E   E   G   Q   L   Y
GGACCGTGTGGTGGTGGTGGGGGTGGTGGCGGCGGCGGCGGCGGCGGCGGCGGCGGC
     G   P   C   G   G   G   G   G   G   G   G   G   G   G   G   G   G   G
GGCGGCGAGGCGGGAGCTGTAGCCCCCTACGGCTACACTCGGCCCCCTCAGGGGCTGGCG
     G   G   E   A   G   A   V   A   P   Y   G   Y   T   R   P   P   Q   G   L   A
GGCCAGGAAAGCGACTTCACCGCACCTGATGTGTGGTACCCTGGCGGCATGGTGAGCAGA
     G   Q   E   S   D   F   T   A   P   D   V   W   Y   P   G   G   M   V   S   R
GTGCCCTATCCCAGTCCCACTTGTGTCAAAAGCGAAATGGGCCCCTGGATGGATAGCTAC
     V   P   Y   P   S   P   T   C   V   K   S   E   M   G   P   W   M   D   S   Y
TCCGGACCTTACGGGGACATGCGTTTGGAGACTGCCAGGGACCATGTTTTGCCCATTGAC
     S   G   P   Y   G   D   M   R   L   E   T   A   R   D   H   V   L   P   I   D
TATTACTTTCCACCCCAGAAGACCTGCCTGATCTGTGGAGATGAAGCTTCTGGGTGTCAC
     Y   Y   F   P   P   Q   K   T   C   L   I   C   G   D   E   A   S   G   C   H
TATGGAGCTCTCACATGTGGAAGCTGCAAGGTCTTCTTCAAAAGAGCCGCTGAAGGGAAA
     Y   G   A   L   T   C   G   S   C   K   V   F   F   K   R   A   A   E   G   K
CAGAAGTACCTGTGCGCCAGCAGAAATGATTGCACTATTGATAAATTCCGAAGGAAAAAT
     Q   K   Y   L   C   A   S   R   N   D   C   T   I   D   K   F   R   R   K   N
TGTCCATCTTGTCGTCTTCGGAAATGTTATGAAGCAGGGATGACTCTGGGAGCAGCTGTT
     C   P   S   C   R   L   K   C   Y   E   A   G   M   T   L   G   A   A   V
GTTGTTTCTGAAAGAATCTTGAGGGTGTTTGGAGTCTCAGAATGGCTTCCTTAAAGACTA
     V   V   S   E   R   I   L   R   V   F   G   V   S   E   W   L   P   -
CCTTCAGACTCTCAGCTGCTCATCCACAACAGAGATCAGCCTTTCTTTGTAGATGATTCAT
TCCTGGCTGCATTTGAAAACCACATATTGTTAATTGCTTGACGAATTTAAATCCCTTGACT
ACTTTTCATTTCAGAAAACACTTACAAAAAAAGTCCAAATGAGGACCTTCCCTCCAGTGAA
TTAGCTGTGGCTTTCTCACAGTCCATAGTTAGGATAAATGTAAAGCCATTTCTCATTTTTC
TCCGCACTTTCCAAGGGTACACTCCTTGTTTCCAAGATGGAATGAGAAATAAAGAAGTGCC
CTTCCCCAAACATGATTCATTTCTGCGTTTTGCAACTCTTGAGTTCTCAGCATTTAGTAAA
TGGTGTTGGTCCCTGTTGATTCCTTCCTCCTGGACCATGGAAGGTAGTAGGCCTTTCAG
AAATTTCAGGTAGCAGCCAAACCCCAGAAGAAGAGAAGGAACACAGAGACCTAGACCATGT
GAGAACCTGAGGTGTGCAGCATTTACTTCACAGATTCGTCTAGCATATTTGAGAGGTGTCT
TTCCTACTAGGAGACTGAACTCTGCATCTGAGAATAAAAACTTAACATATCAAAAAAAAAA
AAAAAA
```

Figure 13A

Putative human AR5 full-length cDNA sequence

```
GACACTGAATTTGGAAGGTGGAGGATTTTGTTTTTTTCTTTTAAGATCTGGGCATCTTTT
GAATCTACCCTTCAAGTATTAAGAGACAGACTGTGAGCCTAGCAGGGCAGATCTTGTCCA
CCGTGTGTCTTCTTCTGCACGAGACTTTGAGGCTGTCAGAGCGCTTTTTGCGTGGTTGCT
CCCGCAAGTTTCCTTCTCTGGAGCTTCCCGCAGGTGGGCAGCTAGCTGCAGCGACTACCG
CATCATCACAGCCTGTTGAACTCTTCTGAGCAAGAGAAGGGGAGGCGGGGTAAGGGAAGT
AGGTGGAAGATTCAGCCAAGCTCAAGGATGGAAGTGCAGTTAGGGCTGGGAAGGGTCTAC
                                  M  E  V  Q  L  G  L  G  R  V  Y
CCTCGGCCGCCGTCCAAGACCTACCGAGGAGCTTTCCAGAATCTGTTCCAGAGCGTGCGC
 P  R  P  P  S  K  T  Y  R  G  A  F  Q  N  L  F  Q  S  V  R
GAAGTGATCCAGAACCCGGGCCCCAGGCACCCAGAGGCCGCGAGCGCAGCACCTCCCGGC
 E  V  I  Q  N  P  G  P  R  H  P  E  A  A  S  A  A  P  P  G
GCCAGTTTGCTGCTGCAGCAGCAGCAGCAGCAGCAGCAGCAGCAGCAGCAGCAGCAGCAG
 A  S  L  L  L  Q  Q  Q  Q  Q  Q  Q  Q  Q  Q  Q  Q  Q  Q  Q
CAGCAGCAGCAGCAGCAGCAGCAGCAGCAGCAGCAGCAAGAGACTAGCCCCAGGCAG
 Q  Q  Q  Q  Q  Q  Q  Q  Q  Q  Q  Q  E  T  S  P  R  Q
CAGCAGCAGCAGCAGGGTGAGGATGGTTCTCCCCAAGCCCATCGTAGAGGCCCCACAGGC
 Q  Q  Q  Q  Q  G  E  D  G  S  P  Q  A  H  R  R  G  P  T  G
TACCTGGTCCTGGATGAGGAACAGCAACCTTCACAGCCGCAGTCGGCCCTGGAGTGCCAC
 Y  L  V  L  D  E  E  Q  Q  P  S  Q  P  Q  S  A  L  E  C  H
CCCGAGAGAGGTTGCGTCCCAGAGCCTGGAGCCGCCGTGGCCGCCAGCAAGGGGCTGCCG
 P  E  R  G  C  V  P  E  P  G  A  A  V  A  A  S  K  G  L  P
CAGCAGCTGCCAGCACCTCCGGACGAGGATGACTCAGCTGCCCCATCCACGTTGTCCCTG
 Q  Q  L  P  A  P  P  D  E  D  D  S  A  A  P  S  T  L  S  L
CTGGGCCCCACTTTCCCCGGCTTAAGCAGCTGCTCCGCTGACCTTAAAGACATCCTGAGC
 L  G  P  T  F  P  G  L  S  S  C  S  A  D  L  K  D  I  L  S
GAGGCCAGCACCATGCAACTCCTTCAGCAACAGCAGCAGGAAGCAGTATCCGAAGGCAGC
 E  A  S  T  M  Q  L  L  Q  Q  Q  Q  E  A  V  S  E  G  S
AGCAGCGGGAGAGCGAGGGAGGCCTCGGGGGCTCCCACTTCCTCCAAGGACAATTACTTA
 S  S  G  R  A  R  E  A  S  G  A  P  T  S  S  K  D  N  Y  L
GGGGGCACTTCGACCATTTCTGACAACGCCAAGGAGTTGTGTAAGGCAGTGTCGGTGTCC
 G  G  T  S  T  I  S  D  N  A  K  E  L  C  K  A  V  S  V  S
ATGGGCCTGGGTGTGGAGGCGTTGGAGCATCTGAGTCCAGGGGAACAGCTTCGGGGGGAT
 M  G  L  G  V  E  A  L  E  H  L  S  P  G  E  Q  L  R  G  D
TGCATGTACGCCCCACTTTTGGGAGTTCCACCCGCTGTGCGTCCCACTCCTTGTGCCCCA
 C  M  Y  A  P  L  L  G  V  P  P  A  V  R  P  T  P  C  A  P
TTGGCCGAATGCAAAGGTTCTCTGCTAGACGACAGCGCAGGCAAGAGCACTGAAGATACT
 L  A  E  C  K  G  S  L  L  D  D  S  A  G  K  S  T  E  D  T
GCTGAGTATTCCCCTTTCAAGGGAGGTTACACCAAAGGGCTAGAAGGCGAGAGCCTAGGC
 A  E  Y  S  P  F  K  G  G  Y  T  K  G  L  E  G  E  S  L  G
TGCTCTGGCAGCGCTGCAGCAGGGAGCTCCGGGACACTTGAACTGCCGTCTACCCTGTCT
 C  S  G  S  A  A  A  G  S  S  G  T  L  E  L  P  S  T  L  S
CTCTACAAGTCCGGAGCACTGGACGAGGCAGCTGCGTACCAGAGTCGCGACTACTACAAC
 L  Y  K  S  G  A  L  D  E  A  A  A  Y  Q  S  R  D  Y  Y  N
TTTCCACTGGCTCTGGCCGGACCGCCGCCCCCTCCGCCGCCTCCCCATCCCCACGCTCGC
 F  P  L  A  L  A  G  P  P  P  P  P  P  P  H  P  H  A  R
ATCAAGCTGGAGAACCCGCTGGACTACGGCAGCGCCTGGGCGGCTGCGGCGGCGCAGTGC
 I  K  L  E  N  P  L  D  Y  G  S  A  W  A  A  A  A  Q  C
CGCTATGGGGACCTGGCGAGCCTGCATGGCGCGGGTGCAGCGGGACCCGGTTCTGGGTCA
 R  Y  G  D  L  A  S  L  H  G  A  G  A  A  G  P  G  S  G  S
CCCTCAGCCGCCGCTTCCTCATCCTGGCACACTCTCTTCACAGCCGAAGAAGGCCAGTTG
```

Figure 13B

```
         P   S   A   A   A   S   S   S   W   H   T   L   F   T   A   E   E   G   Q   L
TATGGACCGTGTGGTGGTGGTGGGGGTGGTGGCGGCGGCGGCGGCGGCGGCGGCGGC
     Y   G   P   C   G   G   G   G   G   G   G   G   G   G   G   G   G   G   G
GGCGGCGGCGAGGCGGGAGCTGTAGCCCCCTACGGCTACACTCGGCCCCCTCAGGGGCTG
       G   G   G   E   A   G   A   V   A   P   Y   G   Y   T   R   P   P   Q   G   L
GCGGGCCAGGAAAGCGACTTCACCGCACCTGATGTGTGGTACCCTGGCGGCATGGTGAGC
         A   G   Q   E   S   D   F   T   A   P   D   V   W   Y   P   G   G   M   V   S
AGAGTGCCCTATCCCAGTCCCACTTGTGTCAAAAGCGAAATGGGCCCCTGGATGGATAGC
         R   V   P   Y   P   S   P   T   C   V   K   S   E   M   G   P   W   M   D   S
TACTCCGGACCTTACGGGGACATGCGTTTGGAGACTGCCAGGGACCATGTTTTGCCCATT
         Y   S   G   P   Y   G   D   M   R   L   E   T   A   R   D   H   V   L   P   I
GACTATTACTTTCCACCCCAGAAGACCTGCCTGATCTGTGGAGATGAAGCTTCTGGGTGT
         D   Y   Y   F   P   P   Q   K   T   C   L   I   C   G   D   E   A   S   G   C
CACTATGGAGCTCTCACATGTGGAAGCTGCAAGGTCTTCTTCAAAAGAGCCGCTGAAGGG
           H   Y   G   A   L   T   C   G   S   C   K   V   F   F   K   R   A   A   E   G
AAACAGAAGTACCTGTGCGCCAGCAGAAATGATTGCACTATTGATAAATTCCGAAGGAAA
           K   Q   K   Y   L   C   A   S   R   N   D   C   T   I   D   K   F   R   R   K
AATTGTCCATCTTGTCGTCTTCGGAAATGTTATGAAGCAGGGATGACTCTGGGAGGATTT
         N   C   P   S   C   R   L   R   K   C   Y   E   A   G   M   T   L   G   G   F
TTCAGAATGAACAAATTAAAAGAATCATCAGACACTAACCCCAAGCCATACTGCATGGCA
       F   R   M   N   K   L   K   E   S   S   D   T   N   P   K   P   Y   C   M   A
GCACCAATGGGACTGACAGAAAACAACAGAAATAGGAAGAAATCCTACAGAGAAACAAAC
       A   P   M   G   L   T   E   N   N   R   N   R   K   K   S   Y   R   E   T   N
TTGAAAGCTGTCTCATGGCCTTTGAATCATACTTAAGTTTTATGATGGAAGGATACGACT
       L   K   A   V   S   W   P   L   N   H   T   -
ATGAAGAAAGACACAGAGCAACATCAGACAGTCAAGAATTTCAGAGCCAGCTGGCATGCA
GTGGACCTCATGCCAGCCCATTTTATGACTATTTAGGGAAACAGAAGTACCTGTGCGCCA
GCAGAAATGATTGCACTATTGATAAATTCCGAAGGAAAAATTGTCCATCTTGTCGTCTTC
GGAAATGTTATGAAGCAGGGATGACTCTGGGAGAAAAATTCCGGGTTGGCAATTGCAAGC
ATCTCAAAATGACCAGACCCTGAAGAAAGGCTGACTTGCCTCATTCAAAATGAGGGCTCT
AGAGGGCTCTAGTGGATAGTCTGGAGAAACCTGGCGTCTGAGGCTTAGGAGCTTAGGTTT
TTGCTCCTCAACACAGACTTTGACGTTGGGGTTGGGGGCTACTCTCTTGATTGCTGACTC
CCTCCAGCGGGACCAATAGTGTTTTCCTACCTCACAGGGATGTTGTGAGGACGGGCTGTA
GAAGTAATAGTGGTTACCACTCATGTAGTTGTGAGTATCATGATTATTGTTTCCTGTAAT
GTGGCTTGGCATTGGCAAAGTGCTTTTGATTGTTCTTGATCACATATGATGGGGGCCAG
GCACTGACTCAGGCGGATGCAGTGAAGCTCTGGCTCAGTCGCTTGCTTTTCGTGGTGTGC
TGCCAGGAAGAAACTTTGCTGATGGGACTCAAGGTGTCACCTTGGACAAGAAGCAACTGT
GTCTGTCTGAGGTTCCTGTGGCCATCTTTATTTGTGTATTAGGCAATTCGTATTTCCCCC
TTAGGTTCTAGCCTTCTGGATCCCAGCCAGTGACCTAGATCTTAGCCTCAGGCCCTGTCA
CTGAGCTGAAGGTAGTAGCTGATCCACAGAAGTTCAGTAAACAAGGACCAGATTTCTGCT
TCTCCAGGAGAAGAAGCCAGCCAACCCCTCTCTTCAAACACACTGAGAGACTACAGTCCG
ACTTTCCCTCTTACATCTAGCCTTACTGTAGCCACACTCCTTGATTGCTCTCTCACATCA
CATGCTTCTCTTCATCAGTTGTAAGCCTCTCATTCTTCTCCCAAGCCAGACTCAAATATT
GTATTGATGTCAAAGAAGAATCACTTAGAGTTTGGAATATCTTGTTCTCTCTGCTCCA
TAGCTTCCATATTGACACCAGTTTCTTTCTAGTGGAGAAGTGGAGTCTGTGAAGCCAGGG
AAACACACATGTGAGAGTCAGAAGGACTCTCCCTGACTTGCCTGGGGCCTGTCTTTCCCA
CCTTCTCCAGTCTGTCTAAACACACACACACACACACACACACACACACACACACACACA
CACGCTCTCTCTCTCTCCCCCCCAACACACACACACTCTCTCTCACACACACACA
CATACACACACACTTCTTTCTCTTTCCCCTGACTCAGCAACATTCTGGAGAAAAGCCAAG
GAAGGACTTCAGGAGGGGAGTTTCCCCCTTCTCAGGGCAGAATTTTAATCTCCAGACCAA
CAAGAAGTTCCCTAATGTGGATTGAAAGGCTAATGAGGTTTATTTTTAACTACTTTCTAT
```

Figure 13C

TTGTTTGAATGTTGCATATTTCTACTAGTGAAATTTTCCCTT<u>AATAAA</u>GCCATTAATACA
CCCAAAAAAAAAAAAAAAA

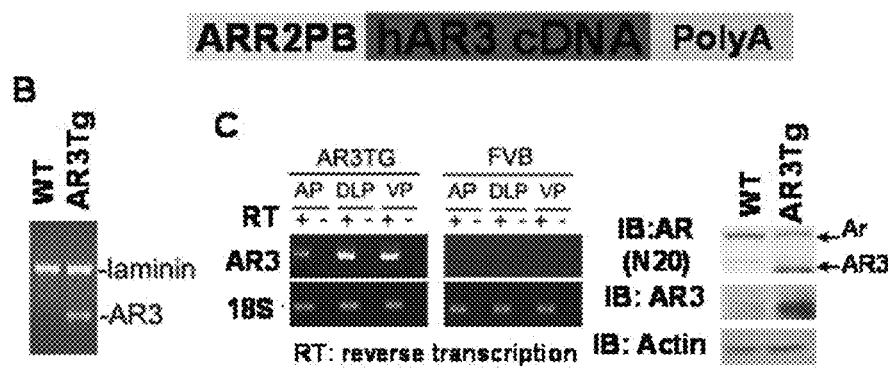
Fig 14 A. Schematic Diagram of ARR2PB-hAR3
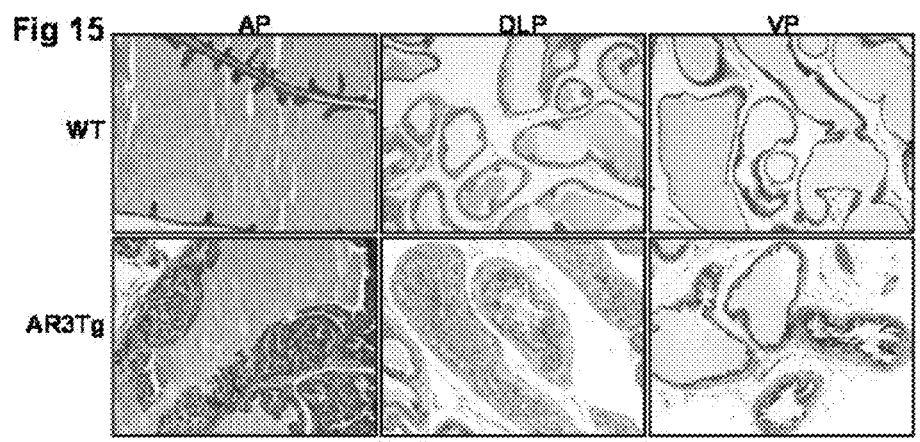

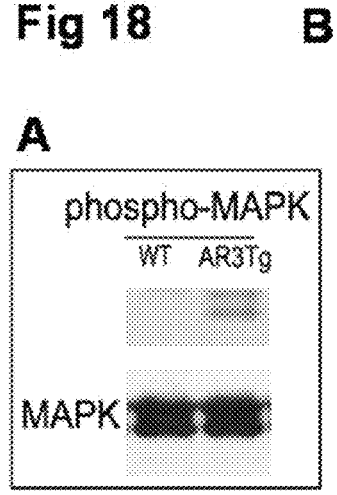
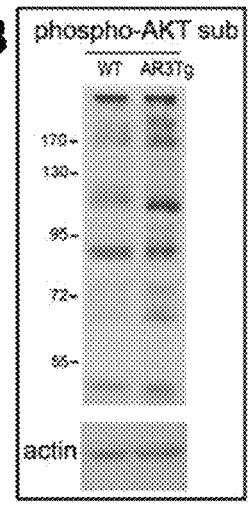
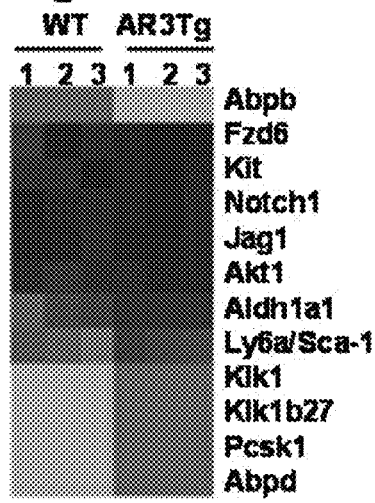
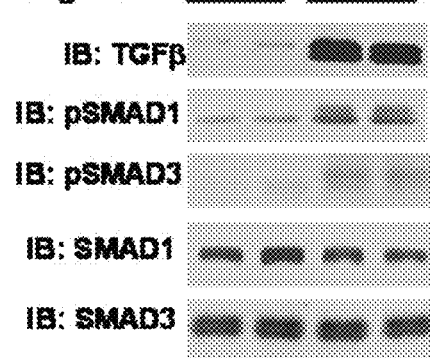

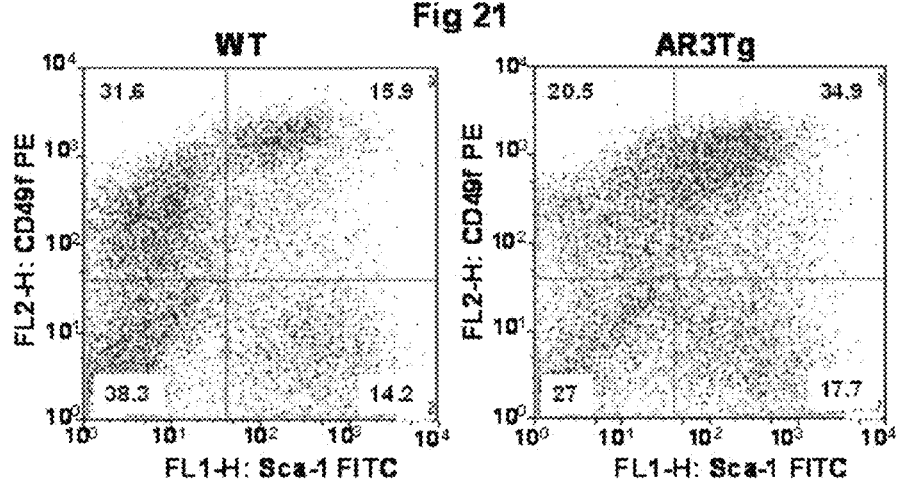
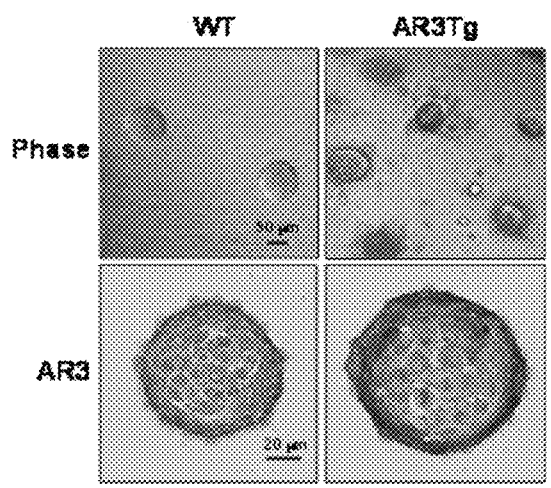

Fig 24
A
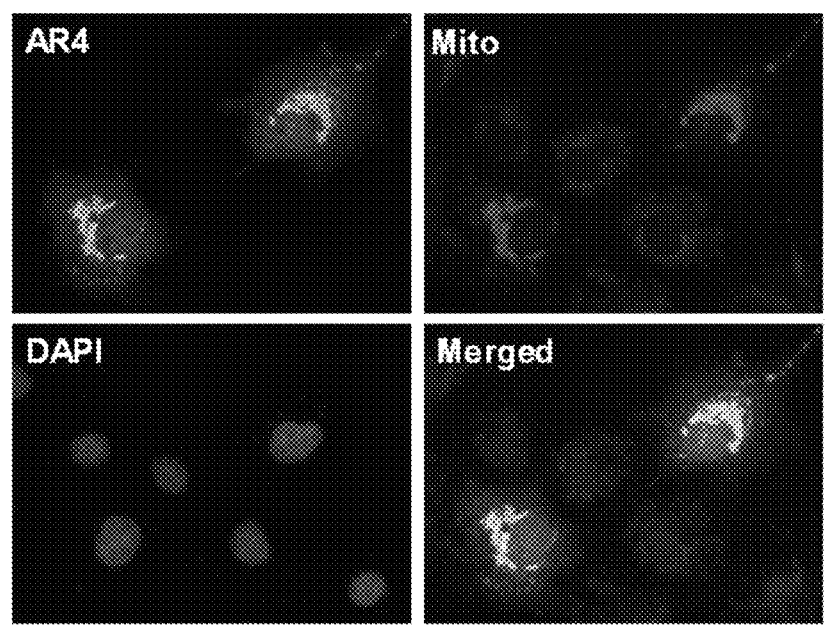
B
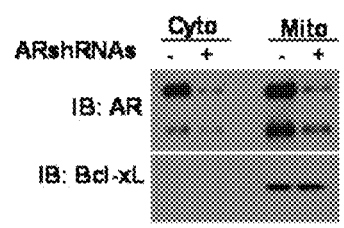

Human AR8 nucleotide sequence
```
gacactgaat ttggaaggtg gaggattttg ttttttctt ttaagatctg ggcatctttt
gaatctaccc ttcaagtatt aagagacaga ctgtgagcct agcagggcag atcttgtcca
ccgtgtgtct tcttctgcac gagactttga ggctgtcaga gcgcttttttg cgtggttgct
cccgcaagtt tccttctctg gagcttcccg caggtgggca gctagctgca gcgactaccg
catcatcaca gcctgttgaa ctcttctgag caagagaagg ggaggcgggg taagggaagt
aggtggaaga ttcagccaag ctcaaggatg gaagtgcagt tagggctggg aagggtctac
cctcggccgc cgtccaagac ctaccgagga gctttccaga atctgttcca gagcgtgcgc
gaagtgatcc agaacccggg ccccaggcac ccagaggccg cgagcgcagc acctcccggc
gccagtttgc tgctgcagca gcagcagcag cagcagcagc agcagcagca gcagcagcag
cagcagcagc agcagcagca gcagcagcag cagcagcagc aagagactag ccccaggcag
cagcagcagc agcagggtga ggatggttct ccccaagccc atcgtagagg ccccacaggc
tacctggtcc tggatgagga acagcaacct tcacagccgc agtcggccct ggagtgccac
cccgagagag gttgcgtccc agagcctgga gccgccgtgg ccgccagcaa ggggctgccg
cagcagctgc cagcacctcc ggacgaggat gactcagctg ccccatccac gttgtccctg
ctgggcccca ctttccccgg cttaagcagc tgctccgctg accttaaaga catcctgagc
gaggccagca ccatgcaact ccttcagcaa cagcagcagg aagcagtatc cgaaggcagc
agcagcggga gagcgaggga ggcctcgggg gctcccactt cctccaagga caattactta
ggggcactt cgaccatttc tgacaacgcc aaggagttgt gtaaggcagt gtcggtgtcc
atgggcctgg tgtggaggc gttggagcat ctgagtccag gggaacagct tcggggggat
tgcatgtacg ccccactttt gggagttcca cccgctgtgc gtcccactcc ttgtgcccca
ttggccgaat gcaaaggttc tctgctagac gacagcgcag gcaagagcac tgaagatact
gctgagtatt cccctttcaa gggaggttac accaaagggc tagaaggcga gagcctaggc
tgctctggca gcgctgcagc agggagctcc gggacacttg aactgccgtc tacctgtct
ctctacaagt ccggagcact ggacgaggca gctgcgtacc agagtcgcga ctactacaac
tttccactgg ctctggccgg acgccgcgcc cctccgccgc ctccccatcc ccacgctcgc
atcaagctgg agaaccgct ggactacggc agcgcctggg cggctgcggc ggcgcagtgc
cgctatgggg acctggcgag cctgcatggc gcgggtgcag cgggacccgg ttctgggtca
ccctcagccg ccgcttcctc atcctggcac actctcttca cagccgaaga aggccagttg
tatggaccgt gtggtggtgg tgggggtggt ggcggcggcg gcggcggcgg cggcggcggc
ggcggcggcg aggcgggagc tgtagccccc tacggctaca ctcggccccc tcaggggctg
gcgggccagg aaagcgactt caccgcacct gatgtgtggt accctggcgg catggtgagc
agagtgccct atcccagtcc cacttgtgtc aaaagcgaaa tgggccctg gatggatagc
tactccggac cttacgggga catgcgaaat acccgaagaa agagactctg gaaactcatt
atcaggtcta tcaactcttg tatttgttct cccaggggaaa cagaagtacc tgtgcgccag
cagaaatgat tgcactattg ataaattccg aaggaaaaat tgtccatctt gtcgtcttcg
gaaatgttat gaagcaggga tgactctggg agaaaaattc cggttggca attgcaagca
tctcaaaatg accagaccct gaagaaaggc tgacttgcct cattcaaaat gagggctcta
gagggctcta gtggatagtc tggagaaacc tggcgtctga ggcttaggag cttaggtttt
tgctcctcaa cacagacttt gacgttgggg ttgggggcta ctctcttgat tgctgactcc
ctccagcggg accaatagtg ttttcctacc tcacagggat gttgtgagga cgggctgtag
aagtaatagt ggttaccact catgtagttg tgagtatcat gattattgtt cctgtaatg
tggcttggca ttggcaaagt gcttttgat tgttcttgat cacatatgat ggggccagg
cactgactca ggcggatgca gtgaagctct ggctcagtcg cttcttttc gtggtgtgct
gccaggaaga aactttgctg atgggactca aggtgtcacc ttggacaaga agcaactgtg
tctgtctgag gttcctgtgg ccatctttat ttgtgtatta ggcaattcgt atttcccct
taggttctag ccttctggat cccagccagt gacctagatc ttagcctcag gccctgtcac
tgagctgaag gtagtagctg atccacagaa gttcagtaaa caaggaccag atttctgctt
ctccaggaga agaagccagc caacccctct cttcaaacac actgagagac tacagtccga
ctttccctct tacatctagc cttactgtag ccacactcct tgattgctct ctcacatcac
atgcttctct tcatcagttg taagcctctc attcttctcc caagccagac tcaaatattg
tattgatgtc aagaagaat cacttagagt ttggaatatc ttgttctctc tctgctccat
agcttccata ttgacaccag tttctttcta gtggagaagt ggagtctgtg aagccaggga
```

Figure 25B/2

```
aacacacatg tgagagtcag aaggactctc cctgacttgc ctggggcctg tctttcccac
cttctccagt ctgtctaaac acacacacac acacacacac acacacacac acacacacac
acgctctctc tctctctccc ccccaacac acacacactc tctctctcac acacacacac
atacacacac acttctttct ctttcccctg actcagcaac attctggaga aaagccaagg
aaggacttca ggaggggagt ttccccttc tcagggcaga attttaatct ccagaccaac
aagaagttcc ctaatgtgga ttgaaaggct aatgaggttt attttaact actttctatt
tgtttgaatg ttgcatattt ctactagtga aattttccct taataaagcc attaatacac
ccaaaaaaa aaaaaaaa
```

Human AR8 protein sequence

MEVQLGLGRVYPRPPSKTYRGAFQNLFQSVREVIQNPGPRHPEAAS
AAPPGASLLLQQQQQQQQQQQQQQQQQQQQQQQQQQQETSPR
QQQQGGGEDGSPQAHRRGPTGYLVLDEEQQPSQPQSALECHPERG
CVPEPGAAVAASKGLPGQLPAPPDEDDSAAPSTLSLLGPTFPGLSSC
SADLKDILSEASTMQLLQQQQQEAVSEGSSSGRAREASGAPTSSKD
NYLGGTSTISDNAKELCKAVSVSMGLGVEALEHLSPGEQLRGDCMYA
PLLGVPPAVRPTPCAPLAECKGSLLDDSAGKSTEDTAEYSPFKGGYT
KGLEGESLGCSGSAAAGSSGTLELPSTLSLYKSGALDEAAAYQSRDY
YNFPLALAGPFPPPPPPHPHARIKLENPLDYGSAWAAAAAQCRYGDL
ASLHGAGAAGPGSGSPSAAASSSWHTLFTAEEGQLYGPCGGGGGG
GGGGGGGGGGGGEAGAVAPYGYTRPPQGLAGQESDFTAPDVWYP
GGMVSRVPYPSPTCVKSEMGPWMDSYSGPYGDMRNTRKRLWKLI
RSINSCICSPRETEVPVRQQKStop

B

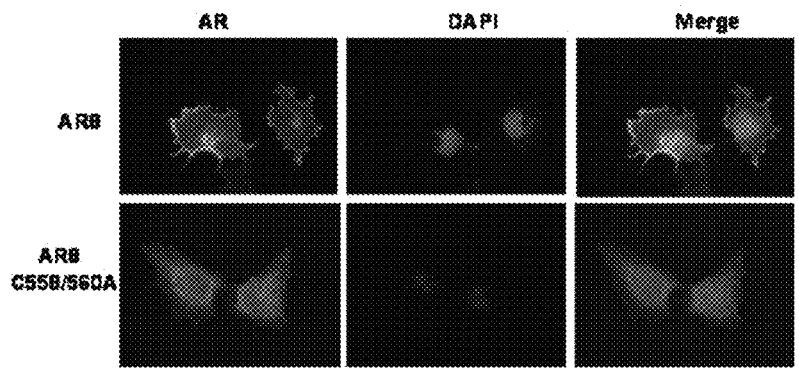

Fig 27
A
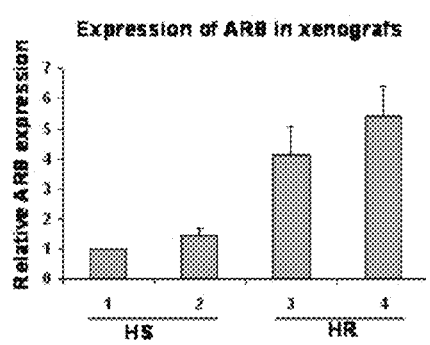
B
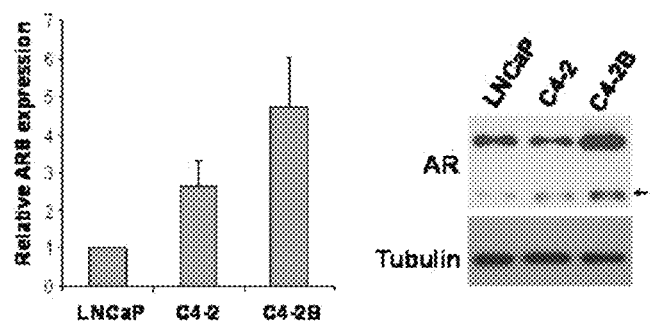

Fig 29
A
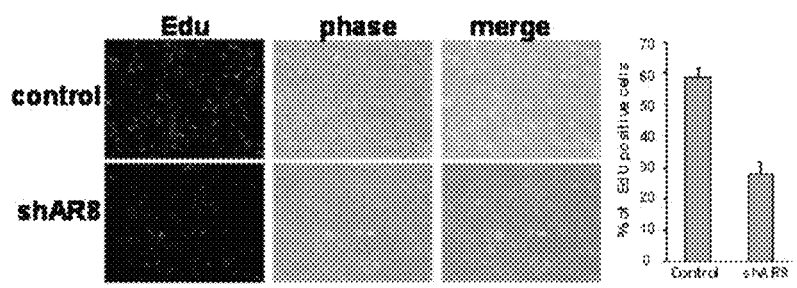
B
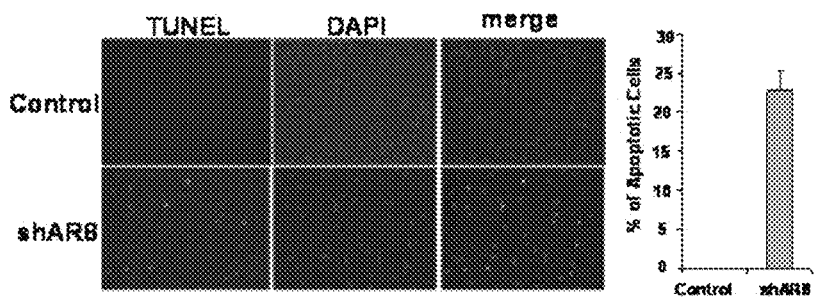

SEQUENCE LISTING

```
<160> NUMBER OF SEQ ID NOS: 38

<210> SEQ ID NO 1
<211> LENGTH: 3641
<212> TYPE: DNA
<213> ORGANISM: Homo sapiens

<400> SEQUENCE: 1
```

```
gacactgaat tggaaggtg gaggattttg ttttttctt ttaagatctg ggcatctttt      60
gaatctaccc ttcaagtatt aagagacaga ctgtgagcct agcagggcag atcttgtcca    120
ccgtgtgtct tcttctgcac gagactttga ggctgtcaga gcgctttttg cgtggttgct   180
cccgcaagtt tccttctctg gagcttcccg caggtgggca gctagctgca gcgactaccg   240
catcatcaca gcctgttgaa ctcttctgag caagagaagg ggaggcgggg taagggaagt   300
aggtggaaga ttcagccaag ctcaaggatg gaagtgcagt tagggctggg aagggtctac   360
cctcggccgc cgtccaagac ctaccgagga gctttccaga atctgttcca gagcgtgcgc   420
gaagtgatcc agaacccggg ccccaggcac ccagaggccg cgagcgcagc acctcccggc   480
gccagtttgc tgctgcagca gcagcagcag cagcagcagc agcagcagca gcagcagcag   540
cagcagcagc agcagcagca gcagcagcag cagcagcagc aagagactag ccccaggcag   600
cagcagcagc agcagggtga ggatggttct ccccaagccc atcgtagagg ccccacaggc   660
tacctggtcc tggatgagga acagcaacct tcacagccgc agtcggccct ggagtgccac   720
cccgagagag gttgcgtccc agagcctgga ccgccgtgg ccgccagcaa ggggctgccg    780
cagcagctgc cagcacctcc ggacgaggat gactcagctg ccccatccac gttgtccctg   840
ctgggcccca cttccccgg cttaagcagc tgctccgctg accttaaaga catcctgagc    900
gaggccagca ccatgcaact ccttcagcaa cagcagcagg aagcagtatc cgaaggcagc   960
agcagcggga gcgcaggga ggcctcgggg gctcccactt cctccaagga caattactta   1020
gggggcactt cgaccatttc tgacaacgcc aaggagttgt gtaaggcagt gtcggtgtcc   1080
atgggcctgg gtgtggaggc gttggagcat ctgagtccag gggaacagct tcgggggat    1140 tgcatgtacg ccccactttt gggagttcca cccgctgtgc gtcccactcc ttgtgcccca   1200
ttggccgaat gcaaaggttc tctgctagac gacagcgcag gcaagagcac tgaagatact   1260
gctgagtatt ccccttttcaa gggaggttac accaaagggc tagaaggcga gagcctaggc   1320
tgctctggca gcgctgcagc agggagctcc gggacacttg aactgccgtc taccctgtct   1380
ctctacaagt ccggagcact ggacgaggca gctgcgtacc agagtcgcga ctactacaac   1440
tttccactgg ctctggccgg accgccgccc cctccgccgc ctccccatcc ccacgctcgc   1500
atcaagctgg agaacccgct ggactacggc agcgcctggg cggctgcggc ggcgcagtgc   1560
cgctatgggg acctggcgag cctgcatggc gcgggtgcag cgggacccgg ttctgggtca   1620
ccctcagccg ccgcttcctc atcctggcac actctcttca cagccgaaga aggccagttg   1680 tatgaccgt gtggtggtgg tggggtggt ggcggcggcg gcggcggcgg cggcggcggc     1740
ggcggcggcg aggcgggagc tgtagccccc tacggctaca ctcggccccc tcagggctg    1800 gcgggccagg aaaagcgactt caccgcacct gatgtgtggt accctggcgg catggtgagc   1860
agagtgccct atcccagtcc cacttgtgtc aaaagcgaaa tgggcccctg gatggatagc   1920
tactccggac cttacgggga catgcgtttg gagactgcca ggaccatgt tttgccatt     1980 gactattact ttccaccca gaagacctgc ctgatctgtg gagatgaagc ttctgggtgt   2040
cactatggag ctctcacatg tggaagctgc aaggtcttct tcaaaagagc cgctgaaggg   2100
aaacagaagt acctgtgcgc cagcagaaat gattgcacta ttgataaatt ccgaaggaaa   2160
aattgtccat cttgtcgtct tcggaaatgt tatgaagcag ggatgactct gggagaaaaa   2220
ttccgggttg gcaattgcaa gcatctcaaa atgaccagac cctgaagaaa ggctgacttg   2280
cctcattcaa aatgagggct ctagagggct ctagtggata gtctggagaa acctggcgtc   2340
```

```
tgaggcttag gagcttaggt ttttgctcct caacacagac tttgacgttg gggttggggg    2400
ctactctctt gattgctgac tccctccagc gggaccaata gtgttttcct acctcacagg    2460
gatgttgtga ggacgggctg tagaagtaat agtggttacc actcatgtag ttgtgagtat    2520
catgattatt gtttcctgta atgtggcttg gcattggcaa agtgcttttt gattgttctt    2580
gatcacatat gatgggggcc aggcactgac tcaggcggat gcagtgaagc tctggctcag    2640
tcgcttgctt ttcgtggtgt gctgccagga agaaactttg ctgatgggac tcaaggtgtc    2700
accttggaca agaagcaact gtgtctgtct gaggttcctg tggccatctt tatttgtgta    2760
ttaggcaatt cgtatttccc ccttaggttc tagccttctg gatcccagcc agtgacctag    2820
atcttagcct caggccctgt cactgagctg aaggtagtag ctgatccaca gaagttcagt    2880
aaacaaggac cagatttctg cttctccagg agaagaagcc agccaacccc tctcttcaaa    2940
cacactgaga gactacagtc cgactttccc tcttacatct agccttactg tagccacact    3000
ccttgattgc tctctcacat cacatgcttc tcttcatcag ttgtaagcct ctcattcttc    3060
tcccaagcca gactcaaata ttgtattgat gtcaaagaag aatcacttag agtttggaat    3120
atcttgttct ctctctgctc catagcttcc atattgacac cagtttcttt ctagtggaga    3180
agtggagtct gtgaagccag ggaaacacac atgtgagagt cagaaggact ctccctgact    3240
tgcctggggc ctgtctttcc caccttctcc agtctgtcta aacacacaca cacacacaca    3300
cacacacaca cacacacaca cacacgctct ctctctctct ccccccccaa cacacacaca    3360
ctctctctct cacacacaca cacatacaca cacacttctt tctctttccc ctgactcagc    3420
aacattctgg agaaaagcca aggaaggact tcaggagggg agtttccccc ttctcagggc    3480
agaattttaa tctccagacc aacaagaagt tccctaatgt ggattgaaag gctaatgagg    3540
tttattttta actactttct atttgtttga atgttgcata tttctactag tgaaattttc    3600
ccttaataaa gccattaata cacccaaaaa aaaaaaaaa a                         3641

<210> SEQ ID NO 2
<211> LENGTH: 2896
<212> TYPE: DNA
<213> ORGANISM: Homo sapiens

<400> SEQUENCE: 2
gacactgaat ttggaaggtg gaggattttg ttttttttctt ttaagatctg ggcatctttt      60
gaatctaccc ttcaagtatt aagagacaga ctgtgagcct agcagggcag atcttgtcca    120
ccgtgtgtct tcttctgcac gagactttga ggctgtcaga gcgcttttg cgtggttgct     180 cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaaggatg gaagtgcagt tagggctggg aagggtctac    360
cctcggccgc cgtccaagac ctaccgagga gctttccaga atctgttcca gagcgtgcgc    420
gaagtgatcc agaacccggg ccccaggcac ccagaggccg cgagcgcagc acctcccggc    480
gccagtttgc tgctgcagca gcagcagcag cagcagcagc agcagcagca gcagcagcag    540
cagcagcagc agcagcagca gcagcagcag cagcagcaag agactagccc caggcagcag    600
cagcagcagc agggtgagga tggttctccc caagcccatc gtagaggccc cacaggctac    660
ctggtcctgg atgaggaaca gcaaccttca cagccgcagt cggccctgga gtgccaccccc    720 gagagaggtt gcgtcccaga gcctggagcc gccgtggccg ccagcaaggg gctgccgcag    780
cagctgccag cacctccgga cgaggatgac tcagctgccc catccacgtt gtccctgctg    840
```

```
ggcccactt tccccggctt aagcagctgc tccgctgacc ttaaagacat cctgagcgag     900
gccagcacca tgcaactcct tcagcaacag cagcaggaag cagtatccga aggcagcagc    960
agcgggagag cgagggaggc ctcggggggct cccacttcct ccaaggacaa ttacttaggg  1020
ggcacttcga ccatttctga caacgccaag gagttgtgta aggcagtgtc ggtgtccatg   1080
ggcctgggtg tggaggcgtt ggagcatctg agtccagggg aacagcttcg ggggattgc    1140
atgtacgccc cacttttggg agttccaccc gctgtgcgtc ccactccttg tgccccattg   1200
gccgaatgca aggttctct gctagacgac agcgcaggca agagcactga agatactgct    1260
gagtattccc ctttcaaggg aggttacacc aaagggctag aaggcgagag cctaggctgc   1320
tctggcagcg ctgcagcagg gagctccggg acacttgaac tgccgtctac cctgtctctc   1380
tacaagtccg gagcactgga cgaggcagct gcgtaccaga gtcgcgacta ctacaacttt   1440
ccactggctc tggccggacc gccgcccct ccgccgcctc ccatcccca cgctcgcatc     1500
aagctggaga acccgctgga ctacggcagc gcctgggcgg ctgcggcggc gcagtgccgc   1560
tatggggacc tggcgagcct gcatggcgcg ggtgcagcgg acccggttc tgggtcaccc    1620
tcagccgccg cttcctcatc ctggcacact ctcttcacag ccgaagaagg ccagttgtat   1680
ggaccgtgtg gtggtggtgg gggtggtggc ggcggcggcg gcggcggcgg cggcggcggc   1740
ggcggcgagg cgggagctgt agcccctac ggctacactc ggccccctca ggggctggcg    1800
ggccaggaaa gcgacttcac cgcacctgat gtgtggtacc ctggcggcat ggtgagcaga   1860
gtgccctatc ccagtcccac ttgtgtcaaa agcgaaatgg gccctggat ggatagctac    1920
tccggaccctt acggggacat cgtttggag actgccaggg accatgtttt gcccattgac   1980
tattactttc cacccagaa gacctgcctg atctgtggag atgaagcttc tgggtgtcac   2040
tatggagctc tcacatgtgg aagctgcaag gtcttcttca aaagagccgc tgaagggaaa   2100
cagaagtacc tgtgcgccag cagaaatgat tgcactattg ataaattccg aaggaaaaat   2160
tgtccatctt gtcgtcttcg gaaatgttat gaagcaggga tgactctggg agcagctgtt   2220
gttgtttctg aaagaatctt gagggtgttt ggagtctcag aatggcttcc ttaaagacta   2280
ccttcagact ctcagctgct catccacaac agagatcagc ctttctttgt agatgattca   2340
ttcctggctg catttgaaaa ccacatattg ttaattgctt gacgaattta aatcccttga   2400
ctacttttca tttcagaaaa cacttacaaa aaagtccaa atgaggacct tccctccagt    2460
gaattagctg tggctttctc acagtccata gttaggataa atgtaaagcc atttctcatt   2520
tttctccgca ctttccaagg gtacactcct tgtttccaag atggaatgag aaataaagaa   2580
gtgccccttcc ccaaacatga ttcattttctg cgttttgcaa ctcttgagtt ctcagcattt  2640
agtaaatggt gttggtccct gttgattcct tcctctcctg gaccatggaa ggtagtaggc   2700
cttttcagaaa tttcaggtag cagccaaacc ccagaagaag agaaggaaca cagagaccta   2760
gaccatgtga aacctgagg tgtgcagcat ttacttcaca gattcgtcta gcatatttga    2820
gaggtgtctt tcctactagg agactgaact ctgcatctga aataaaaac ttaacatatc    2880
aaaaaaaaaa aaaaaa                                                   2896
```

<210> SEQ ID NO 3  
<211> LENGTH: 4039  
<212> TYPE: DNA  
<213> ORGANISM: Homo sapiens

<400> SEQUENCE: 3

```
gacactgaat ttggaaggtg gaggattttg ttttttcctt ttaagatctg ggcatctttt      60
gaatctaccc ttcaagtatt aagagacaga ctgtgagcct agcagggcag atcttgtcca     120
ccgtgtgtct tcttctgcac gagactttga ggctgtcaga gcgcttttg cgtggttgct     180
cccgcaagtt tccttctctg gagcttcccg caggtgggca gctagctgca gcgactaccg     240
catcatcaca gcctgttgaa ctcttctgag caagagaagg ggaggcgggg taagggaagt     300
aggtggaaga ttcagccaag ctcaaggatg gaagtgcagt tagggctggg aagggtctac     360
cctcggccgc cgtccaagac ctaccgagga gctttccaga atctgttcca gagcgtgcgc     420
gaagtgatcc agaacccggg ccccaggcac ccagaggccg cgagcgcagc acctcccggc     480
gccagtttgc tgctgcagca gcagcagcag cagcagcagc agcagcagca gcagcagcag     540
cagcagcagc agcagcagca gcagcagcag cagcagcagc aagagactag ccccaggcag     600
cagcagcagc agcagggtga ggatggttct ccccaagccc atcgtagagg ccccacaggc     660
tacctggtcc tggatgagga acagcaacct tcacagccgc agtcggccct ggagtgccac     720
cccgagagag gttgcgtccc agagcctgga gccgccgtgg ccgccagcaa ggggctgccg     780
cagcagctgc cagcacctcc ggacgaggat gactcagctg ccccatccac gttgtccctg     840
ctgggcccca ctttccccgg cttaagcagc tgctccgctg accttaaaga catcctgagc     900
gaggccagca ccatgcaact ccttcagcaa cagcagcagg aagcagtatc cgaaggcagc     960
agcagcggga gagcgaggga ggcctcgggg gctcccactt cctccaagga caattactta    1020
ggggcacctt cgaccatttc tgacaacgcc aaggagttgt gtaaggcagt gtcggtgtcc    1080
atgggcctgg gtgtggaggc gttggagcat ctgagtccag ggaacagct tcgggggggat    1140
tgcatgtacg ccccactttt gggagttcca cccgctgtgc gtcccactcc ttgtgcccca    1200
ttggccgaat gcaaaggttc tctgctagac gacagcgcag gcaagagcac tgaagatact    1260
gctgagtatt cccctttcaa gggaggttac accaaagggc tagaaggcga gagcctaggc    1320
tgctctggca gcgctgcagc agggagctcc gggacacttg aactgccgtc taccctgtct    1380
ctctacaagt ccggagcact ggacgaggca gctgcgtacc agagtcgcga ctactacaac    1440
tttccactgg ctctgccggg accgccgccc ctccgccgc ctccccatcc ccacgctcgc    1500
atcaagctgg agaacccgct ggactacggc agcgcctggg cggctgcggc ggcgcagtgc    1560
cgctatgggg acctggcgag cctgcatggc gcgggtgcag cgggacccgg ttctgggtca    1620
ccctcagccg ccgcttcctc atcctggcac actctcttca cagccgaaga aggccagttg    1680
tatggaccgt gtggtggtgg tggggggtggt ggcggcggcg gcggcggcgg cggcggcggc    1740
ggcggcggcg aggcgggagc tgtagccccc tacggctaca ctcggcccc tcaggggctg    1800
gcgggccagg aaaagcgactt caccgcacct gatgtgtggt accctggcgg catggtgagc    1860
agagtgccct atcccagtcc cacttgtgtc aaaagcgaaa tgggcccctg gatggatagc    1920
tactccggac cttacgggga catgcgtttg gagactgcca gggaccatgt tttgcccatt    1980
gactattact ttcaccccca gaagacctgc ctgatctgtg gagatgaagc ttctgggtgt    2040
cactatggag ctctcacatg tggaagctgc aaggtcttct tcaaaagagc cgctgaaggg    2100
aaacagaagt acctgtgcgc cagcagaaat gattgcacta ttgataaatt ccgaaggaaa    2160
aattgtccat cttgtcgtct tcggaaatgt tatgaagcag ggatgactct gggaggattt    2220
ttcagaatga acaaattaaa agaatcatca gacactaacc ccaagccata ctgcatggca    2280
gcaccaatgg gactgacaga aaacaacaga aataggaaga aatcctacag agaaacaaac    2340
ttgaaagctg tctcatggcc tttgaatcat acttaagttt tatgatggaa ggatacgact    2400
```

```
atgaagaaag acacagagca acatcagaca gtcaagaatt tcagagccag ctggcatgca    2460
gtggacctca tgccagccca ttttatgact atttagggaa acagaagtac ctgtgcgcca    2520
gcagaaatga ttgcactatt gataaattcc gaaggaaaaa ttgtccatct tgtcgtcttc    2580
ggaaatgtta tgaagcaggg atgactctgg agaaaaatt ccgggttggc aattgcaagc     2640
atctcaaaat gaccagaccc tgaagaaagg ctgacttgcc tcattcaaaa tgagggctct    2700
agagggctct agtggatagt ctggagaaac ctggcgtctg aggcttagga gcttaggttt    2760
ttgctcctca acacagactt tgacgttggg gttgggggct actctcttga ttgctgactc    2820
cctccagcgg gaccaatagt gttttcctac ctcacaggga tgttgtgagg acgggctgta    2880
gaagtaatag tggttaccac tcatgtagtt gtgagtatca tgattattgt ttcctgtaat    2940
gtggcttggc attggcaaag tgcttttga ttgttcttga tcacatatga tggggggccag    3000 gcactgactc aggcggatgc agtgaagctc tggctcagtc gcttgctttt cgtggtgtgc    3060
tgccaggaag aaactttgct gatgggactc aaggtgtcac cttggacaag aagcaactgt    3120
gtctgtctga ggttcctgtg ccatcttta tttgtgtatt aggcaattcg tatttccccc     3180
ttaggttcta gccttctgga tcccagccag tgacctagat cttagcctca ggccctgtca    3240
ctgagctgaa ggtagtagct gatccacaga agttcagtaa acaaggacca gatttctgct    3300
tctccaggag aagaagccag ccaacccctc tcttcaaaca cactgagaga ctacagtccg    3360
actttccctc ttacatctag ccttactgta gccacactcc ttgattgctc tctcacatca    3420
catgcttctc ttcatcagtt gtaagcctct cattcttctc ccaagccaga ctcaaatatt    3480
gtattgatgt caaagaagaa tcacttagag tttggaatat cttgttctct ctctgctcca    3540
tagcttccat attgacacca gtttctttct agtggagaag tggagtctgt gaagccaggg    3600
aaacacacat gtgagagtca gaaggactct ccctgacttg cctggggcct gtctttccca    3660
ccttctccag tctgtctaaa cacacacaca cacacacaca cacacacaca cacacacaca    3720
cacgctctct ctctctctcc cccccaaca cacacacact ctctctctca cacacacaca     3780
catacacaca cacttctttc tctttcccct gactcagcaa cattctggag aaaagccaag    3840
gaaggacttc aggaggggag tttcccccctt ctcagggcag aatttttaatc tccagaccaa   3900 caagaagttc cctaatgtgg attgaaaggc taatgaggtt tattttttaac tactttctat    3960 ttgtttgaat gttgcatatt tctactagtg aaattttccc ttaataaagc cattaataca    4020
cccaaaaaaa aaaaaaaaa                                                  4039
```

<210> SEQ ID NO 4
<211> LENGTH: 3558
<212> TYPE: DNA
<213> ORGANISM: Homo sapiens

<400> SEQUENCE: 4

```
gacactgaat ttggaaggtg gaggattttg ttttttttctt ttaagatctg ggcatctttt     60
gaatctaccc ttcaagtatt aagagacaga ctgtgagcct agcagggcag atcttgtcca    120
ccgtgtgtct tcttctgcac gagactttga ggctgtcaga gcgcttttg cgtggttgct     180 cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaaggatg gaagtgcagt tagggctggg aagggtctac    360
cctcggccgc cgtccaagac ctaccgagga gctttccaga atctgttcca gagcgtgcgc    420
```

```
gaagtgatcc agaacccggg ccccaggcac ccagaggccg cgagcgcagc acctcccggc    480
gccagtttgc tgctgcagca gcagcagcag cagcagcagc agcagcagca gcagcagcag    540
cagcagcagc agcagcagca gcagcagcag cagcagcagc aagagactag ccccaggcag    600
cagcagcagc agcagggtga ggatggttct ccccaagccc atcgtagagg ccccacaggc    660
tacctggtcc tggatgagga acagcaacct tcacagccgc agtcggccct ggagtgccac    720
cccgagagag gttgcgtccc agagcctgga gccgccgtgg ccgccagcaa ggggctgccg    780
cagcagctgc cagcacctcc ggacgaggat gactcagctg ccccatccac gttgtccctg    840
ctgggcccca cttccccggg cttaagcagc tgctccgctg accttaaaga catcctgagc    900
gaggccagca ccatgcaact ccttcagcaa cagcagcagg aagcagtatc cgaaggcagc    960
agcagcggga gagcgaggga ggcctcgggg gctcccactt cctccaagga caattactta   1020
gggggcactt cgaccatttc tgacaacgcc aaggagttgt gtaaggcagt gtcggtgtcc   1080
atgggcctgg gtgtggaggc gttggagcat ctgagtccag gggaacagct tcggggggat   1140
tgcatgtacg ccccactttt gggagttcca cccgctgtgc gtcccactcc ttgtgcccca   1200
ttggccgaat gcaaaggttc tctgctagac acagcgcag gcaagagcac tgaagatact   1260
gctgagtatt ccccttttcaa gggaggttac accaaagggc tagaaggcga gagcctaggc   1320
tgctctggca gcgctgcagc agggagctcc gggacacttg aactgccgtc taccctgtct   1380
ctctacaagt ccggagcact ggacgaggca gctgcgtacc agagtcgcga ctactacaac   1440
tttccactgg ctctggccgg accgccgccc cctccgccgc ctccccatcc ccacgctcgc   1500
atcaagctga gaacccgct ggactacggc agcgcctggg cggctgccgg ggcgcagtgc   1560
cgctatgggg acctggcgag cctgcatggc gcgggtgcag cgggacccgg ttctgggtca   1620
ccctcagccg ccgcttcctc atcctggcac actctcttca cagccgaaga aggccagttg   1680
tatggaccgt gtggtggtgg tgggggtggt ggcggcggcg gcggcggcgg cggcggcggc   1740
ggcggcggcg aggcgggagc tgtagccccc tacggctaca ctcggccccc tcaggggctg   1800
gcgggccagg aaagcgactt caccgcacct gatgtgtggt accctggcgg catggtgagc   1860
agagtgccct atcccagtcc cacttgtgtc aaaagcgaaa tgggcccctg gatggatagc   1920
tactccggac cttacgggga catgcgaaat acccgaagaa agagactctg gaaactcatt   1980
atcaggtcta tcaactcttg tatttgttct cccaggaaaa cagaagtacc tgtgcgccag   2040
cagaaatgat tgcactattg ataaattccg aaggaaaaat tgtccatctt gtcgtcttcg   2100
gaaatgttat gaagcaggga tgactctggg agaaaaattc cgggttggca attgcaagca   2160
tctcaaaatg accagaccct gaagaaaggc tgacttgcct cattcaaaat gagggctcta   2220
gagggctcta gtggatagtc tggagaaacc tggcgtctga ggcttaggag cttaggtttt   2280
tgctcctcaa cacagacttt gacgttgggg ttggggccta ctctcttgat tgctgactcc   2340
ctccagcggg accaatagtg ttttcctacc tcacagggat gttgtgagga cgggctgtag   2400
aagtaatagt ggttaccact catgtagttg tgagtatcat gattattgtt tcctgtaatg   2460
tggcttggca ttggcaaagt gcttttttgat tgttcttgat cacatatgat gggggccagg   2520
cactgactca gcggatgca gtgaagctct ggctcagtcg cttgcttttc gtggtgtgct   2580
gccaggaaga aactttgctg atgggactca aggtgtcacc ttgacaaga agcaactgtg   2640 tctgtctgag gttcctgtgg ccatctttat ttgtgtatta ggcaattcgt atttcccct   2700 taggttctag ccttctggat cccagccagt gacctagatc ttagcctcag gccctgtcac   2760
tgagctgaag gtagtagctg atccacagaa gttcagtaaa caaggaccag atttctgctt   2820
```

```
ctccaggaga agaagccagc caacccctct cttcaaacac actgagagac tacagtccga    2880 cttccctct  tacatctagc cttactgtag ccacactcct tgattgctct ctcacatcac    2940
atgcttctct tcatcagttg taagcctctc attcttctcc caagccagac tcaaatattg    3000
tattgatgtc aaagaagaat cacttagagt ttggaatatc ttgttctctc tctgctccat    3060
agcttccata ttgacaccag tttctttcta gtggagaagt ggagtctgtg aagccaggga    3120
aacacacatg tgagagtcag aaggactctc cctgacttgc ctggggcctg tctttcccac    3180
cttctccagt ctgtctaaac acacacacac acacacacac acacacacac acacacacac    3240
acgctctctc tctctctccc cccccaacac acacacactc tctctctcac acacacacac    3300
atacacacac acttctttct ctttcccctg actcagcaac attctggaga aaagccaagg    3360
aaggacttca ggaggggagt ttccccctc  tcagggcaga attttaatct ccagaccaac    3420
aagaagttcc ctaatgtgga ttgaaaggct aatgaggttt attttaact  actttctatt    3480 tgtttgaatg ttgcatattt ctactagtga aattttccct taataaagcc attaatacac    3540
ccaaaaaaaa aaaaaaaa                                                  3558

<210> SEQ ID NO 5
<211> LENGTH: 645
<212> TYPE: PRT
<213> ORGANISM: Homo sapiens

<400> SEQUENCE: 5

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Glu Thr Ser Pro Arg Gln Gln Gln Gln Gln Gln
                85                  90                  95

Gly Glu Asp Gly Ser Pro Gln Ala His Arg Arg Gly Pro Thr Gly Tyr
            100                 105                 110

Leu Val Leu Asp Glu Glu Gln Gln Pro Ser Gln Pro Gln Ser Ala Leu
        115                 120                 125

Glu Cys His Pro Glu Arg Gly Cys Val Pro Glu Pro Gly Ala Ala Val
    130                 135                 140

Ala Ala Ser Lys Gly Leu Pro Gln Gln Leu Pro Ala Pro Pro Asp Glu
145                 150                 155                 160

Asp Asp Ser Ala Ala Pro Ser Thr Leu Ser Leu Leu Gly Pro Thr Phe
                165                 170                 175

Pro Gly Leu Ser Ser Cys Ser Ala Asp Leu Lys Asp Ile Leu Ser Glu
            180                 185                 190

Ala Ser Thr Met Gln Leu Leu Gln Gln Gln Gln Glu Ala Val Ser
        195                 200                 205

Glu Gly Ser Ser Ser Gly Arg Ala Arg Glu Ala Ser Gly Ala Pro Thr
    210                 215                 220

Ser Ser Lys Asp Asn Tyr Leu Gly Gly Thr Ser Thr Ile Ser Asp Asn
225                 230                 235                 240
```

-continued

```
Ala Lys Glu Leu Cys Lys Ala Val Ser Val Ser Met Gly Leu Gly Val
            245                 250                 255
Glu Ala Leu Glu His Leu Ser Pro Gly Glu Gln Leu Arg Gly Asp Cys
        260                 265                 270
Met Tyr Ala Pro Leu Leu Gly Val Pro Pro Ala Val Arg Pro Thr Pro
    275                 280                 285
Cys Ala Pro Leu Ala Glu Cys Lys Gly Ser Leu Leu Asp Asp Ser Ala
    290                 295                 300
Gly Lys Ser Thr Glu Asp Thr Ala Glu Tyr Ser Pro Phe Lys Gly Gly
305                 310                 315                 320
Tyr Thr Lys Gly Leu Glu Gly Ser Leu Gly Cys Ser Gly Ser Ala
                325                 330                 335
Ala Ala Gly Ser Ser Gly Thr Leu Glu Leu Pro Ser Thr Leu Ser Leu
            340                 345                 350
Tyr Lys Ser Gly Ala Leu Asp Glu Ala Ala Tyr Gln Ser Arg Asp
        355                 360                 365
Tyr Tyr Asn Phe Pro Leu Ala Leu Ala Gly Pro Pro Pro Pro Pro
    370                 375                 380
Pro Pro His Pro His Ala Arg Ile Lys Leu Glu Asn Pro Leu Asp Tyr
385                 390                 395                 400
Gly Ser Ala Trp Ala Ala Ala Ala Gln Cys Arg Tyr Gly Asp Leu
                405                 410                 415
Ala Ser Leu His Gly Ala Gly Ala Ala Gly Pro Gly Ser Gly Ser Pro
            420                 425                 430
Ser Ala Ala Ala Ser Ser Ser Trp His Thr Leu Phe Thr Ala Glu Glu
        435                 440                 445
Gly Gln Leu Tyr Gly Pro Cys Gly Gly Gly Gly Gly Gly Gly Gly
    450                 455                 460
Gly Gly Gly Gly Gly Gly Gly Gly Gly Glu Ala Gly Ala Val Ala
465                 470                 475                 480
Pro Tyr Gly Tyr Thr Arg Pro Pro Gln Gly Leu Ala Gly Gln Glu Ser
                485                 490                 495
Asp Phe Thr Ala Pro Asp Val Trp Tyr Pro Gly Gly Met Val Ser Arg
            500                 505                 510
Val Pro Tyr Pro Ser Pro Thr Cys Val Lys Ser Glu Met Gly Pro Trp
        515                 520                 525
Met Asp Ser Tyr Ser Gly Pro Tyr Gly Asp Met Arg Leu Glu Thr Ala
    530                 535                 540
Arg Asp His Val Leu Pro Ile Asp Tyr Tyr Phe Pro Pro Gln Lys Thr
545                 550                 555                 560
Cys Leu Ile Cys Gly Asp Glu Ala Ser Gly Cys His Tyr Gly Ala Leu
                565                 570                 575
Thr Cys Gly Ser Cys Lys Val Phe Phe Lys Arg Ala Ala Glu Gly Lys
            580                 585                 590
Gln Lys Tyr Leu Cys Ala Ser Arg Asn Asp Cys Thr Ile Asp Lys Phe
        595                 600                 605
Arg Arg Lys Asn Cys Pro Ser Cys Arg Leu Arg Lys Cys Tyr Glu Ala
    610                 615                 620
Gly Met Thr Leu Gly Glu Lys Phe Arg Val Gly Asn Cys Lys His Leu
625                 630                 635                 640
Lys Met Thr Arg Pro
                645
```

<210> SEQ ID NO 6
<211> LENGTH: 648
<212> TYPE: PRT
<213> ORGANISM: Homo sapiens

<400> SEQUENCE: 6

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Glu Thr Ser Pro Arg Gln Gln Gln Gln Gln Gln Gly
                85                  90                  95

Glu Asp Gly Ser Pro Gln Ala His Arg Arg Gly Pro Thr Gly Tyr Leu
            100                 105                 110

Val Leu Asp Glu Glu Gln Gln Pro Ser Gln Pro Gln Ser Ala Leu Glu
        115                 120                 125

Cys His Pro Glu Arg Gly Cys Val Pro Glu Pro Gly Ala Ala Val Ala
    130                 135                 140

Ala Ser Lys Gly Leu Pro Gln Gln Leu Pro Ala Pro Pro Asp Glu Asp
145                 150                 155                 160

Asp Ser Ala Ala Pro Ser Thr Leu Ser Leu Leu Gly Pro Thr Phe Pro
                165                 170                 175

Gly Leu Ser Ser Cys Ser Ala Asp Leu Lys Asp Ile Leu Ser Glu Ala
            180                 185                 190

Ser Thr Met Gln Leu Leu Gln Gln Gln Gln Glu Ala Val Ser Glu
        195                 200                 205

Gly Ser Ser Ser Gly Arg Ala Arg Glu Ala Ser Gly Ala Pro Thr Ser
    210                 215                 220

Ser Lys Asp Asn Tyr Leu Gly Gly Thr Ser Thr Ile Ser Asp Asn Ala
225                 230                 235                 240

Lys Glu Leu Cys Lys Ala Val Ser Val Ser Met Gly Leu Gly Val Glu
                245                 250                 255

Ala Leu Glu His Leu Ser Pro Gly Glu Gln Leu Arg Gly Asp Cys Met
            260                 265                 270

Tyr Ala Pro Leu Leu Gly Val Pro Pro Ala Val Arg Pro Thr Pro Cys
        275                 280                 285

Ala Pro Leu Ala Glu Cys Lys Gly Ser Leu Leu Asp Asp Ser Ala Gly
    290                 295                 300

Lys Ser Thr Glu Asp Thr Ala Glu Tyr Ser Pro Phe Lys Gly Gly Tyr
305                 310                 315                 320

Thr Lys Gly Leu Glu Gly Glu Ser Leu Gly Cys Ser Gly Ser Ala Ala
                325                 330                 335

Ala Gly Ser Ser Gly Thr Leu Glu Leu Pro Ser Thr Leu Ser Leu Tyr
            340                 345                 350

Lys Ser Gly Ala Leu Asp Glu Ala Ala Ala Tyr Gln Ser Arg Asp Tyr
        355                 360                 365

Tyr Asn Phe Pro Leu Ala Leu Ala Gly Pro Pro Pro Pro Pro Pro Pro
    370                 375                 380

```
Pro His Pro His Ala Arg Ile Lys Leu Glu Asn Pro Leu Asp Tyr Gly
385                 390                 395                 400

Ser Ala Trp Ala Ala Ala Ala Gln Cys Arg Tyr Gly Asp Leu Ala
            405                 410                 415

Ser Leu His Gly Ala Gly Ala Ala Gly Pro Gly Ser Gly Ser Pro Ser
            420                 425                 430

Ala Ala Ala Ser Ser Ser Trp His Thr Leu Phe Thr Ala Glu Glu Gly
            435                 440                 445

Gln Leu Tyr Gly Pro Cys Gly Gly Gly Gly Gly Gly Gly Gly
        450                 455                 460

Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
        610                 615                 620

Met Thr Leu Gly Ala Ala Val Val Val Ser Glu Arg Ile Leu Arg Val
625                 630                 635                 640

Phe Gly Val Ser Glu Trp Leu Pro
                645

<210> SEQ ID NO 7
<211> LENGTH: 682
<212> TYPE: PRT
<213> ORGANISM: Homo sapiens

<400> SEQUENCE: 7

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Glu Thr Ser Pro Arg Gln Gln Gln Gln Gln Gln
                85                  90                  95

Gly Glu Asp Gly Ser Pro Gln Ala His Arg Arg Gly Pro Thr Gly Tyr
```

```
                100             105             110
Leu Val Leu Asp Glu Glu Gln Gln Pro Ser Gln Pro Gln Ser Ala Leu
            115                 120             125

Glu Cys His Pro Glu Arg Gly Cys Val Pro Glu Pro Gly Ala Ala Val
            130                 135             140

Ala Ala Ser Lys Gly Leu Pro Gln Gln Leu Pro Ala Pro Pro Asp Glu
145             150                 155                 160

Asp Asp Ser Ala Ala Pro Ser Thr Leu Ser Leu Gly Pro Thr Phe
                165             170                 175

Pro Gly Leu Ser Ser Cys Ser Ala Asp Leu Lys Asp Ile Leu Ser Glu
                180             185             190

Ala Ser Thr Met Gln Leu Leu Gln Gln Gln Gln Glu Ala Val Ser
            195                 200             205

Glu Gly Ser Ser Ser Gly Arg Ala Arg Glu Ala Ser Gly Ala Pro Thr
            210                 215             220

Ser Ser Lys Asp Asn Tyr Leu Gly Gly Thr Ser Thr Ile Ser Asp Asn
225                 230                 235                 240

Ala Lys Glu Leu Cys Lys Ala Val Ser Val Ser Met Gly Leu Gly Val
                245             250                 255

Glu Ala Leu Glu His Leu Ser Pro Gly Glu Gln Leu Arg Gly Asp Cys
            260                 265                 270

Met Tyr Ala Pro Leu Leu Gly Val Pro Pro Ala Val Arg Pro Thr Pro
            275                 280                 285

Cys Ala Pro Leu Ala Glu Cys Lys Gly Ser Leu Leu Asp Asp Ser Ala
            290                 295                 300

Gly Lys Ser Thr Glu Asp Thr Ala Glu Tyr Ser Pro Phe Lys Gly Gly
305                 310                 315                 320

Tyr Thr Lys Gly Leu Glu Gly Glu Ser Leu Gly Cys Ser Gly Ser Ala
                325                 330                 335

Ala Ala Gly Ser Ser Gly Thr Leu Glu Leu Pro Ser Thr Leu Ser Leu
                340                 345                 350

Tyr Lys Ser Gly Ala Leu Asp Glu Ala Ala Ala Tyr Gln Ser Arg Asp
            355                 360                 365

Tyr Tyr Asn Phe Pro Leu Ala Leu Ala Gly Pro Pro Pro Pro Pro Pro
            370                 375                 380

Pro Pro His Pro His Ala Arg Ile Lys Leu Glu Asn Pro Leu Asp Tyr
385                 390                 395                 400

Gly Ser Ala Trp Ala Ala Ala Ala Gln Cys Arg Tyr Gly Asp Leu
                405                 410                 415

Ala Ser Leu His Gly Ala Gly Ala Ala Gly Pro Gly Ser Gly Ser Pro
            420                 425                 430

Ser Ala Ala Ala Ser Ser Ser Trp His Thr Leu Phe Thr Ala Glu Glu
            435                 440                 445

Gly Gln Leu Tyr Gly Pro Cys Gly Gly Gly Gly Gly Gly Gly Gly Gly
            450                 455                 460

Gly Gly Gly Gly Gly Gly Gly Gly Gly Glu Ala Gly Ala Val Ala
465                 470                 475                 480

Pro Tyr Gly Tyr Thr Arg Pro Pro Gln Gly Leu Ala Gly Gln Glu Ser
                485                 490                 495

Asp Phe Thr Ala Pro Asp Val Trp Tyr Pro Gly Gly Met Val Ser Arg
            500                 505                 510

Val Pro Tyr Pro Ser Pro Thr Cys Val Lys Ser Glu Met Gly Pro Trp
            515                 520                 525
```

Met Asp Ser Tyr Ser Gly Pro Tyr Gly Asp Met Arg Leu Glu Thr Ala
530                 535                 540

Arg Asp His Val Leu Pro Ile Asp Tyr Tyr Phe Pro Pro Gln Lys Thr
545                 550                 555                 560

Cys Leu Ile Cys Gly Asp Glu Ala Ser Gly Cys His Tyr Gly Ala Leu
                565                 570                 575

Thr Cys Gly Ser Cys Lys Val Phe Phe Lys Arg Ala Ala Glu Gly Lys
            580                 585                 590

Gln Lys Tyr Leu Cys Ala Ser Arg Asn Asp Cys Thr Ile Asp Lys Phe
        595                 600                 605

Arg Arg Lys Asn Cys Pro Ser Cys Arg Leu Arg Lys Cys Tyr Glu Ala
    610                 615                 620

Gly Met Thr Leu Gly Gly Phe Phe Arg Met Asn Lys Leu Lys Glu Ser
625                 630                 635                 640

Ser Asp Thr Asn Pro Lys Pro Tyr Cys Met Ala Ala Pro Met Gly Leu
                645                 650                 655

Thr Glu Asn Asn Arg Asn Arg Lys Lys Ser Tyr Arg Glu Thr Asn Leu
            660                 665                 670

Lys Ala Val Ser Trp Pro Leu Asn His Thr
        675                 680

<210> SEQ ID NO 8
<211> LENGTH: 573
<212> TYPE: PRT
<213> ORGANISM: Homo sapiens

<400> SEQUENCE: 8

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Glu Thr Ser Pro Arg Gln Gln Gln Gln Gln Gln Gln
                85                  90                  95

Gly Glu Asp Gly Ser Pro Gln Ala His Arg Arg Gly Pro Thr Gly Tyr
            100                 105                 110

Leu Val Leu Asp Glu Glu Gln Gln Pro Ser Gln Pro Gln Ser Ala Leu
        115                 120                 125

Glu Cys His Pro Glu Arg Gly Cys Val Pro Glu Pro Gly Ala Ala Val
    130                 135                 140

Ala Ala Ser Lys Gly Leu Pro Gln Gln Leu Pro Ala Pro Pro Asp Glu
145                 150                 155                 160

Asp Asp Ser Ala Ala Pro Ser Thr Leu Ser Leu Leu Gly Pro Thr Phe
                165                 170                 175

Pro Gly Leu Ser Ser Cys Ser Ala Asp Leu Lys Asp Ile Leu Ser Glu
            180                 185                 190

Ala Ser Thr Met Gln Leu Leu Gln Gln Gln Gln Glu Ala Val Ser
        195                 200                 205

Glu Gly Ser Ser Ser Gly Arg Ala Arg Glu Ala Ser Gly Ala Pro Thr

-continued

```
            210                 215                 220
Ser Ser Lys Asp Asn Tyr Leu Gly Gly Thr Ser Thr Ile Ser Asp Asn
225                 230                 235                 240

Ala Lys Glu Leu Cys Lys Ala Val Ser Val Ser Met Gly Leu Gly Val
                245                 250                 255

Glu Ala Leu Glu His Leu Ser Pro Gly Glu Gln Leu Arg Gly Asp Cys
                260                 265                 270

Met Tyr Ala Pro Leu Leu Gly Val Pro Pro Ala Val Arg Pro Thr Pro
                275                 280                 285

Cys Ala Pro Leu Ala Glu Cys Lys Gly Ser Leu Leu Asp Asp Ser Ala
                290                 295                 300

Gly Lys Ser Thr Glu Asp Thr Ala Glu Tyr Ser Pro Phe Lys Gly Gly
305                 310                 315                 320

Tyr Thr Lys Gly Leu Glu Gly Glu Ser Leu Gly Cys Ser Gly Ser Ala
                325                 330                 335

Ala Ala Gly Ser Ser Gly Thr Leu Glu Leu Pro Ser Thr Leu Ser Leu
                340                 345                 350

Tyr Lys Ser Gly Ala Leu Asp Glu Ala Ala Tyr Gln Ser Arg Asp
                355                 360                 365

Tyr Tyr Asn Phe Pro Leu Ala Leu Ala Gly Pro Pro Pro Pro Pro
370                 375                 380

Pro Pro His Pro His Ala Arg Ile Lys Leu Glu Asn Pro Leu Asp Tyr
385                 390                 395                 400

Gly Ser Ala Trp Ala Ala Ala Ala Gln Cys Arg Tyr Gly Asp Leu
                405                 410                 415

Ala Ser Leu His Gly Ala Gly Ala Ala Gly Pro Gly Ser Gly Ser Pro
                420                 425                 430

Ser Ala Ala Ala Ser Ser Ser Trp His Thr Leu Phe Thr Ala Glu Glu
                435                 440                 445

Gly Gln Leu Tyr Gly Pro Cys Gly Gly Gly Gly Gly Gly Gly Gly
                450                 455                 460

Gly Gly Gly Gly Gly Gly Gly Gly Gly Glu Ala Gly Ala Val Ala
465                 470                 475                 480

Pro Tyr Gly Tyr Thr Arg Pro Pro Gln Gly Leu Ala Gly Gln Glu Ser
                485                 490                 495

Asp Phe Thr Ala Pro Asp Val Trp Tyr Pro Gly Gly Met Val Ser Arg
                500                 505                 510

Val Pro Tyr Pro Ser Pro Thr Cys Val Lys Ser Glu Met Gly Pro Trp
                515                 520                 525

Met Asp Ser Tyr Ser Gly Pro Tyr Gly Asp Met Arg Asn Thr Arg Arg
                530                 535                 540

Lys Arg Leu Trp Lys Leu Ile Ile Arg Ser Ile Asn Ser Cys Ile Cys
545                 550                 555                 560

Ser Pro Arg Glu Thr Glu Val Pro Val Arg Gln Gln Lys
                565                 570
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 9

```
cagagtcgcg actactacaa cttttcca                                         27
```

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
ccggcctgct aatcaagtca cacatctcga gatgtgtgac ttgattagca ggtttt        57
```

<210> SEQ ID NO 11
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
ccggcaccaa tgtcaactcc aggatctcga gatcctggag ttgacattgg tgttttt       57
```

<210> SEQ ID NO 12
<211> LENGTH: 56
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12

```
ccggcgcgac tactacaact ttccactcga gtggaaagtt gtagtagtcg cguttt        56
```

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
tgtaatagtg gttaccactc ttcaagagag agtggtaacc actattactt tttttc        57
```

<210> SEQ ID NO 14
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
tcgagaaaaa aaagtaatag tggttaccac tctctcttga agagtggtaa ccactattac    60
a                                                                    61
```

<210> SEQ ID NO 15
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
taggctaatg aggtrtattt ctcaagagaa ataaacctca ttagccttt tttttc         56

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcgagaaaaa aaaaggctaa tgaggtttat tttccttgag aaataaacct cattagccta    60

<210> SEQ ID NO 17
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
taagaaacag tccgactcaa ttcaagagat tgagtcggac tgtttctttc tttttc        57

<210> SEQ ID NO 18
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcgagaaaaa agaaagaaac agtccgactc aatctcttga attgagtcgg actgtttctt    60
a                                                                    61

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctatggcgc tgagattgtg                                                20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttaatgtgc ccgtccttgt                                                20

<210> SEQ ID NO 21
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 21
gctatccagg ctgtgctatc                                              20

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgtcacgcac gatttcc                                                 17

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccacagagca cctcagcagt cc                                           22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gagcagggca ccctctcatg g                                            21

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctcctcact gacggacttg tctg                                         24

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccctggtga cagatggcc                                               19

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
cacattgcgc atagctgcag aag                                           23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acagacctac tctggaggaa c                                             21

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagacagcaa cccttttt                                                 19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctcattatca ggtctatca                                                19

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctactccgga ccttacgggg acatgcg                                       27

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctttcttcgg gtatttcgca tgtc                                          24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgcatttga gagaagccac gctg						24

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5

<210> SEQ ID NO 35
<211> LENGTH: 2430
<212> TYPE: DNA
<213> ORGANISM: Homo sapiens

<400> SEQUENCE: 35

| | |
|---|---|
| gacactgaat ttggaaggtg gaggattttg ttttttttctt ttaagatctg ggcatctttt | 60 |
| gaatctaccc ttcaagtatt aagagacaga ctgtgagcct agcagggcag atcttgtcca | 120 |
| ccgtgtgtct tcttctgcac gagactttga ggctgtcaga gcgcttttg cgtggttgct | 180 |
| cccgcaagtt tccttctctg gagcttcccg caggtgggca gctagctgca gcgactaccg | 240 |
| catcatcaca gcctgttgaa ctcttctgag caagagaagg ggaggcgggg taagggaagt | 300 |
| aggtggaaga ttcagccaag ctcaaggatg gaagtgcagt tagggctggg aagggtctac | 360 |
| cctcggccgc cgtccaagac ctaccgagga gctttccaga atctgttcca gagcgtgcgc | 420 |
| gaagtgatcc agaacccggg ccccaggcac ccagaggccg cgagcgcagc acctcccggc | 480 |
| gccagtttgc tgctgcagca gcagcagcag cagcagcagc agcagcagca gcagcagcag | 540 |
| cagcagcagc agcagcagca gcagcagcag cagcagcaag agactagccc caggcagcag | 600 |
| cagcagcagc agggtgagga tggttctccc caagcccatc gtagaggccc acaggctac | 660 |
| ctggtcctgg atgaggaaca gcaaccttca cagccgcagt cggccctgga gtgccacccc | 720 |
| gagagaggtt gcgtcccaga gcctggagcc gccgtggccg ccagcaaggg gctgccgcag | 780 |
| cagctgccag cacctccgga cgaggatgac tcagctgccc catccacgtt gtccctgctg | 840 |
| ggccccactt tccccggctt aagcagctgc tccgctgacc ttaaagacat cctgagcgag | 900 |
| gccagcacca tgcaactcct tcagcaacag cagcaggaag cagtatccga aggcagcagc | 960 |
| agcgggagag cgagggaggc ctcgggggct cccacttcct ccaaggacaa ttacttaggg | 1020 |
| ggcacttcga ccatttctga caaccgcaag gagttgtgta aggcagtgtc ggtgtccatg | 1080 |
| ggcctgggtg tggaggcgtt ggagcatctg agtccagggg aacagcttcg ggggattgc | 1140 |
| atgtacgccc cacttttggg agttccaccc gctgtgcgtc ccactccttg tgccccattg | 1200 |
| gccgaatgca aaggttctct gctagacgac agcgcaggca gagcactga agatactgct | 1260 |
| gagtattccc ctttcaaggg aggttacacc aaagggctag aaggcgagag cctaggctgc | 1320 |
| tctggcagcg ctgcagcagg gagctccggg acacttgaac tgccgtctac cctgtctctc | 1380 |
| tacaagtccg gagcactgga cgaggcagct gcgtaccaga gtcgcgacta ctacaacttt | 1440 |
| ccactggctc tggccggacc gccgcccccct ccgccgcctc cccatcccca cgctcgcatc | 1500 |
| aagctggaga acccgctgga ctacggcagc gcctgggcgg ctgcggcggc gcagtgccgc | 1560 |

```
tatggggacc tggcgagcct gcatggcgcg ggtgcagcgg gacccggttc tgggtcaccc    1620
tcagccgccg cttcctcatc ctggcacact ctcttcacag ccgaagaagg ccagttgtat    1680
ggaccgtgtg gtggtggtgg gggtggtggc ggcggcggcg gcgcggcgg cggcggcggc     1740 ggcggcgagg cgggagctgt agcccccta ggctacactc ggcccctca ggggctggcg     1800 ggccaggaaa gcgacttcac cgcacctgat gtgtggtacc ctggcggcat ggtgagcaga    1860
gtgccctatc ccagtcccac ttgtgtcaaa agcgaaatgg gcccctggat ggatagctac    1920
tccggacctt acggggacat gcgtttggag actgccaggg accatgtttt gcccattgac    1980
tattactttc cacccagaa gacctgcctg atctgtggag atgaagcttc tgggtgtcac     2040
tatggagctc tcacatgtgg aagctgcaag gtcttcttca aaagagccgc tgaagggaaa    2100
cagaagtacc tgtgcgccag cagaaatgat tgcactattg ataaattccg aaggaaaaat    2160
tgtccatctt gtcgtcttcg gaaatgttat gaagcaggga tgactctggg agcagctgtt    2220
gttgtttctg aaagaatctt gagggtgttt ggagtctcag aatggcttcc ttaaagacta    2280
ccttcagact ctcagctgct catccacaac agagatcagc ccttctttgt agatgattca    2340
ttcctggctg catttgaaaa ccacatattg ttaattgctt gacgaattta aatcccttga    2400 ctactttca tttcaaaaaa aaaaaaaaaa                                      2430

<210> SEQ ID NO 36
<211> LENGTH: 2893
<212> TYPE: DNA
<213> ORGANISM: Homo sapiens

<400> SEQUENCE: 36
gacactgaat ttggaaggtg gaggattttg ttttttttctt ttaagatctg ggcatctttt    60
gaatctaccc ttcaagtatt aagagacaga ctgtgagcct agcagggcag atcttgtcca    120
ccgtgtgtct tcttctgcac gagactttga ggctgtcaga gcgcttttg cgtggttgct     180 cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaaggatg gaagtgcagt tagggctggg aagggtctac    360
cctcggccgc cgtccaagac ctaccgagga gctttccaga atctgttcca gagcgtgcgc    420
gaagtgatcc agaacccggg ccccaggcac ccagaggccg cgagcgcagc acctcccggc    480
gccagtttgc tgctgcagca gcagcagcag cagcagcagc agcagcagca gcagcagcag    540
cagcagcagc agcagcagca gcagcagcag cagcagcaag agactagccc caggcagcag    600
cagcagcagc agggtgagga tggttctccc caagcccatc gtagaggccc cacaggctac    660
ctggtcctgg atgaggaaca gcaaccttca cagccgcagt cggccctgga gtgccacccc    720
gagagaggtt gcgtcccaga gcctggagcc gccgtggccg ccagcaaggg gctgccgcag    780
cagctgccag cacctccgga cgaggatgac tcagctgccc catccacgtt gtccctgctg    840
ggccccactt tccccggctt aagcagctgc tccgctgacc ttaaagacat cctgagcgag    900
gccagcacca tgcaactcct tcagcaacag cagcaggaag cagtatccga aggcagcagc    960
agcgggagag cgaggaggc ctcggggggct cccacttcct ccaaggacaa ttacttaggg    1020
ggcacttcga ccatttctga caacgccaag gagttgtgta aggcagtgtc ggtgtccatg    1080
ggcctgggtg tggagcgtt ggagcatctg agtccagggg aacagcttcg gggggattgc    1140
atgtacgccc cactttttggg agttccaccc gctgtgcgtc ccactccttg tgccccattg    1200
gccgaatgca aaggttctct gctagacgac agcgcaggca agagcactga agatactgct    1260
```

-continued

```
gagtattccc ctttcaaggg aggttacacc aaagggctag aaggcgagag cctaggctgc    1320
tctggcagcg ctgcagcagg gagctccggg acacttgaac tgccgtctac cctgtctctc    1380
tacaagtccg gagcactgga cgaggcagct gcgtaccaga gtcgcgacta ctacaacttt    1440
ccactggctc tggccggacc gccgcccct ccgccgcctc cccatcccca cgctcgcatc     1500
aagctggaga acccgctgga ctacggcagc gcctgggcgg ctgcggcggc gcagtgccgc    1560
tatgggacc tggcgagcct gcatggcgcg ggtgcagcgg gacccggttc tgggtcaccc     1620
tcagccgccg cttcctcatc ctggcacact ctcttcacag ccgaagaagg ccagttgtat    1680
ggaccgtgtg gtggtggtgg gggtggtggc ggcggcggcg gcggcggcgg cggcggcggc    1740
ggcggcgagg cgggagctgt agccccctac ggctacactc ggccccctca ggggctggcg    1800
ggccaggaaa gcgacttcac cgcacctgat gtgtggtacc ctggcggcat ggtgagcaga    1860
gtgccctatc ccagtcccac ttgtgtcaaa agcgaaatgg cccctggat ggatagctac     1920
tccggacctt acggggacat gcgtttggag actgccaggg accatgtttt gcccattgac    1980
tattactttc caccccagaa gacctgcctg atctgtggag atgaagcttc tgggtgtcac    2040
tatggagctc tcacatgtgg aagctgcaag gtcttcttca aaagagccgc tgaagggaaa    2100
cagaagtacc tgtgcgccag cagaaatgat tgcactattg ataaattccg aaggaaaaat    2160
tgtccatctt gtcgtcttcg gaaatgttat gaagcaggga ttctgggagc agctgttgtt    2220
gtttctgaaa gaatcttgag ggtgtttgga gtctcagaat ggcttcctta agactacct    2280
tcagactctc agctgctcat ccacaacaga gatcagcctt tctttgtaga tgattcattc    2340
ctggctgcat ttgaaaacca catattgtta attgcttgac gaatttaaat cccttgacta    2400
cttttcattt cagaaaacac ttacaaaaaa agtccaaatg aggaccttcc ctccagtgaa    2460
ttagctgtgg ctttctcaca gtccatagtt aggataaatg taaagccatt tctcattttt    2520
ctccgcactt tccaagggta cactccttgt ttccaagatg gaatgagaaa taaagaagtg    2580
ccccttcccca aacatgattc atttctgcgt tttgcaactc ttgagttctc agcatttagt    2640
aaatggtgtt ggtccctgtt gattccttcc tctcctggac catggaaggt agtaggcctt    2700
tcagaaattt caggtagcag ccaaaccca gaagaagaga aggaacacag agacctagac    2760
catgtgagaa cctgaggtgt gcagcattta cttcacagat tcgtctagca tatttgagag    2820
gtgtctttcc tactaggaga ctgaactctg catctgagaa taaaaactta acatatcaaa    2880
aaaaaaaaaa aaa                                                      2893
```

<210> SEQ ID NO 37
<211> LENGTH: 647
<212> TYPE: PRT
<213> ORGANISM: Homo sapiens

<400> SEQUENCE: 37

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80
```

```
Gln Gln Gln Gln Glu Thr Ser Pro Arg Gln Gln Gln Gln Gly
                85                  90              95

Glu Asp Gly Ser Pro Gln Ala His Arg Arg Gly Pro Thr Gly Tyr Leu
            100                 105                 110

Val Leu Asp Glu Glu Gln Pro Ser Gln Pro Gln Ser Ala Leu Glu
        115                 120                 125

Cys His Pro Glu Arg Gly Cys Val Pro Glu Pro Gly Ala Ala Val Ala
    130                 135                 140

Ala Ser Lys Gly Leu Pro Gln Gln Leu Pro Ala Pro Pro Asp Glu Asp
145                 150                 155                 160

Asp Ser Ala Ala Pro Ser Thr Leu Ser Leu Leu Gly Pro Thr Phe Pro
                165                 170                 175

Gly Leu Ser Ser Cys Ser Ala Asp Leu Lys Asp Ile Leu Ser Glu Ala
            180                 185                 190

Ser Thr Met Gln Leu Leu Gln Gln Gln Gln Glu Ala Val Ser Glu
        195                 200                 205

Gly Ser Ser Ser Gly Arg Ala Arg Glu Ala Ser Gly Ala Pro Thr Ser
    210                 215                 220

Ser Lys Asp Asn Tyr Leu Gly Gly Thr Ser Thr Ile Ser Asp Asn Ala
225                 230                 235                 240

Lys Glu Leu Cys Lys Ala Val Ser Val Ser Met Gly Leu Gly Val Glu
                245                 250                 255

Ala Leu Glu His Leu Ser Pro Gly Glu Gln Leu Arg Gly Asp Cys Met
            260                 265                 270

Tyr Ala Pro Leu Leu Gly Val Pro Pro Ala Val Arg Pro Thr Pro Cys
        275                 280                 285

Ala Pro Leu Ala Glu Cys Lys Gly Ser Leu Leu Asp Asp Ser Ala Gly
    290                 295                 300

Lys Ser Thr Glu Asp Thr Ala Glu Tyr Ser Pro Phe Lys Gly Gly Tyr
305                 310                 315                 320

Thr Lys Gly Leu Glu Gly Glu Ser Leu Gly Cys Ser Gly Ser Ala Ala
                325                 330                 335

Ala Gly Ser Ser Gly Thr Leu Glu Leu Pro Ser Thr Leu Ser Leu Tyr
            340                 345                 350

Lys Ser Gly Ala Leu Asp Glu Ala Ala Ala Tyr Gln Ser Arg Asp Tyr
        355                 360                 365

Tyr Asn Phe Pro Leu Ala Leu Ala Gly Pro Pro Pro Pro Pro Pro Pro
    370                 375                 380

Pro His Pro His Ala Arg Ile Lys Leu Glu Asn Pro Leu Asp Tyr Gly
385                 390                 395                 400

Ser Ala Trp Ala Ala Ala Ala Gln Cys Arg Tyr Gly Asp Leu Ala
                405                 410                 415

Ser Leu His Gly Ala Gly Ala Ala Gly Pro Gly Ser Gly Ser Pro Ser
            420                 425                 430

Ala Ala Ala Ser Ser Ser Trp His Thr Leu Phe Thr Ala Glu Glu Gly
        435                 440                 445

Gln Leu Tyr Gly Pro Cys Gly Gly Gly Gly Gly Gly Gly Gly
    450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495
```

```
Phe Thr Ala Pro Asp Val Trp Tyr Pro Gly Gly Met Val Ser Arg Val
                500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
        530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
610                 615                 620

Ile Leu Gly Ala Ala Val Val Val Ser Glu Arg Ile Leu Arg Val Phe
625                 630                 635                 640

Gly Val Ser Glu Trp Leu Pro
                645

<210> SEQ ID NO 38
<211> LENGTH: 2427
<212> TYPE: DNA
<213> ORGANISM: Homo sapiens

<400> SEQUENCE: 38
gacactgaat tggaaggtg gaggattttg ttttttctt ttaagatctg ggcatctttt      60
gaatctaccc ttcaagtatt aagagacaga ctgtgagcct agcagggcag atcttgtcca   120
ccgtgtgtct tcttctgcac gagactttga ggctgtcaga gcgcttttg cgtggttgct   180 cccgcaagtt tccttctctg gagcttcccg caggtgggca gctagctgca gcgactaccg   240
catcatcaca gcctgttgaa ctcttctgag caagagaagg ggaggcgggg taagggaagt   300
aggtggaaga ttcagccaag ctcaaggatg gaagtgcagt tagggctggg aagggtctac   360
cctcggccgc cgtccaagac ctaccgagga gctttccaga atctgttcca gagcgtgcgc   420
gaagtgatcc agaaccccgg gccccaggca ccagaggccg cgagcgcagc acctcccggc   480
gccagtttgc tgctgcagca gcagcagcag cagcagcagc agcagcagca gcagcagcag   540
cagcagcagc agcagcagca gcagcagcag cagcagcaag agactagccc caggcagcag   600
cagcagcagc agggtgagga tggttctccc caagcccatc gtagaggccc acaggctac    660 ctggtcctgg atgaggaaca gcaaccttca cagccgcagt cggccctgga gtgccacccc   720
gagagaggtt gcgtcccaga gcctggagcc gccgtggccg ccagcaaggg gctgccgcag   780
cagctgccag cacctccgga cgaggatgac tcagctgccc catccacgtt gtccctgctg   840
ggccccactt tccccggctt aagcagctgc tccgctgacc ttaaagacat cctgagcgag   900
gccagcacca tgcaactcct tcagcaacag cagcaggaag cagtatccga aggcagcagc   960
agcgggagag cgaggcaggc ctcggggggct cccacttcct ccaaggacaa ttacttaggg  1020
ggcacttcga ccatttctga caacgccaag gagttgtgta aggcagtgtc ggtgtccatg  1080
ggcctgggtg tggagcgctt ggagcatctg agtccagggg aacagctccg ggggattgc   1140 atgtacgccc cactttttggg agttccaccc gctgtgcgtc ccactccttg tgcccattg   1200 gccgaatgca aaggttctct gctagacgac agcgcaggca gagcactga agatactgct  1260
```

```
gagtattccc ctttcaaggg aggttacacc aaagggctag aaggcgagag cctaggctgc    1320
tctggcagcg ctgcagcagg gagctccggg acacttgaac tgccgtctac cctgtctctc    1380
tacaagtccg gagcactgga cgaggcagct gcgtaccaga gtcgcgacta ctacaacttt    1440
ccactggctc tggccggacc gccgccccct ccgccgcctc cccatcccca cgctcgcatc    1500
aagctggaga acccgctgga ctacggcagc gcctgggcgg ctgcggcggc gcagtgccgc    1560
tatggggacc tggcgagcct gcatggcgcg ggtgcagcgg gacccggttc tgggtcaccc    1620
tcagccgccg cttcctcatc ctggcacact ctcttcacag ccgaagaagg ccagttgtat    1680
ggaccgtgtg gtggtggtgg gggtggtggc ggcggcggcg gcggcggcgg cggcggcggc    1740
ggcggcgagg cgggagctgt agcccectac ggctacactc ggccccctca ggggctggcg    1800
ggccaggaaa gcgacttcac cgcacctgat gtgtggtacc ctggcggcat ggtgagcaga    1860
gtgccctatc ccagtcccac ttgtgtcaaa agcgaaatgg gccctggat ggatagctac     1920 tccggaccct acggggacat gcgtttggag actgccaggg accatgtttt gcccattgac    1980
tattactttc caccccagaa gacctgcctg atctgtggag atgaagcttc tgggtgtcac    2040
tatggagctc tcacatgtgg aagctgcaag gtcttcttca aaagagccgc tgaagggaaa    2100
cagaagtacc tgtgcgccag cagaaatgat tgcactattg ataaattccg aaggaaaaat    2160
tgtccatctt gtcgtcttcg gaaatgttat gaagcaggga ttctgggagc agctgttgtt    2220
gtttctgaaa gaatcttgag ggtgtttgga gtctcagaat ggcttcctta aagactacct    2280
tcagactctc agctgctcat ccacaacaga gatcagccct tctttgtaga tgattcattc    2340
ctggctgcat ttgaaaacca catattgtta attgcttgac gaatttaaat cccttgacta    2400
cttttcattt caaaaaaaaa aaaaaaa                                        2427
```

HUMAN ANDROGEN RECEPTOR ALTERNATIVE SPLICE VARIANTS

CROSS-REFERENCE TO RELATED APPLICATIONS

This application is a continuation-in-part of U.S. application Ser. No. 12/562,031, filed Sep. 17, 2009, now U.S. Pat. No. 8,133,724 which claims the benefit of provisional U.S. patent application No. 61/097,571, filed Sep. 17, 2008. The contents of both of the aforesaid applications are relied upon and hereby incorporated by reference in their entirety.

STATEMENT REGARDING FEDERALLY SPONSORED RESEARCH

This invention was made with government support under Grant Number CA106504 awarded by the National Institutes of Health. The government has certain rights in the invention.

BACKGROUND OF THE INVENTION

1. Field of the Invention

The present invention concerns at least the fields of cell biology, molecular biology and medicine. In particular aspects, the present invention concerns the fields of treatment and/or prevention of prostate cancer.

2. Related Art

Prostate cancer is the most commonly diagnosed malignancy in males in the United States and the second leading cause of male cancer mortality. In the event that surgery and/or radiation do not cure prostate cancer, systemic therapy is based on inhibiting the androgen receptor (AR). The androgen receptor is a steroid receptor transcription factor which promotes the growth and survival of normal and cancerous prostate cells. Androgen ablation is used to block the activation or activity of androgens initially and results in a favorable clinical response. However, prostate cancer invariably occurs in a manifestation which is fatal and is resistant to androgen ablation. This stage of prostate cancer is termed androgen refractory prostate cancer.

Prostate cancer is the second leading cause of cancer death among men in western countries. Patients with advanced prostate cancer initially benefit from androgen ablation therapy which leads to temporary remission of the tumor due to apoptosis of androgen-sensitive tumor cells. However, the recurrence of androgen independent tumors is inevitable for most patients and renders the conventional hormone therapy ineffective (Denmeade, S. R. et al., Nat Rev Cancer 2, 389-96 (2002)). It has, therefore, become a focus of intensive study to understand the mechanisms underlying progression of hormone refractory prostate cancer (Litvinov, I. V., et al., Prostate 61, 299-304 (2004); Feldman, B et al., Nat Rev Cancer 1, 34-45 (2001); and Debes, J. D. et al., N Engl J Med 351, 1488-90 (2004)). Development of new effective therapeutic agents is necessary for targeting hormone refractory prostate cancer. As prostate cancer is a product of slow but continuous accumulation of altered genes and proteins controlling several signaling pathways it thus poses a difficult task for identification of precise markers to predict high risk for recurrence. Validation of tumor progression markers are an essential component for prostate cancer treatment strategies to plan for appropriate therapy based on its level, tissue distribution and the stage or extent of the disease.

Identification and characterization of the molecular mechanisms and biological switches which propel normal prostate cells into cells in the cancerous state is critical for developing therapeutic modalities which can be used to prevent and/or treat male subjects predisposed to prostate cancer.

Increasing clinical findings demonstrate that a majority of androgen ablation therapy-resistant prostate cancers still express AR and androgen-dependent genes, indicating that the AR-signaling pathway is functional in the absence of androgens or in the presence of low levels of androgens (Chang, C. S. et al., Science 240, 324-6 (1988); Lubahn, D. B. et al., Mol Endocrinol 2, 1265-75 (1988)). Several independent studies also showed that AR is essential for both hormone sensitive and recurrent hormone refractory prostate cancer (McPhaul, M. J. et al., J Investig Dermatol Symp Proc 8, 1-5 (2003); Heinlein, C. A. et al., Endocr Rev 25, 276-308 (2004)). The mechanisms underlying androgen-independent activation of AR have yet to be fully understood. Mutations and amplification of AR, alterations in protein kinases, growth factors and nuclear receptor coactivators have all been proposed to modulate AR signaling and may, therefore, play key roles in the development of androgen independence of prostate cancer (Feldman, B. et al., Nat Rev Cancer 1, 34-45 (2001); Lubahn, D. B. et al. Mol Endocrinol 2, 1265-75 (1988); Kuiper, G. G. et al., J Mol Endocrinol 2, R1-4 (1989)). Mutations in the ligand binding domain of AR are shown to broaden the ligand binding profile of the mutant receptor (Lubahn, D. B. et al., Proc Natl Acad Sci USA 86, 9534-8 (1989); Libertini, S. J. et al., Cancer Res 67, 900 1-5 (2007); Simental, J. A., et al., J Biol Chem 266, 5 10-8 (1991)). However, the frequency of AR mutation is generally low and probably only accounts for less than 10% of the cases surveyed (Jenster, G. et al. Mol Endocrinol 5, 1396-404 (1991)). Upregulation of the enzymes involving in steroid synthesis in some recurrent prostate tumors and activation of AR via the intracrine mechanism have also been reported (Rundlett, S. E. et al., Mol Endocrinol 4, 708-14 (1990)). However, the tissue androgen level did not correlate with clinical prognosis. Recently, the increased AR expression level is shown to associate with the development of resistance to anti-androgen therapy (McPhaul, M. J. et al., J Investig Dermatol Symp Proc 8, 1-5 (2003)). The cross-talk between growth factor and AR signaling pathways in prostate cancer cells has been well documented. The expression of several peptide growth factors, such as EGF/TGFa, IL-6 and IGF-1, are reported to be elevated during progression to hormone refractory human prostate cancer (Bolton, E. C. et al., Genes Dev 21, 2005-17 (2007); Wang, Q. et al., Mol Cell 27, 3 80-92 (2007); Clegg, N. et al. J Steroid Biochem Mol Biol 80, 13-23 (2002); DePrimo, S. E. et al., Genome Biol 3, RESEARCH0032 (2002); Marcelli, M. et al., J Clin Endocrinol Metab 84, 3463-8 (1999); Comuzzi, B. et al., Am J Pathol 162, 233-41 (2003); Chen, C. D. et al., Nat Med 10, 33-9 (2004)). These autocrine/paracrine factors can either induce the androgen-independent activation of AR transcriptional activity or sensitize AR to low concentrations of androgens (Lubahn, D. B. et al., Mol Endocrinol 2, 1265-75 (1988); Zegarra-Moro, O. L., et al., Cancer Res 62, 1008-13 (2002); Culig, Z. et al., Endocr Relat Cancer 9, 155-70 (2002)). Several protein kinases, including MAPK, Akt/PKB, PICA and PKC, Src and Ack-1 have been shown to modulate AR transcriptional activity by phosphorylating AR or its coactivators such as TIF2 and SRC1 (Zegarra-Moro, O. L., et al., Cancer Res 62, 1008-13 (2002); Culig, Z., et al., Endocr Relat Cancer 9, 155-70 (2002); Gelmann, E. P. et al., J Clin Oncol 20, 3001-15 (2002); Mizokami, A. et al., Cancer Res 64, 765-71 (2004); Kurita, T. et al., Cell Death Differ 8, 192-200 (2001); Veldscholte, J. et al., Biochem Biophys Res Commun 173, 534-40 (1990); Taplin, M.-E. et al., J Clin Oncol 21, 2673-2678 (2003)). Another plausible hypothesis for activation of androgen receptor activity in the absence of hormones was proposed by Tepper et al. who showed that a mutant AR identified in hormone refractory prostate cancer cell line CWR22Rv1 contains an in-frame tandem duplication of exon 3 that encodes the second zinc finger of the AR DNA-binding domain (Paez, J. G. et al., Science 304, 1497-1500 (2004)). This insertional mutation renders AR susceptible to the protease cleavage at the hinge region and generates a constitutively active form around 80 kD. A recent study also showed that calpain may mediate cleavage of the AR mutant in this cell line (Yeh, S. et al., Proc Natl Acad Sci USA 96, 5458-63 (1999)). However, the frequency of such insertional mutation has only been detected in CWR22R xenograft derived cell line CWR22Rv1. It remains elusive whether it is a general mechanism underlying androgen-independence.

We have cloned novel AR splice variants (AR3, AR4, AR4b, AR5 and AR8) from hormone refractory CWR22Rv1 xenografts. All the variants contain the intact N-terminal transactivation domain and the DNA binding domain, but lack the ligand binding domain, and therefore, are true androgen-independent. AR3 appears to be constitutively active in ARE-mediated transcription. We confirmed the expression of these AR variants in human prostate tumors by RT-PCR and/or immunohistochemistry. Knocking-down AR3, one of the major AR variants in hormone refractory prostate cancer cells, attenuated androgen-independent growth in both cell culture and xenograft models. Our data suggest that the AR variants resulted from alternative splicing may be a novel mechanism underlying androgen-independence during prostate cancer progression. These novel AR variants are not inhibited by currently available anti-androgen drugs (such as casodex) due to the lack of the ligand binding domain. Therefore new drugs targeting at these novel AR variants may potentially be more effective for androgen-independent prostate tumors. Further characterization of these AR variants will provide new insights into mechanisms underlying androgen-independence and identify new therapeutic targets. Detection of the expression of these AR variants may be potentially used as a prognostic marker for prostate cancer and targeting these variants may develop more effective treatment for androgen-independent prostate cancer.

BRIEF SUMMARY OF THE INVENTION

Example embodiments are generally directed to novel androgen receptor splice variants designated as AR3, AR4, AR4b, AR5 and AR8. These novel androgen receptor splice variants can play an important role in the progression of androgen independent progression of prostate cancer. These androgen-independent receptors contain the N-terminal transactivation domain and the DNA binding domain but lack the ligand binding domain.

In other embodiments, these splice variants can serve as prognostic markers (biomarkers) to determine the degree of the disease and predict outcome in response to hormonal therapy.

In other embodiments, these novel androgen receptor splice variants represent targets for therapeutics/drugs which can be used to treat human subjects diagnosed with prostate cancer. In particular, these embodiments cover a variety of methodologies which can be used to modulate these novel androgen receptors, including but not limited to: antisense technology, natural and/or synthetic compounds or peptides/proteins, RNAi, ribozymes and antibody technology.

A first aspect of the invention provides novel, isolated androgen receptor (AR) nucleic acids and polypeptides that are not available in the art.

More specifically, isolated nucleic acid molecules are provided encoding AR3, AR4, AR4b, AR5 and AR8 and variants and fragments thereof. Vectors, host cells and recombinant methods for producing the same are also provided.

Another aspect of the invention relates to isolated AR3, AR4, AR4b, AR5 and AR8 polypeptides and variants and fragments thereof and methods for their production.

Another aspect of the invention relates to methods for using AR3, AR4, AR4b, AR5 and AR8 polynucleotides and polypeptides. Such uses include assays for screening agents that modulate either the expression or protein activity of AR3, AR4, AR4b, AR5 or AR8, among others.

Another aspect of the invention relates to diagnostic assays and kits for the detection of diseases associated with AR3, AR4, AR4b, AR5 or AR8 expression levels or protein activity associated with neoplastic disorders, such as androgen refractory prostate cancer.

Another aspect of the invention relates to methods for detecting androgen refractory prostate cancer in an animal comprising assaying an androgen receptor splice variant expression level in the animal and comparing the androgen receptor splice variant expression level with a standard androgen receptor splice variant expression level.

Another aspect of the invention relates to pharmaceutical compositions comprising a therapeutically effective agent which regulates expression of AR3, AR4, AR4b, AR5 or AR8.

Another aspect of the invention relates to isolated antisense nucleic acids that are sufficiently complimentary to the nucleic acid sequence of AR3, AR4, AR4b, AR5 or AR8 to permit hybridization under physiologic conditions, and which antisense nucleic acid inhibits expression of the androgen receptor.

Another aspect of the invention relates to methods for altering expression of the androgen receptor splice variants AR3, AR4, AR4b, AR5 or AR8 in a prostate cancer cell comprising delivering agents to the cell which increase or decrease the stability of mRNA coding for AR3, AR4, AR5 or AR8.

Another aspect of the invention relates to methods of treating or preventing androgen refractory prostate cancer in a patient in need thereof, comprising administering to the patient an effective amount of an agent that inhibits the function of an androgen receptor splice variant selected from the group consisting of AR3, AR4, AR4b, AR5 and AR8.

Another aspect of the invention relates to methods for treating cancer in an animal comprising administering to the animal an isolated short interfering RNA molecule that inhibits expression of the androgen receptor splice variant AR3, AR4, AR4b, AR5, or AR8.

Another aspect of the invention relates to methods for inhibiting the activity of androgen splice receptor variants AR3, AR4, AR4b, AR5 or AR8 in a prostate cancer cell comprising administering to said cell an antibody or functional fragment of the antibody which binds the androgen receptor.

Another aspect of the invention relates to a screening system for detecting compounds which bind to nucleic acids encoding AR3, AR4, AR4b, AR5 or AR8, thereby inhibiting expression of the androgen receptor.

Another aspect of the invention relates to transgenic animals or their progeny or parts thereof, which comprises in their genome a transgene construct comprising a polynucleotide encoding an androgen receptor splice variant selected from the group consisting of AR3, AR4, AR4b, AR5 and AR8.

Such transgenic animals are useful as animal models for androgen refractory prostate cancer, among other uses.

BRIEF DESCRIPTION OF THE FIGURES

Embodiments of the invention are herein described, by way of non-limiting example, with reference to the following accompanying Figures:

FIGS. 3A-D: Increased AR3 expression in hormone refractory prostate tumor cells. (A) Total cell lysates of a panel of prostate cancer cells were blotted with anti-AR3 and anti-Actin antibodies, respectively. (B) The human prostate tissue microarrays were stained with anti-AR3 antibody. The mean score of cytoplasmic and nuclear staining of the luminal cell as well as the positive rates for cytoplasmic and nuclear staining were shown. (Error bars indicate standard error, $*p<0.01$). Benign prostate tissue ("B"), hormone naïve ("HN") and hormone refractory ("HR"). (c) The representative fields of the tissue arrays stained with anti-AR3. The anti-AR stained arrays were included as a control. (d) Correlation of AR3 cytoplasmic staining with PSA recurrence after prostatectomy.

FIGS. 4A-D: AR3 promotes androgen-independent growth of prostate cancer cells. LNCaP cells were infected with lentivirus encoding AR3 expression construct (AR3) or the control vector. After 2-week culture in androgen-depleted condition, the cells were visualized by Coomassie Blue staining (A). At 48 hr post infection, the cells were injected into the castrated SCID mice and the growth of the tumor cells were monitored weekly. The result represent the mean tumor volume±SE (n=5 mice/group), $*p<0.05$ Inset, Western blots of anti-AR3 and anti-AR of the LNCaP xenograft tumor lysates (B). CWR-R1 and 22Rv1 cells were infected with lentivirus encoding AR3 shRNA-1 (shAR3) or control shRNA (shCon). After 2 weeks culture in androgen-depleted condition, the cells were visualized by Coomassie Blue staining (C). At 48 hr postinfection, the cells were injected into the castrated male nude mice. The growth of the tumors was monitored weekly. The result represents the mean tumor volume±SE (n=5 mice/group), $*p<0.05$ (D). Inset, Western blots of anti-AR3 and anti-AR of the CWR-R1 and 22Rv1 xenograft tumor lysates.

FIGS. 9A-B. Specificity of the anti-AR3 antibody.

FIG. 10. IHC staining of AR3 in human prostate tissues.

FIGS. 11A-B. AR3 full-length cDNA sequence (SEQ ID NO:1) and protein sequence (SEQ ID NO:5).

FIGS. 12A-B. Putative AR4 full length cDNA sequence (SEQ ID NO:2) and protein sequence (SEQ ID NO:6).

FIGS. 13A-C. Putative AR5 full length cDNA sequence (SEQ ID NO:3) and protein sequence (SEQ ID NO:7).

FIGS. 14A-C. The panels depict information relating to the generation and analysis of an AR3 transgenic (AR3Tg) mouse.

FIG. 15. Histological analysis of tissue sections revealed that the AR3Tg displayed extensive hyperplasia in all three lobes.

FIGS. 18A-B. Elevated MAPK and Akt pathways in AR3Tg prostate determined by Western blot with anti-phosphoMAPK and pan anti-phospho AKT-substrates antibodies, respectively.

FIG. 19. A partial list of genes regulated by AR3 in mouse prostate.

FIG. 20. The level of mature TGF-β monomers (doublet suggesting at least two members of TGF-β family may be processed in prostate) was dramatically elevated in AR3Tg prostate compared to the WT control. As a result, both SMAD1 and SMAD3 phosphorylation is elevated.

FIG. 21. The number of Sca-1 and cc6 integrin double positive cells was increased at least two fold to 35% in AR3Tg prostates compared to 16% in the WT littermate controls.

FIG. 22. The prostatic cells from the AR3Tg mouse appeared to form more spheres than those from the WT littermate controls and AR3 transgene is highly expressed in the basal compartment of the sphere. 6-week-old AR3Tg or WT control prostates were dissected and minced, followed by digestion with collagenase for 90 min. Dissociated cells were then be run through a BD FACSVantage Cell Sorter to remove cell doublets and small clusters. The isolated single cells were counted and suspended in Matrigel/PrGEM(1:1), then seeded in triplicate at final densities of 1250, 2500, 5000 and 10,000 cells per well in 12-well plates. At 14-day post-plating, prostatic spheres with a diameter greater than 40 um were counted and photographed (Top). The prostatic spheres were fixed and embedded in paraffin and sectioned with the microtome at 3 μm thickness. IHC staining with antibody for AR3 were performed (Bottom).

FIGS. 24A-B. Association of AR and AR splicing isoforms with mitochondria. (A) COS-1 cells were transfected with AR4 expression construct. At 24 h post transfection, cells were labeled with mitotracker dye (Invitrogen) for 30 min at 37° C. to show the mitochondria (red) and followed with the immunofluorescence staining with anti-AR (green). (B) CWR-R1 cells were infected with AR shRNAs. At 48 hr post infection, the cytoplasmic (Cyto) and mitochondrial (Mito) fractions of the CWR-R1 cells were prepared by using a mitochondria isolation kit (Pierce) and subjected to westernblot with anti-AR and anti-Bcl-xL. The latter was served as a mitochondria marker.

FIGS. 26A-B. AR8 amino acid sequence (SEQ ID NO:8). AR8 is primarily present on the plasma membrane when overexpressed (FIG. 26B). Identification of two Cysteine residues (C558 &569) in the C-terminal unique sequence as potential palmitoylation sites (underlined in FIG. 26A). Substitution of these two Cys with Ala residues dramatically diminished plasma membrane targeting of AR8 (FIG. 26B).

FIGS. 27A-B. The real-time PCR analysis revealed that AR8 expression is elevated in hormone resistant CWR22R xenografts (HR) compared to hormone sensitive counterpart (HS) (FIG. 27A) and AR8 level is also increased in hormone resistant LNCaP derivatives C4-2 and C4-2B compared to hormone sensitive parental LNCaP cells (FIG. 27B). Total RNA was isolated from hormone sensitive (HS), hormone resistant CWR22 xenografts, or prostate cancer cell lines, and then subjected to reverse transcription-PCR. The primers used to amplify AR8 are (sense 5'-CTACTCCGGACCT-TACGGGGACATGCG-3'(SEQ ID NO:31) and antisense 5'-CTTTCTTCGGGTATTTCGCATGTC-3' (SEQ ID NO:32)). The total cell lysates from these cells were subjected to immunoblotting with anti-AR (right panel). The position of AR8 is marked by an arrow.

FIGS. 29A-B. AR8 knock-down inhibits proliferation (FIG. 29A) and increases of apoptosis in CWR-R1 cells (FIG. 29B). CWR-R1 cells were plated on coverslips and infected with lenti-virus encoding shAR8 or the vector control in androgen-depleted medium. At 48 h post-infection, the cell proliferation was evaluated by the ClickiT™ EdU Assay (Invitrogen). CWR-R1 cells were infected with lenti-virus encoding specific shAR8 or the vector control in androgen-depleted medium. At 48 h post-infection, the apoptosis was detected by TUNEL assays.

DETAILED DESCRIPTION OF THE INVENTION

Figure 1:
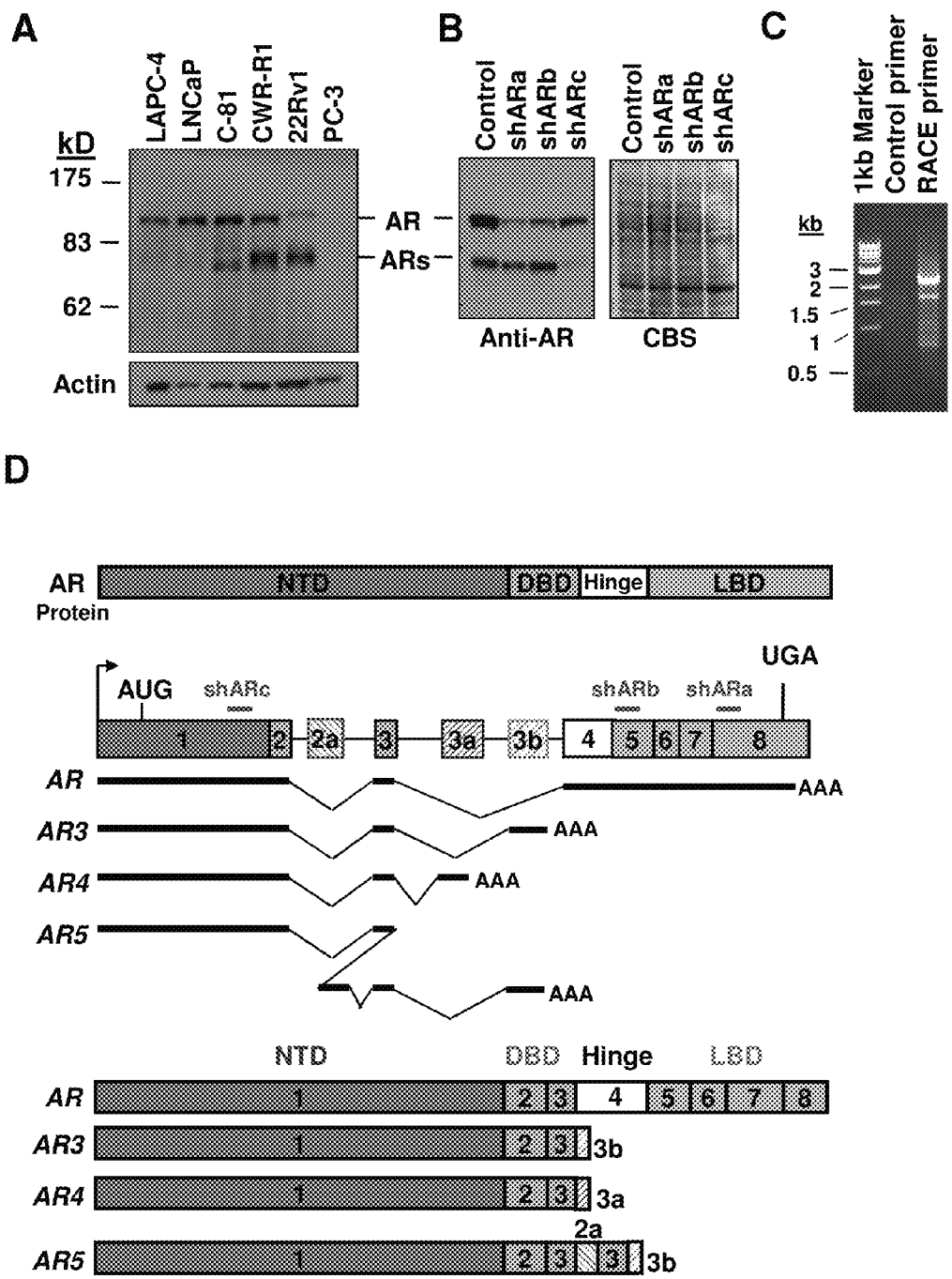
FIGS. 1A-H: Cloning of novel alternative splice AR isoforms. (A) Presence of the short forms of AR in prostate cancer cells. Total cell lysates of different prostate cancer cells were blotted with anti-AR (441) antibody (upper) and anti-Actin antibody (lower). (B) Selective knockdown of AR long/short forms by AR shRNAs. CWR-R1 cells were infected with the lentivirus encoding AR shRNAa, AR shRNAb, and AR shRNAc (shARa, shARb and shARc) targeting different exons of AR as indicated in (D). At 48 hr post infection, the total cell lysates were subjected to western blot with anti-AR antibody. The same blot was stained with Coomassie Blue to show the protein loading (right panel). (C) Presence of AR isoform transcripts in CWR-R1 cells. Total RNA was isolated from CWR-R1 cells and reverse transcribed. The primer derived from AR shRNAc sequence was used to perform a rapid amplification of cDNA 3'-end (3'-RACE) with the RACE oligo-dT primer or a control primer. (D) Schematic structure of the human AR splice variants. The hatched cassettes stand for the cryptic exons. Solid thick lines represent the transcribed sequences. (E) Expression of AR isoforms in prostate cancer cells. The relative expression levels of AR, AR3, AR4 and AR5 were quantified using real-time PCR with the isoform specific primer pair sets described in Methods (left panel). The AR level in LNCaP cells was arbitrarily set as 1. The expression levels of AR3 in LNCaP and C-8 1 cells were further plotted with a higher resolution. $*p<0.05$ (right panel). (F) Transcriptional activity of AR isoforms. COS-1 cells were transfected with ARR.2-luciferase reporter gene together with AR, AR3, AR4 and AR5 expression vector. At 24 hr posttransfection, the cells were lysed and the luciferase activity was measured. The data were expressed as relative promoter activity, the changes of luciferase activity relative to the untreated control (arbitrarily set as 1). (G) COS-1 cells were transfected with ARR2-Luciferase reporter along with increasing doses of AR3 or AR expressing vector. At 24 hr posttransfection, the cells were treated with or without 10 nM DHT for 24 hr and the luciferase activities were then measured. (H) LNCaP cells were infected with (+) or without (−) the lentivirus encoding AR shRNA (shAR) as described previously. At 6 hr postinfection, the cells were transfected with ARR2-Luciferase reporter along with AR3 or the codon-switched wild-type AR expressing vector (ARcs). At 24 hr posttransfection, the cells were treated with DHT and casodex (CAS) as indicated for 24 hr before the luciferase activity was measured.
Figure 1:
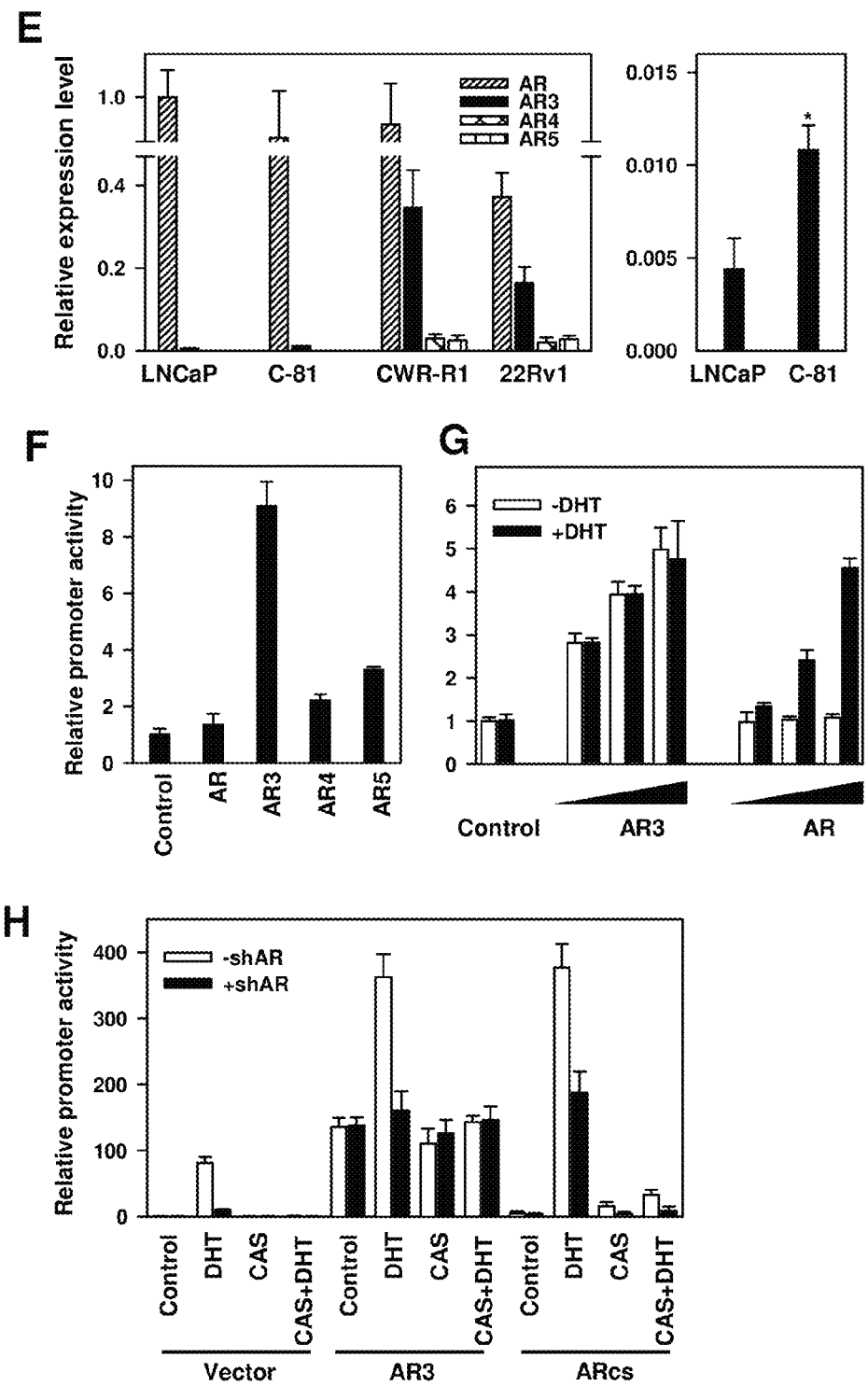

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials now described.

One skilled in the art may refer to general reference texts for detailed descriptions of known techniques discussed herein or equivalent techniques. These texts include Current Protocols in Molecular Biology (Ausubel et. al., eds. John Wiley & Sons, N.Y. and supplements thereto), Current Protocols in Immunology (Coligan et al., eds., John Wiley St Sons, N.Y. and supplements thereto), Current Protocols in Pharmacology (Enna et al., eds. John Wiley & Sons, N.Y. and supplements thereto) and Remington: The Science and Practice of Pharmacy (Lippincott Williams & Wilicins, 2Vtedition (2005)) for example.

As discussed above and herein, the present invention relates to novel alternatively spliced variants of human androgen receptor as biomarkers and therapeutic targets. The novel splice variants of the androgen receptor (AR), AR3, AR4, and AR5 and AR8 are herein described.

As used herein, unless otherwise indicated by a specific nucleotide SEQ ID NO, "AR3," "AR4," "AR4b," "AR5," and "AR8" also include transcripts that arise through the use of alternative polyadenylation signals.

AR4b (SEQ ID NOS:36-38) differs from AR4 in that it lacks a threonine residue in the carboxy-terminal region as compared with AR4 (SEQ ID NO:2 and 6), and is likely a product resulting from usage of alternative splice donor or acceptor sequences.

These novel AR splice variants are expressed in hormone refractory prostate cancer cells and may contribute to their androgen independence.

These AR variants contain the intact N-terminal transactivation domain, and the DNA binding domain but lack the ligand binding domain. AR3 is one of the major splice variants expressed in human prostate tissues. AR3 is constitutively active and its transcriptional activity is not regulated by androgens or antiandrogens. The data collected would indicate that AR3 is significantly upregulated during prostate cancer progression and the AR3 expression level is correlated with the risk of tumor recurrence after a prostatectomy. Thus, AR3 has a putative important role in the development of androgen-independence of prostate cancer. AR4 comprises two transcripts of different size, depending on differential usage of a 3' polyadenylation signal. The longer version is indicated by SEQ ID NO:2 and the shorter version is indicated by SEQ ID NO:35. AR4b also gives rise to transcripts using the same polyadenylation signals, and is indicated by SEQ ID NO:36 and 38.

Accordingly, certain embodiments of the present invention relate to various methods for identifying potential cancerous prostate tissues using the spliced androgen receptor variants as biomarkers. Additionally, certain embodiments of the present invention relate to various therapeutic modalities targeted to the spliced androgen receptor variants.

Certain other embodiments of the present invention relate to various methods of diagnosis, prophylactic treatment and therapeutic treatment of prostate cancer predicated on the features of these novel androgen receptor splice variants.

Providing a therapy or "treating" refers to indicia of success in the treatment or amelioration of an injury, pathology or condition, including any objective or subjective parameter such as abatement, remission, diminishing of symptoms of making the injury, pathology or condition more tolerable to the patient, slowing the rate of degeneration or decline, making the final point of degeneration less debilitating, or improving a patient's physical or mental well-being. Those in need of treatment include those already with the disease (prostate cancer) as well as those prone to have the disorder those in whom the disorder is to be prevented. Preferred subject for treatment include animals, most preferably mammalian species, such as humans and domestic animals such as dogs, cats, and the like, subject to disease and other pathological conditions. A "patient" refers to a subject, preferably mammalian (including human).

As used herein, a "biological sample", or simply "sample" where the context is clear, is any substance that is derived from a subject or patient including, but not limited to, a bodily fluid (such as blood, urine, saliva, spinal fluid), cells (e.g., a biopsy of cells from the prostate), tissue, organ, or other matter taken or obtained from a subject or patient.

Protein Activity or Biological Activity of the Protein: These expressions refer to the metabolic or physiologic function of the androgen receptor splice variant proteins including similar activities or improved activities or these activities with decreased undesirable side-effects. Also included are antigenic and immunogenic activities of said androgen receptor splice variant protein. Among the physiological or metabolic activities of said protein is the transcription of androgen receptor responsive target genes, binding of coactivators, DNA or other transcription factors and repressors. Androgen independent transcriptional activation is also included.

Androgen receptor splice variant polynucleotides: This term refers to a polynucleotide containing a nucleotide sequence that encodes androgen receptor splice variant polypeptides or fragments thereof, or variants that encodes an androgen receptor splice variant polypeptide or fragment thereof or variant, wherein said nucleotide sequence has at least 90% identity to a nucleotide sequence encoding the polypeptide of SEQ ID NOS:5-8 or 37 or a corresponding fragment thereof, or which has sufficient identity to a nucleotide sequence contained in SEQ ID NOS:1-4, 35, 36 and 38.

Androgen receptor splice variant polypeptides: This term refers to polypeptides with amino acid sequences sufficiently similar to the androgen receptor splice variant protein sequences in SEQ ID NOS:5-8 or 37 and wherein at least one biological activity of the protein is exhibited.

I. Pharmaceutical Compositions and Methods

Certain embodiments of the present invention relate to pharmaceutical compositions comprising one or more therapeutic agents, and methods of administering a therapeutically effective amount of one or more therapeutic agents, which are capable of prophylactic and/or therapeutic treatment of prostate cancer and related conditions. The term "therapeutic agent" refers to any pharmaceutically acceptable acid, salt, ester, derivative, a stereoisomer, pro-drug or mixtures of stereoisomers of a therapeutic agent or to the therapeutic agent itself. Pharmaceutically acceptable acids, salts, esters, derivatives, stereoisomers, pro-drugs, and mixtures of therapeutic agents may also be used in the methods and compositions of the present invention. The therapeutic agents can include agents which downregulate the transcriptional level and/or protein level of the androgen receptor splice variants including AR3, AR4, AR4b, AR5 and AR8, agents which modulate the interaction between the androgen receptor splice variants including AR3, AR4, AR4b, AR5 and AR8 with their cofactors, such as coactivator proteins or DNA response elements, and agents which modulate posttranslational modification of the androgen receptor splice variants including AR3, AR4, AR4b, AR5 and AR8.

The pharmaceutical compositions can be formulated according to known methods for preparing pharmaceutically acceptable useful compositions, and may include a pharmaceutically acceptable carrier. The carrier may be liquid, solid, or semi-solid for example. Formulations are described in a number of sources which are well known to those of skill in the art. The physical and/or chemical characteristics of compositions of the inventions may be modified or optimized according to skill in the art, depending on the mode of administration and the particular disease or order to be treated. The compositions may be in any suitable form, depending on the desired method of administration, and may be provided in unit dosage form, a sealed container, or as part of a kit, which may include instructions for use and/or a plurality of unit dosage forms.

A carrier molecule may also be used in place, of or in conjunction with, the pharmaceutically acceptable carriers described herein. Suitable carrier molecules include, for example, a micelle, a liposome (e.g., a cationic liposome), a nanoparticle, a microsphere, or a biodegradable polymer. As used herein, a nanoparticle refers to a particle having a size of less than about 1,000 nanometers. In particular aspects, the nanoparticles will have a diameter of about 50 to about 120 nm, such as from about 50 to about 100 nm, from about 50 to about 70 nm, or even about 50 nm. Therapeutic agents are attached to the surface of the nanoparticle, or entangled or embedded in nanoparticle, especially where the nanoparticle has a matrix-type structure. Nanoparticles include particles capable of containing a therapeutic agent that is to be released within a mammalian body, including specialized forms such as nanospheres, whether natural or artificial. Peptide-based therapeutic agents can be tethered to a nanoparticle by a variety of linkages, such as a disulfide linkage, an acid labile linkage, a peptide-based linkage, an oxyamino linkage or a hydrazine linkage. For example, a peptide-based linkage can be a GFLG peptide. Conjugation of nucleic acid molecules to nanoparticles can be accomplished by methods known in the art, e.g., using the methods of Lambert et al., *Drug Deliv. Rev.* 47(1): 99-112 (2001), Fattal et al., *J. Control Release* 53(1-3):137-43 (1998), Schwab et al., *Ann. Oncol.* 5 Suppl. 4:55-8 (1994), and Godard et al., *Eur. J. Biochem.* 232(2):404-10 (1995), each of which is incorporated herein by reference it its entirety. Linkages may be cleavable or non-cleavable.

The term "pharmaceutically acceptable" used herein refers to those modifications of the parent compound (acids, salts, ester, etc.) that do not significantly or adversely affect the pharmaceutical properties of the parent compound. For example, exemplary pharmaceutically acceptable salts administrable by means of the compositions of this invention include chloride, bromide, iodide, hydrochloride, acetate, nitrate, stearate, palmoate, phosphate, and sulfate salts. Exemplary techniques for producing pharmaceutically acceptable derivatives include for example, methylation, halogenation, acetylation, esterification and hydroxylation.

The term "therapeutically effective amount" means the total amount of each active component of the pharmaceutical composition or method that is sufficient to show meaningful patient benefits, i.e, a decrease in the prostate tumor size or metastatic potential of the tumor, an increase in patient survival time, sensitization of patients to other therapeutic agents including but not limited to chemotherapy and hormonal therapy.

The pharmaceutical composition may be adapted for administration by any appropriate route, for example by the oral, rectal, nasal, topical, vaginal or parenteral routes. Other routes, e.g., intra-articular, may also be used. Such compositions may be prepared by any known method, for example by admixing the active ingredient with the carrier(s) or excipient(s) under sterile conditions.

Pharmaceutical compositions adapted for oral administration may be presented as discrete units such as capsules or tablets; as powders or granules, as solutions, syrups or suspensions. Suitable excipients for tablets or hard gelatine capsules include lactose, maize starch, or derivative thereof, stearic acids or salts thereof. Suitable excipients for use with soft gelatine capsules include for example vegetable oils, waxes, fats, semi-solid, or liquid polyols etc. For the preparation of solutions and syrups, excipients which may be used include for example water, polyols, and sugars. For the preparation of suspension, oils (e.g., vegetable oils) may be used to provide oil-in-water or water-in-oil suspensions. In certain situations, delayed release or enteric-coated preparations may be advantageous, for example to decrease gastric residence time and thereby reduce degradation of the pharmaceutical composition en route to the lower GI tract.

Pharmaceutical compositions adapted for rectal administration may be presented as suppositories or enemas. Pharmaceutical compositions adapted for nasal administration wherein the carrier is a solid include a coarse powder having a particle size ranging from about 20 to about 500 microns. Suitable compositions wherein the carrier is a liquid for administration as a nasal spray or as nasal drops, include aqueous or oil solution of the active ingredient. Pharmaceutical compositions adapted for administration by inhalation include fine particle dusts or mists which may be generated by means of various types of metered dose pressurized aerosols, nebulizer or insufflators.

Pharmaceutical compositions adapted for topical administration may be formulated as ointments, creams, suspensions, lotions, powders, solutions, pastes, gels, sprays, aerosols, or oils. When formulated in an ointment, the therapeutic agent may be employed with either a parafinninic or a water-miscible ointment base. Pharmaceutical compositions adapted from topical administration to the eye include eye drops wherein the therapeutic agent is dissolved or suspended in a suitable carrier, especially an aqueous solvent. Pharmaceutical compositions adapted for topical administration in the mouth include lozenges, pastilles, and mouth washes. Pharmaceutical compositions adapted for transdermal administration may be presented as discrete patches intended to remain in intimate contact with the epidermis of the recipient for a prolonged period of time. Pharmaceutical compositions adapted for vaginal administration may be presented as pessaries, tampons, creams, gels, pastes, foams, or spray formulations.

Pharmaceutical compositions adapted for parenteral administration include aqueous and non-aqueous sterile injection solutions which may contain anti-oxidants, buffers, bacteriostats, and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in freeze-dried conditions requiring only the addition of a sterile liquid immediately prior to use. Extemporaneous injection solutions and suspensions may be prepared from sterile powders, granules, and tablets. The pharmaceutical compositions may contain preserving agents, solubilizing agents, stabilizing agents, wetting agents, emulsifiers, sweeteners, colorants, salts, buffers, antioxidants, etc.

The administration of the compositions of the present invention may be for a "prophylactic" or "therapeutic" purpose, or alternatively can be used for diagnostic purposes. The compositions of the present invention are said to be administered for a "therapeutic" purpose if the amount administered is physiologically significant to provide a therapy for an actual manifestation of the disease. When provided therapeutically, the compound is preferably provided at (or shortly after) the identification of a symptom of actual disease. The therapeutic administration of the compound serves to attenuate the severity of such disease or to reverse its progress. The compositions of the present invention are said to be administered to provide a therapy for a potential disease or condition. When provided prophylactically, the compound is preferably provided in advance of any symptom thereof. The prophylactic administration of the compound serves to prevent or attenuate any subsequent advance of the disease.

II. Polynucleotides of the Invention

In some embodiments, the invention provides polynucleotides encoding androgen receptor splice variant polypeptides having the amino acid sequence set out in SEQ ID NO:5, SEQ ID NO:6, SEQ ID NO:7, SEQ ID NO:8, SEQ ID NO:37 and variants and fragments thereof.

A particular nucleotide sequence encoding an androgen receptor splice variant polypeptide may be identical over its entire length to the coding sequence in SEQ ID NOs:1, 2, 3, 4, 35, 36, or 38. Alternatively, a particular nucleotide sequence encoding a androgen receptor splice variant polypeptide may be an alternate form of SEQ ID NOs:1, 2, 3, 4, 35, 36, or 38 due to degeneracy in the genetic code or variation in codon usage encoding the polypeptides of SEQ ID NOs:5, 6, 7, 8 or 37. In some embodiments, the polynucleotides of the invention contain a nucleotide sequence that is highly identical, at least 90% identical, with a nucleotide sequence encoding an androgen receptor splice variant polypeptide or at least 90% identical with the encoding nucleotide sequence set forth in SEQ ID NOs:1, 2, 3, 4, 35, 36, or 38.

When a polynucleotide of the invention is used for the recombinant production of an androgen receptor splice variant polypeptide, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. For example, a marker sequence that facilitates purification of the fused polypeptide can be encoded. In certain embodiments of this aspect of the invention, the marker sequence is a hexa-histidine peptide (SEQ ID NO:34), as provided in the pQE vector (Qiagen, Inc.) and described in Gentz et al., Proc Natl Acad Sci USA 86:821-824 (1989), or it may be the HA tag, which corresponds to an epitope derived from the influenza hemagglutinin protein (Wilson, I., et al., Cell 37:767, 1984). The polynucleotide may also contain non-coding 5' and 3' sequences, such as transcribed, non-translated sequences, splicing and polyadenylation signals, ribosome binding sites and sequences that stabilize mRNA.

Embodiments of the invention include isolated nucleic acid molecules comprising a polynucleotide having a nucleotide sequence at least 90% identical, and more preferably at least 91%, 92%, 93%, 94%, 95%, 96%, 97%, 98% 99% or 100% identical to (a) a nucleotide sequence encoding an androgen receptor splice variant polypeptide having the amino acid sequence in SEQ ID NO:5, SEQ ID NO:6, SEQ ID NO:7, SEQ ID NO:8 or SEQ ID NO:37; or (b) a nucleotide sequence complementary to the nucleotide sequences in (a).

Conventional means utilizing known computer programs such as the BestFit program (Wisconsin Sequence Analysis Package, Version 10 for Unix, Genetics Computer Group, University Research Park, 575 Science Drive, Madison, Wis. 53711) may be utilized to determine if a particular nucleic acid molecule is at least 90%, 91%, 92%, 93%, 94%, 95%, 96%, 97%, 98% or 99% identical to any one of the nucleotide sequences shown in SEQ ID NO:1, SEQ ID NO:2, SEQ ID NO:3, SEQ ID NO:4, SEQ ID NO:35, SEQ ID NO:36, or SEQ ID NO:38.

In some embodiments, the polynucleotides encode an androgen receptor splice variant polypeptide have an amino acid sequence of the androgen receptor splice variant polypeptides of SEQ ID NO:5, SEQ ID NO:6, SEQ ID NO:7, SEQ ID NO:8 or SEQ ID NO:37, in which several, 1, 2, 3, 4, 5, 6, 7, 8, 9, 10 or more amino acid residues are substituted, deleted or added, in any combination.

In some embodiments, the polynucleotides are at least 90% identical over their entire length to a polynucleotide encoding an androgen receptor splice variant polypeptide having the amino acid sequence set out in SEQ ID NO:5, SEQ ID NO:6, SEQ ID NO:7, SEQ ID NO:8 or SEQ ID NO:37, and polynucleotides which are complementary to such polynucleotides. In some embodiments, the polynucleotides are at least 95% identical over their entire length, at least 97% identical, at least 98% identical, or at least 99% identical.

The present invention is further directed to fragments of SEQ ID NOs:1, 2, 3, 4, 35, 36 and 38. A fragment may be defined to be at least about 15 nt, and more preferably at least about 20 nt, still more preferably at least about 30 nt, and even more preferably, at least about 40 nt in length. Such fragments are useful as diagnostic probes and primers as discussed herein and can be incorporated into detection kits to detect the androgen receptor splice variants in biological samples. Of course larger DNA fragments are also useful according to the present invention, as are fragments corresponding to most, if not all, of the nucleotide sequence of SEQ ID NO:1, SEQ ID NO:2, SEQ ID NO:3, SEQ ID NO:4, SEQ ID NO:35, SEQ ID NO:36 or SEQ ID NO:38. In some embodiments, the fragments can be at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 510, 520, 530, 540, 550, 560, 570, 580, 590, 600, 620, 640, 660, 680, 700, 720, 740, 760, 780, 800, 820, 840, 860, 880, 900, 920, 940, 960, 980 or 1000 nucleotides. In one embodiment, the fragment comprises the final 200, 190, 180, 170, 160, 150, 140, 130, 120, 110, 100, 90, 80, 70, 60, 50, 40, 30, 20 or 10 nucleotides of the coding region of a polynucleotide encoding an androgen receptor splice variant polypeptide having the amino acid sequence set out in SEQ ID NO:5, SEQ ID NO:6, SEQ ID NO:7, SEQ ID NO:8 or SEQ ID NO:37. In another embodiment, the fragment comprises the final 200, 190, 180, 170, 160, 150, 140, 130, 120, 110, 100, 90, 80, 70, 60, 50, 40, 30, 20 or 10 nucleotides of the coding region of the polynucleotide of SEQ ID NO:1, 2, 3, 4, 35, 36, or 38.

The present invention further relates to polynucleotides that hybridize to the above-described sequences. In this regard, the present invention especially relates to polynucleotides that hybridize under stringent conditions to the above-described polynucleotides. As herein used, the term "stringent conditions" means hybridization will occur only if there is at least 90% and preferably at least 95% identity and more preferably at least 97% identity between the sequences.

Furthermore, a major consideration associated with hybridization analysis of DNA or RNA sequences is the degree of relatedness the probe has with the sequences present in the specimen under study. This is important with a blotting technique (e.g., Southern or Northern Blot), since a moderate degree of sequence homology under nonstringent conditions of hybridization can yield a strong signal even though the probe and sequences in the sample represent non-homologous genes.

The particular hybridization technique is not essential to the invention, any technique commonly used in the art is within the scope of the present invention. Typical probe technology is described in U.S. Pat. No. 4,358,535 to Falkow et al., incorporated by reference herein. For example, hybridization can be carried out in a solution containing 6×SSC (10×SSC: 1.5 M sodium chloride, 0.15 M sodium citrate, pH 7.0), 5×Denhardt's (1×Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C. Additionally, if hybridization is to an immobilized nucleic acid, a washing step may be utilized wherein probe binding to polynucleotides of low homology, or nonspecific binding of the probe, may be removed. For example, a stringent wash step may involve a buffer of 0.2.times.SSC and 0.5% SDS at a temperature of 65° C.

Additional information related to hybridization technology and, more particularly, the stringency of hybridization and washing conditions may be found in Sambrook et al., Molecular Cloning: A Laboratory Manual, Second Edition, Cold Spring Harbor Laboratory, Cold Spring Harbor, N.Y. (1989), which is incorporated herein by reference.

Polynucleotides of the invention which are sufficiently identical to a nucleotide sequences contained in SEQ ID NO:1, SEQ ID NO:2, SEQ ID NO:3, SEQ ID NO:4, SEQ ID NO:35, SEQ ID NO:36 or SEQ ID NO:38 may be used as hybridization probes for cDNA and genomic DNA, to isolate full-length cDNAs and/or genomic clones encoding androgen receptor splice variant proteins and to isolate cDNA and genomic clones of other DNA that has a high sequence similarity to the androgen receptor splice variants. Such hybridization techniques are known to those of skill in the art. Typically, these nucleotide sequences are at least about 90% identical, preferably at least about 95% identical, more preferably at least about 97%, 98% or 99% identical to that of the reference. The probes generally will comprise at least 15 nucleotides. Preferably, such probes will have at least 30 nucleotides and may have at least 50 nucleotides. In some embodiments, the probes will range between 30 and 50 nucleotides. In some embodiments, the probes will be at least about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 510, 520, 530, 540, 550, 560, 570, 580, 590, 600, 620, 640, 660, 680, 700, 720, 740, 760, 780, 800, 820, 840, 860, 880, 900, 920, 940, 960, 980 or 1000 nucleotides. In one embodiment, the probes comprises the final 200, 190, 180, 170, 160, 150, 140, 130, 120, 110, 100, 90, 80, 70, 60, 50, 40, 30, 20 or 10 nucleotides of the coding region of a polynucleotide encoding an androgen receptor splice variant polypeptide having the amino acid sequence set out in SEQ ID NO:5, SEQ ID NO:6, SEQ ID NO:7, SEQ ID NO:8 or SEQ ID NO:37. In another embodiment, the probes comprises the final 200, 190, 180, 170, 160, 150, 140, 130, 120, 110, 100, 90, 80, 70, 60, 50, 40, 30, 20 or 10 nucleotides of the coding region of the polynucleotide of SEQ ID NO:1, 2, 3, 4, 35, 36, or 38.

In other embodiments, the invention provides polynucleotide sequence that has promoter activity, operatively linked, in a transcriptional unit, to a DNA sequence encoding a protein of interest. In one embodiment, the DNA sequence encodes a protein of interest selected from the group consisting of SEQ ID NO:5, 6, 7, 8 or 37 and variants and fragments thereof. In some embodiments, the DNA sequence encodes a polypeptide fragment or variant of SEQ ID NO:5, 6, 7, 8 or 37 that possesses wild-type protein activity. In other embodiments, the DNA sequence encodes a polypeptide fragment or variant of SEQ ID NO:5, 6, 7, 8 or 37 that is a null mutant, or a dominant negative mutant that inhibits endogenous androgen receptor splice variant activity. In some embodiments, the promoter is tissue specific for the prostate. In some embodiments, the promoter is constitutively active, and is not selective to a particular tissue. In other embodiments, the promoter is inducible, using methods known in the art.

III. Vectors, Host Cells, and Recombinant Expression

The present invention also relates to vectors that comprise a polynucleotide of the present invention, including cloning vectors and expression vectors, host cells which are genetically engineered with vectors of the invention and methods for the production of polypeptides of the invention by recombinant techniques. Cell-free translation systems can also be employed to produce such proteins using RNAs derived from the DNA constructs of the invention.

Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells. A great variety of expression systems can be used, including DNA or RNA vectors.

In other embodiments, this invention provides an isolated nucleic acid molecule comprising an androgen receptor splice variant operably linked to a heterologous promoter. This invention further provides an isolated nucleic acid molecule comprising and androgen receptor splice variant operably linked to a heterologous promoter, wherein said isolated nucleic acid molecule is capable of expressing an androgen receptor splice variant polypeptide when used to transform an appropriate host cell.

Methods for the production of polypeptides of the invention including culturing a host cells transfected with one or more of the vectors of the present invention under conditions promoting expression of the polypeptide encoded by the vector, and isolating the polypeptide so expressed from the cell culture.

IV. Polypeptides of the Invention

The androgen receptor splice variant polypeptides of the present invention include the polypeptide of SEQ ID NO:5, SEQ ID NO:6, SEQ ID NO:7, SEQ ID NO:8, and SEQ ID NO:37 as well as polypeptides and fragments which have activity and have at least 90% identity to the polypeptide of SEQ ID NO:5, SEQ ID NO:6, SEQ ID NO:7, SEQ ID NO:8 or SEQ ID NO:37. Dominant negative mutants and null mutants of SEQ ID NOS:5-8 or 37 are also included. In some embodiments, the polypeptides have at least 96%, 97% or 98% identity to the polypeptide of SEQ ID NO:5, SEQ ID NO:6, SEQ ID NO:7, SEQ ID NO:8 or SEQ ID NO:37. In some embodiments, the polypeptides have at least 91%, 92%, 93%, 94%, 95%, 96%, 97%, 98%, 99%, or 100% identity to the polypeptide of SEQ ID NO:5, SEQ ID NO:6, SEQ ID NO:7, SEQ ID NO:8 or SEQ ID NO:37.

The androgen receptor splice variant polypeptides may be a part of a larger protein such as a fusion protein. It is often advantageous to include additional amino acid sequence which contains secretory or leader sequences, pro-sequences, sequences which aid in purification such as multiple histidine residues, or additional sequence for stability during recombinant production.

Biologically active fragments of the androgen receptor splice variant polypeptides are also included in the invention. A fragment is a polypeptide having an amino acid sequence that entirely is the same as part but not all of the amino acid sequence of one of the aforementioned androgen receptor splice variant polypeptides. As with androgen receptor splice variant polypeptides, fragments may be "free-standing," or comprised within a larger polypeptide of which they form a part or region, most preferably as a single continuous region. In the context of this invention, a fragment may constitute from about 10 contiguous amino acids identified in SEQ ID NO:5, SEQ ID NO:6, SEQ ID NO:7, SEQ ID NO:8 or SEQ ID NO:37. In some embodiments, the fragment is about 20, 30, 40, 50, 60, 70, 80, 90, 100, 110, 120, 130, 140, 150, 160, 170, 180, 190, 200, 210, 220, 230, 240 or 250, 260, 270, 280, 290, 300, 310, 320, 330, 340, 350, 360, 370, 380, 390, 400, 410, 420, 430, 440, 450, 460, 470, 480, 490 500, 510, 520, 530, 540 contiguous amino acids or more identified in SEQ ID NO:5, SEQ ID NO:6, SEQ ID NO:7, SEQ ID NO:8 or SEQ ID NO:37.

Fragments that lack the biological activity of the androgen receptor splice variant polypeptide from which they are derived are also included within the scope of the invention. In one embodiment, the fragment comprises the final 200, 190, 180, 170, 160, 150, 140, 130, 120, 110, 100, 90, 80, 70, 60, 50, 40, 30, 20 or 10 amino acids of an androgen receptor splice variant polypeptide of SEQ ID NO:5, 6, 7, 8, or 37. In a particular embodiment, the fragment consists of amino acids 530-573, 531-573, 532-573, 533-573, 534-573, 535-573, 536-573, 537-573, 538-573, 539-573, 540-573, 541-573, 542-573, 543-573, 544-573, 545-573, 546-573, 547-573, 548-573, 549-573 or 550-573 of SEQ ID NO:8. Such fragments can be used, for example, in the production of antibodies that specifically bind the splice variants of the invention.

In some embodiments the fragments include, for example, truncation polypeptides having the amino acid sequence of androgen receptor splice variant polypeptides, except for deletion of a continuous series of residues that includes the amino terminus, or a continuous series of residues that includes the carboxyl terminus or deletion of two continuous series of residues, one including the amino terminus and one including the carboxyl terminus. In some embodiments, fragments are characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions, functional domains such as the N-terminal transactivation domain or the DNA binding domain. Biologically active fragments are those that mediate protein activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 90% identical to that of SEQ ID NO:5, SEQ ID NO:6, SEQ ID NO:7, SEQ ID NO:8 or SEQ ID NO:37 or fragments thereof with at least 90% identity to the corresponding fragment of SEQ ID NO:5, SEQ ID NO:6, SEQ ID NO:7, SEQ ID NO:8 or SEQ ID NO:37, all of which retain the biological activity of the androgen receptor splice variant protein, including antigenic activity. Included in this group are variants of the defined sequence and fragment. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which several, 1, 2, 3, 4, 5, 6, 7, 8, 9, 10 or more amino acids are substituted, deleted, or added in any combination.

The androgen receptor splice variant polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

V. Genetic Screening and Diagnostic Assays

As a means to detect or diagnose neoplastic disorders, such as prostate cancer or androgen refractory prostate cancer, differences in the mRNA expression levels (or cDNA) or protein levels or sequence differences of the androgen receptor splice variants between affected and unaffected individuals can be determined. Increased expression of the splice variants disclosed in the present invention in prostate cells is indicative of the presence of androgen refractory prostate cancer. Differences in relative levels between different androgen receptor splice variants can also be determined and compared.

This invention also relates to the use of androgen receptor splice variant polynucleotides or antibodies reactive specifically against the splice variants for use as diagnostic reagents. Detection of altered mRNA (or cDNA) or protein levels of the androgen receptor splice variants will provide a diagnostic tool that can add to or define a diagnosis of a disease or susceptibility to a disease which results from altered expression of the androgen receptor splice variants. The detection of normal or altered expression levels of the androgen receptor splice variants will direct the medical practitioner to set an appropriate course of treatment for the patient.

Nucleic acids for diagnosis may be obtained, for example, from a biopsy of cells from the prostate. In some embodiments, bodily fluids, e.g., urine, are obtained from the patient are used to detect elevated levels of expression. Alterations in expression level can be assayed by comparison to a standard or control expression level of androgen receptor splice variant. RNA may be used directly for detection or may be converted to cDNA and amplified enzymatically by using PCR or other amplification techniques prior to analysis.

The diagnostic assays offer a process for diagnosing or determining a susceptibility to neoplastic disorders through detection of altered expression levels or mutations in one or more androgen receptor splice variants by the methods described. Neoplastic disorders, such as androgen refractory prostate cancer, may be diagnosed by methods that determine an abnormally increased level of androgen receptor splice variant polypeptide or androgen receptor splice variant mRNA in a biological sample derived from a subject. Decreased or increased expression may be measured at the RNA level using any of the methods well known in the art for the quantitation of polynucleotides; for example, RT-PCR, RNase protection, Northern blotting, array analysis, and other hybridization methods may be utilized. In one embodiment, the present invention includes a method of screening a subject for a neoplastic disorder, such as prostate cancer, or a subject at risk for a neoplastic disorder, such as prostate cancer, comprising (a) measuring the expression level of an androgen receptor splice variant in a biological sample from the subject, and (b) comparing the measured level to a reference standard providing the amounts of the splice variant in subjects with and without prostate cancer. In one aspect, the measuring is a measure of the amount of mRNA encoding the androgen receptor splice variant polypeptide. In another embodiment, the present invention includes a method of screening a subject for a neoplastic disorder, such as prostate cancer, or a subject at risk for a neoplastic disorder, such as prostate cancer, comprising (a) measuring the expression levels of two or more androgen receptor splice variants in a biological sample from the subject, and (b) comparing the levels so measured, wherein the relative levels of expression are indicative of whether the subject has a neoplastic disorder. In one aspect, the measuring is a measure of the amount of mRNA encoding androgen receptor splice variant polypeptides, such as splice variants AR4 and AR8.

Assay techniques that may be used to determine the level of a protein, such as an androgen receptor splice variant protein, in a biological sample derived from a host are well known to those of skill in the art. Such assay methods include radioimmunoassays, competitive-binding assays, Western blot analysis and ELISA assays. In one embodiment, the present invention includes a method of screening a subject for a neoplastic disorder, such as prostate cancer, or a subject at risk for a neoplastic disorder, such as prostate cancer, comprising (a) measuring the amount of an androgen receptor splice variant in a biological sample from the subject, and (b) comparing the measured amount to a reference standard providing the amounts of the splice variant in subjects with and without prostate cancer. In one aspect, the measuring is a measure of the amount androgen receptor splice variant polypeptide in the biological sample. In another embodiment, the present invention includes a method of screening a subject for a neoplastic disorder, such as prostate cancer, or a subject at risk for a neoplastic disorder, such as prostate cancer, comprising (a) measuring the amounts of two or more androgen receptor splice variants in a biological sample from the subject, and (b) comparing the amounts so measured, wherein the relative amounts are indicative of whether the subject has a neoplastic disorder. In one aspect, the measuring is a measure of the amount of androgen receptor splice variants polypeptides in the biological sample, such as splice variants AR4 and ARB. The measuring of the amount of a polypeptide may use an antibody that specifically binds to an androgen receptor splice variant of the invention.

Additionally, methods are provided for detecting or determining a susceptibility of an individual to neoplastic disorders, such as prostate cancer or androgen refractory prostate cancer, comprising (a) measuring the expression level of an androgen receptor splice variant in a biological sample of an animal, such as cells or body fluid; and (b) comparing the measured level to a reference standard providing the expression level of the splice variant in subjects with and without a neoplastic disorder, wherein when the measured level is greater than the expression level in a subject without a neoplastic disorder, the subject is determined to be susceptible to develop a neoplastic disorder, such as, for example, prostate cancer or androgen refractory prostate cancer. In another embodiment, methods are provided for detecting or determining a susceptibility of an individual to neoplastic disorders, such as prostate cancer or androgen refractory prostate cancer, comprising (a) measuring the expression levels of two or more androgen receptor splice variant in a biological sample of an animal, such as cells or body fluid; and (b) comparing the levels so measured, wherein the relative levels of expression are indicative of the susceptibility of the individual to neoplastic disorders. In some embodiments, the animal is a mammal, preferably a human. In some embodiments, the androgen receptor splice variant expression level is AR3 (e.g., SEQ ID NO:1), AR4 (e.g., SEQ ID NOS:2 or 35), AR4b (e.g., SEQ ID NO:36 or 38), AR5 (e.g., SEQ ID NO:3) and/or AR8 (e.g., SEQ ID NO:4). The androgen receptor splice variants can be assayed individually or in combination, e.g., as a panel of biomarkers to indicate the presence of androgen refractory prostate cancer. Other prostate cancer markers, such as PCA3, can also be simultaneously assayed, in accordance with the methods of the present invention. In one aspect, the measuring is a measure of the level of mRNA encoding the androgen receptor splice variant polypeptide. In a related aspect, the measuring is a measure of the level of mRNA encoding two or more androgen receptor splice variant polypeptides, such as splice variants AR4 and AR8. In another aspect, the measuring is a measure of the amount androgen receptor splice variant polypeptide in the biological sample. In a related aspect, the measuring is a measure of the amount of two or more androgen receptor splice variants polypeptides in the biological sample, such as splice variants AR4 and AR8. The measuring of the amount of polypeptide may use an antibody that specifically binds to an androgen receptor splice variant of the invention.

VI. Androgen Receptor Splice Variant Antibodies

The invention provides antibodies that specifically bind androgen receptor splice variant polypeptides AR3, AR4, AR4b, AR5 and AR8.

The skilled artisan will understand that the particular attributes of the antibodies of the present invention are only confined in that the antibodies specifically bind one of the splice variants. For example, the antibodies may be polyclonal, monoclonal, humanized or chimeric antibodies, and the antibodies may be in the form of an antiserum comprising the antibodies. The antibodies may be of any class, such as IgG1, IgG2, IgG3, IgG4, IgM, IgA1, IgA2, IgD or IgE. The antibodies may be isolated antibodies, purified antibodies, exogenous antibodies, endogenous antibodies, or a combination thereof. In addition to antibodies that simply bind the splice variants, the antibodies of the present invention include antibodies that act as agonists of splice variant activity upon binding and antibodies that act as antagonists of splice variant activity upon binding.

The antibodies may also be antibody fragments of less than the entire antibody, including, but not limited to, single chain antibodies, F(ab')$_2$ fragments, Fab fragments, and fragments produced by an Fab expression library, with the only limitation being that the antibodies specifically bind a splice variant of the invention. In embodiments where the antibodies act as agonists or antagonists of splice variant activity, the fragments will also maintain such activity. It will be clear to the skilled artisan that all references to "antibodies" herein include both full-size antibodies as well as antibody fragments, as defined herein.

The antibodies may be produced in any species of animal, though preferably from a mammal such as a human, simian, mouse, rat, rabbit, guinea pig, horse, cow, sheep, goat, pig, dog or cat. For example, the antibodies can be human antibodies or humanized antibodies, or any antibody preparation suitable for administration to a human. For the production of the antibodies, the selected species of animal can be immunized by injection with one or more of the polypeptides of the invention or their fragments or analogs thereof, or cells expressing them, as the immunogens to produce antibodies that specifically bind the androgen receptor splice variant polypeptides.

The immunogens may be administered in conjunction with one or more pharmaceutically acceptable adjuvants to increase the immunological response. Suitable adjuvants include, but are not limited to, Freund's Complete and Incomplete Adjuvant, Titermax, Oil in Water Adjuvants, as well as aluminum compounds where immunogens, normally peptides, are physically precipitated with hydrated insoluble salts of aluminum hydroxide or aluminum phosphate. Other adjuvants include liposome-type adjuvants comprising spheres having phospholipid bilayers that form an aqueous compartment containing the immunogen and protect it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the immunogenic formulation.

Means for preparing antibodies are very well known in the art. The antibodies of the invention can be prepared using any known technique that provides for the production of antibody molecules. Suitable techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci. 80:2026-2030 (1983)), and the EBV-hybridoma technique (Cole et al., Monoclonal Antibodies and Cancer Therapy, Alan R. Liss Inc, New York N.Y., pp 77-96 (1985)). Each of these publications is herein incorporated by reference in its entirety. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci. USA* 86: 3833-3837 (1989), and in Winter G. and Milstein C., *Nature* 349:293-299 (1991), both of which is herein incorporated by reference in its entirety.

Humanized antibodies are those where a human antibody has been engineered to contain non-human complementarity-determining regions (CDRs) derived from an antibody produced in a non-human host against a selected antigen. Means for producing humanized antibodies are well-known in the art and include Vaswani S K, and Hamilton R G, *Ann Allergy Asthma Immunol.* 81(2):105-15 (1998) and Kashmiri S V et al., *Methods* 36 (1):25-34 (2005), each of which is herein incorporated by reference in its entirety.

Chimeric antibodies are those where an antigen binding region (e.g., F(ab')$_2$ or hypervariable region) of a non-human antibody is transferred into the framework of a human antibody by recombinant DNA techniques. Techniques developed for the production of such antibodies include the splicing of mouse antibody genes to human antibody genes to obtain a molecule with appropriate antigen specificity and biological activity. Such techniques are also well known and include: Morrison et al., *Proc Natl. Acad. Sci.* 81:6851-6855 (1984); Neuberger et al., *Nature* 312:604-608 (1984); Takeda et al., *Nature* 314:452-454 (1985), each of which is herein incorporated by reference in its entirety.

Techniques for the production of single chain antibodies are described in U.S. Pat. No. 4,946,778, incorporated herein by reference in its entirety.

Antibody fragments such as F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse W. D. et al., Science 256:1275-1281 (1989), herein incorporated by reference in its entirety).

In one aspect of the invention, the antibodies bind to an epitope comprising the final 200, 190, 180, 170, 160, 150, 140, 130, 120, 110, 100, 90, 80, 70, 60, 50, 40, 30, 20 or 10 amino acids of an androgen receptor splice variant polypeptide of SEQ ID NO:5, 6, 7, 8, or 37. In another aspect, the antibodies bind to an epitope comprising amino acids 500-573 of SEQ ID NO:8 or amino acids 540-573 of SEQ ID NO:8. In another aspect, the antibodies bind to an epitope comprising amino acids 530-573, 531-573, 532-573, 533-573, 534-573, 535-573, 536-573, 537-573, 538-573, 539-573, 540-573, 541-573, 542-573, 543-573, 544-573, 545-573, 546-573, 547-573, 548-573, 549-573 or 550-573 of SEQ ID NO:8.

The above-described antibodies maybe employed to isolate or to identify clones expressing the polypeptide or to purify the polypeptides by affinity chromatography.

Antibodies against androgen receptor splice variant polypeptides may also be employed to treat neoplastic disorders, such as prostate cancer or androgen refractory prostate cancer, in a patient in need thereof.

In further embodiments of the invention, kits for use in measuring the amount receptor splice variant polypeptides in a biological sample are included. Such kits comprise one or more antibodies that specifically bind to one or more androgen receptor splice variant polypeptides of the invention. In one aspect is a kit for measuring the amount of an androgen receptor splice variant polypeptide in a biological sample comprising an antibody that specifically binds one of AR3, AR4 or AR8. In another aspect is a kit for measuring the amount of an androgen receptor splice variant polypeptide in a biological sample comprising antibodies that specifically binds two of AR3, AR4 or AR8. In a further aspect is a kit for measuring the amount of an androgen receptor splice variant polypeptide in a biological sample comprising antibodies that specifically binds each of AR3, AR4 and AR8.

VII. Agonist and Antagonist Screening

In some embodiments, the ability of antagonists and agonists of androgen receptor splice variant proteins to interfere or enhance the activity of the androgen receptor splice variant proteins can be evaluated with cells containing the androgen receptor splice variant. In some embodiments of the invention, an assay for androgen receptor splice variant activity in cells can be used to determine the functionality of the androgen receptor splice variant protein in the presence of an agent which may act as antagonist or agonist, and thus, agents that interfere or enhance the activity of androgen receptor splice variants are identified.

In some embodiments, the androgen receptor splice variants of the present invention are employed in a screening process for compounds which bind one of the proteins and which enhance (agonists) or inhibit (antagonists) the transcriptional activation activity of one of the polypeptides of the present invention. Thus, polypeptides of the invention may also be used to assess the binding of molecular substrates and ligands in, for example, cells, cell-free preparations, chemical libraries, and natural product mixtures. These substrates and ligands may be natural substrates and ligands or may be structural or functional mimetics. Antagonists of the androgen receptor splice variants are particularly advantageous and can be used in methods as therapeutic agents in the treatment of prostate cancer, for example, androgen refractory prostate cancer in mammals in need of treatment.

By "agonist" is intended naturally occurring and/or synthetic compounds capable of enhancing transcriptional activity mediated by the androgen receptor splice variants of the invention, or other biological activities of the protein(s). By "antagonist" is intended naturally occurring and/or synthetic compounds capable of inhibiting transcriptional activity mediated by the androgen receptor splice variants of the invention, or other biological activities of the protein(s).

In some embodiments, the screening procedures involve producing appropriate cells which express the polypeptide(s) of the present invention. Such cells include cells from mammals, yeast, *Drosophila* or *E. coli*. In some embodiments, the cells express the polypeptide endogenously. In other embodiments, the cells have been transfected or engineered to express the polypeptide. In some embodiments, cells expressing the protein (or extracts or purified preparations from cells) are contacted with a test compound to observe stimulation or inhibition of a functional response. In some embodiments, one or more androgen receptor response element(s) (ARE) are linked to a reporter gene and activation or inhibition of the reporter gene is assayed. In some embodiments, the expression level of an endogenous androgen receptor target gene is assayed.

In some embodiments, assays test binding of a candidate compound to the androgen receptor splice variants or assays involving competition with a labeled competitor. In some embodiments, inhibitors of activation can be tested in the presence of an agonist and the effect on activation by the agonist in the presence of the candidate compound is observed.

Examples of androgen receptor splice variant protein agonists or antagonists include antibodies, peptides, carbohydrates, vitamin derivatives or small molecules which bind to the protein so that transcriptional activation mediated by the protein is prevented. These agents can be selected and screened 1) at random, 2) by a rational selection or 3) by design using for example, protein or ligand modeling techniques (preferably, computer modeling).

For random screening, agents such as antibodies, peptides, carbohydrates, pharmaceutical agents and the like are selected at random and are assayed for their ability to bind to or stimulate/block the activity of the androgen receptor splice variants.

Alternatively, agents may be rationally selected or designed. As used herein, an agent is said to be "rationally selected or designed" when the agent is chosen based on the configuration of the androgen receptor splice variant protein.

In one aspect, the invention provides a method of screening for an agent which modulates the activity of an androgen receptor splice variant, e.g., an agonist or antagonist, comprising: (a) contacting the androgen receptor splice variant with the agent to be tested; and (b) assaying the agent's effect on the androgen receptor splice variant activity. In some embodiments, the activity to be tested is DNA binding, coactivator binding, binding to other transcription factors, and/or transcriptional activation.

In some embodiments, the agonist or antagonist is assayed to determine whether DNA binding of the androgen receptor splice variants to an androgen receptor response element is affected. In some embodiments, compounds that inhibit DNA binding would function as antagonists and compounds that enhance DNA binding would function as agonists. Such assays can be conducted in vitro, e.g., by electrophoretic mobility shift assays (EMSAs) and can be employed to assay DNA binding of the androgen receptor splice variants. In some embodiments, a method of screening for an antagonist or agonist which stimulates or blocks the DNA binding of the androgen receptor splice variant to DNA is provided, comprising: (a) contacting the androgen receptor splice variant with an agent to be tested and a nucleic acid sequence harboring a region that binds to the androgen receptor splice variant, such as an androgen receptor response element; and (b) assaying binding of the androgen receptor splice variant to the nucleic acid sequence. In some embodiments, auxiliary transcription factors, coactivator proteins, androgen receptor responsive promoter sequence optionally linked to a target or reporter gene, nucleotides, and the like may be added.

In some embodiments, a method of screening for an antagonist or agonist which stimulates or blocks the binding of the androgen receptor splice variant to one or more coactivator proteins is provided, comprising: (a) contacting the androgen receptor splice variant with an agent to be tested and a coactivator protein; and (b) assaying binding of the androgen receptor splice variant to the coactivator protein. Auxiliary transcription factors, coactivators, androgen receptor responsive promoter sequence optionally linked to a target or reporter gene, nucleotides, and the like may be added. Such binding of the androgen receptor splice variants and coactivators can also be verified by EMSAs, provided, however, nucleic acid capable of binding either the coactivator or androgen receptor splice variant is also added.

In some embodiments, the present invention relates to a method of screening for an antagonist or agonist which modulates the activity of the androgen receptor splice variant comprising: (a) contacting a cell expressing the androgen receptor splice variant with an agent to be tested; and (b) assaying expression of a gene mediated by the androgen receptor splice variant. In some embodiments, mRNA levels (or cDNA) is assayed. In other embodiments, protein levels are assayed.

Any cell may be used in the above assay so long as it expresses a functional form of an androgen receptor splice variant and the androgen receptor splice variant activity can be measured. The preferred expression cells are eukaryotic cells or organisms. Such cells can be modified to contain DNA sequences encoding androgen receptor splice variant using routine procedures known in the art. Alternatively, one skilled in the art can introduce mRNA encoding the androgen receptor splice variant protein directly into the cell.

In some embodiments, the assay is carried out in a cell-free system. In some embodiments, a method of screening for an antagonist or agonist which modulates the activity of the androgen receptor splice variant is provided, comprising: (a) contacting a cell-free system comprising the androgen receptor splice variant with an agent to be tested; and (b) assaying expression of a gene mediated by the androgen receptor splice variant. In some embodiments, mRNA levels (or cDNA) is assayed. In other embodiments, protein levels are assayed. Auxiliary transcription factors, coactivator complexes, androgen receptor responsive promoters linked to a target or reporter gene, nucleotides, and the like may be added.

Using androgen receptor splice variant ligands (ligands including antagonists and agonists as described above) the present invention further provides a method for modulating the activity of the androgen receptor splice variant protein in a cell. In general, ligands (antagonists and agonists) which have been identified to block or stimulate the activity of androgen receptor splice variant can be formulated so that the ligand can be contacted with a cell expressing an androgen receptor splice variant protein in vivo. The contacting of such a cell with such a ligand results in the in vivo modulation of the activity of the androgen receptor splice variant proteins. So long as a formulation barrier or toxicity barrier does not exist, ligands identified in the assays described above will be effective for in vivo use.

In another embodiment, the present invention relates to a method of administering androgen receptor splice variant or an androgen receptor splice variant (including androgen receptor splice variant antagonists and agonists) to an animal (preferably, a mammal (specifically, a human)) in an amount sufficient to effect an altered level of androgen receptor splice variant in the animal. The administered androgen receptor splice variant or androgen receptor splice variant ligand could specifically effect androgen receptor splice variant associated functions. Further, since androgen receptor splice variant protein is expressed in prostatic cancer cells, administration of androgen receptor splice variant or androgen receptor splice variant ligand could be used to alter androgen receptor splice variant levels in such cells.

In addition to screening for agonists and antagonists of the protein, the present invention also encompasses a screening system for detecting compounds which bind to the DNA identified by SEQ ID NOS:1, 2, 3, 4, 35, 36, or 38 encoding the androgen receptor splice variants, thereby inhibiting expression of the androgen receptor. In some embodiments, the DNA encoding the androgen receptor is coupled to a reporter system and is a marker for compounds exhibiting regulating properties of expression of the messenger RNA.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of androgen receptor splice variant or androgen receptor splice variant ligand, in one or more administrations daily, for one or several days. Androgen receptor splice variant or androgen receptor splice variant ligand can be administered parenterally by injection or by gradual perfusion over time. It can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases and the like. See, generally, Remington's Pharmaceutical Science, 16th Ed., Mack Eds. (1980).

VIII. Transgenic Androgen Receptor Splice Variant Non-Human Animals—Methods of Generating Transgenic Non-Human Animals The non-human animals of the invention comprise any animal having a transgenic interruption or alteration of the endogenous gene(s) (knock-out animals) and/or into the genome of which has been introduced one or more transgenes that direct the expression of human androgen receptor splice variant protein. Also preferred are the introduction of anti-sense androgen receptor splice variant nucleic acids.

Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by normatural means (i.e., by human manipulation), one or more genes that do not occur naturally in the animal, e.g., foreign genes, genetically engineered endogenous genes, etc. The normaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J. D., et al., in Recombinant DNA, 2d Ed., W.H. Freeman & Co., New York (1992), pages 255 272; Gordon, J. W., Intl. Rev. Cytol. 115:171 229 (1989); Jaenisch, R., Science 240:1468 1474 (1989); Rossant, J., Neuron 2:323 334 (1990)).

In some embodiments, the transgenic non-human animals of the invention are produced by introducing transgenes into the germline of the non-human animal. Embryonic target cells at various developmental stages are used to introduce the transgenes of the invention. Different methods are used depending on the stage of development of the embryonic target cell(s).

In some embodiments, the transgenic animal is made using the modified probasin promoter ARR2PB which is positively regulated by androgen and expressed in the prostate epithelium of sexually mature mice. In some embodiments, the invention is directed to a transgenic animal or its progeny or part thereof, which comprises in its genome a transgene construct comprising a polynucleotide encoding an androgen receptor splice variant encoding a polypeptide of the invention, such as a polypeptide selected from the group consisting of SEQ ID NO: 5, SEQ ID NO:6, SEQ ID NO:7, SEQ ID NO:8 and SEQ ID NO:37. In some embodiments, the transgenic animal is a mouse that expresses AR3. In some embodiments, the transgenic mouse is AR3Tg described below in Example 13.

Transgenes may be introduced into non-human animals in order to provide animal models for human diseases. Transgenic animals harboring one or more of the androgen receptor splice variants of the invention are particularly useful as an animal models for prostate cancer, particularly, androgen refractory prostate cancer. In some embodiments, the transgenic animal is transgenic for AR3, 4, 5 and 8. In other embodiments, the transgenic animal is transgenic for AR3, 4 and 5. In other embodiments, the transgenic animal is transgenic for AR3, 4, and 8. In other embodiments, the transgenic animal is transgenic for AR3, 5 and 8. In other embodiments, the transgenic animal is transgenic for AR3 and 4. In other embodiments, the transgenic animal is transgenic for AR3 and 5. In other embodiments, the transgenic animal is transgenic for AR3 and 8. In other embodiments, the transgenic animal is transgenic for AR4, 5 and 8. In other embodiments, the transgenic animal is transgenic for AR4 and 8. In other embodiments, the transgenic animal is transgenic for AR4 and 5. In other embodiments, the transgenic animal is transgenic for AR5 and 8. Animals that are transgenic for AR4b can also be made, alone, or in combination with the other AR splice variants shown above.

IX. Methods of Treatment

In some embodiments, these novel androgen receptor splice variants herein described can be altered by methods and compositions. For example, gene delivery and gene silencing methods may be used to enhance or inhibit the transcription or translation of these androgen receptor splice variants AR3, AR4, AR4b, AR5 and AR8. Expression of these different androgen receptor splice variants may also be altered by increasing or decreasing the stability of mRNA coding for AR3, AR4, AR4b, AR5 and AR8. The activity of these androgen receptor splice variants may be altered by "gene silencing methods" which are generally regarded as methods that prevent or decrease the rate of transcription or translation of a protein within a cell. Such gene silencing methods include, but are not limited to antisense technology, RNA inhibition technology (RNAi) and inactivation or degradation of transcription factors required for androgen receptor (AR3, AR4, AR4b, AR5 or AR8) transcription, etc.

In some embodiments, the invention is directed to methods of treating or preventing androgen refractory prostate cancer in a patient, comprising administering to the patient in need thereof an effective amount of an agent that inhibits the function of an androgen receptor splice variant selected from the group consisting of AR3, AR4, AR4b, AR5 and AR8. In some embodiments, the agent inhibits expression of the androgen receptor splice variant mRNA, and is selected from the group consisting of antisense oligonucleotide, RNA interference oligonucleotide (RNAi), ribozyme or an agent that degrades transcription factors required for androgen receptor transcription. In some embodiments, the agent is an antagonist that inhibits androgen-independent transcriptional activation by the androgen receptor splice variant. In some embodiments, the agent is an antibody that binds to the androgen receptor splice variant or two or more antibodies that bind to the different androgen receptor splice variants.

In some embodiments, the invention is directed to methods for inhibiting the function of an androgen receptor splice variant in a prostate cancer cell, comprising delivering an agent to the cell selected from the group consisting of an inhibitor of transcription of the androgen receptor splice variant, an inhibitor of translation of the androgen receptor splice variant, and an antagonist of the androgen receptor splice variant, wherein the androgen receptor splice variant is selected from the group consisting of AR3, AR4, AR4b, AR5 and AR8.

Antisense oligonucleotides have been described as naturally occurring biological inhibitors of gene expression in both prokaryotes (Mizuno et al., Proc. Natl. Acad. Sci. USA 81:1966-1970 (1984)) and eukaryotes (Heywood, Nucleic Acids Res. 14:6771-6772 (1986)), and these sequences presumably function by hybridizing to complementary mRNA sequences, resulting in hybridization arrest of translation (Paterson, et al., Proc. Natl. Acad. Sci. USA, 74:4370-4374 (1987)).

Thus, another gene therapy approach utilizes antisense technology. Antisense oligonucleotides are short synthetic DNA or RNA nucleotide molecules formulated to be complementary to a specific gene or RNA message. Through the binding of these oligomers to a target DNA or mRNA sequence, transcription or translation of the gene can be selectively blocked and the disease process generated by that gene can be halted (see, for example, Jack Cohen, Oligodeoxynucleotides, Antisense Inhibitors of Gene Expression, CRC Press (1989)). The cytoplasmic location of mRNA provides a target considered to be readily accessible to antisense oligodeoxynucleotides entering the cell; hence much of the work in the field has focused on RNA as a target. Currently, the use of antisense oligodeoxynucleotides provides a useful tool for exploring regulation of gene expression in vitro and in tissue culture (Rothenberg, et al., J. Natl. Cancer Inst. 81:1539-1544 (1989)).

Antisense therapy is the administration of exogenous oligonucleotides which bind to a target polynucleotide located within the cells. For example, antisense oligonucleotides may be administered systemically for anticancer therapy (Smith, International Application Publication No. WO 90/09180).

The antisense oligonucleotides of the present invention include derivatives such as S-oligonucleotides (phosphorothioate derivatives or S-oligos, see, Jack Cohen, supra). S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer et al., J. Org. Chem. 55:4693-4698 (1990); and Iyer et al., J. Am. Chem. Soc. 112:1253-1254 (1990), the disclosures of which are fully incorporated by reference herein.

The antisense oligonucleotides of the present invention may be RNA or DNA that is complementary to sequences within SEQ ID NO:1, SEQ ID NO:2, SEQ ID NO:3, SEQ ID NO:4, SEQ ID NO:35, SEQ ID NO:36 or SEQ ID NO:38 and stably hybridize with such sequences that are specific for androgen receptor splice variants of the invention. Use of an oligonucleotide complementary to such regions allows for selective hybridization to androgen receptor splice variant mRNA.

In some embodiments, the antisense oligonucleotides of the present invention are a 15 to 30-mer fragment of the antisense DNA molecule coding for sequences of the androgen receptor splice variant cDNAs. Preferred antisense oligonucleotides bind to the 5'-end of the androgen receptor splice variant mRNAs. Such antisense oligonucleotides maybe used to down regulate or inhibit expression of the gene.

Other criteria that are known in the art may be used to select the antisense oligonucleotides, varying the length or the annealing position in the targeted sequence.

Included as well in the present invention are pharmaceutical compositions comprising an effective amount of at least one of the antisense oligonucleotides of the invention in combination with a pharmaceutically acceptable carrier. In one embodiment, a single antisense oligonucleotide is utilized.

In another embodiment, two antisense oligonucleotides are utilized which are complementary to adjacent regions of the genome. Administration of two antisense oligonucleotides that are complementary to adjacent regions of the genome or corresponding mRNA may allow for more efficient inhibition of genomic transcription or mRNA translation, resulting in more effective inhibition of protein or mRNA production.

Preferably, the antisense oligonucleotide is coadministered with an agent which enhances the uptake of the antisense molecule by the cells. For example, the antisense oligonucleotide may be combined with a lipophilic cationic compound which may be in the form of liposomes. The use of liposomes to introduce nucleotides into cells is taught, for example, in U.S. Pat. Nos. 4,897,355 and 4,394,448, the disclosures of which are incorporated by reference in their entirety (see also U.S. Pat. Nos. 4,235,871, 4,231,877, 4,224,179, 4,753,788, 4,673,567, 4,247,411, and 4,814,270 for general methods of preparing liposomes comprising biological materials).

Alternatively, the antisense oligonucleotide may be combined with a lipophilic carrier such as any one of a number of sterols including cholesterol, cholate and deoxycholic acid. A preferred sterol is cholesterol.

In addition, the antisense oligonucleotide maybe conjugated to a peptide that is ingested by cells. Examples of useful peptides include peptide hormones, antigens or antibodies, and peptide toxins. By choosing a peptide that is selectively taken up by the targeted tissue or cells, specific delivery of the antisense agent maybe effected. The antisense oligonucleotide maybe covalently bound via the 5'OH group by formation of an activated aminoalkyl derivative. The peptide of choice may then be covalently attached to the activated antisense oligonucleotide via an amino and sulfhydryl reactive hetero bifunctional reagent. The latter is bound to a cysteine residue present in the peptide. Upon exposure of cells to the antisense oligonucleotide bound to the peptide, the peptidyl antisense agent is endocytosed and the antisense oligonucleotide binds to the target mRNA to inhibit translation (Haralambid et al., WO 8903849 and Lebleu et al., EP 0263740).

The antisense oligonucleotides and the pharmaceutical compositions of the present invention may be administered by any means that achieve their intended purpose. For example, administration may be by parenteral, subcutaneous, intravenous, intramuscular, intraperitoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the antisense oligonucleotide is contained in an amount effective to achieve the desired effect, for example, inhibition of proliferation and/or stimulation of differentiation of the subject cancer cells.

Alternatively, antisense oligonucleotides can be prepared which are designed to interfere with transcription of the gene by binding transcribed regions of duplex DNA (including introns, exons, or both) and forming triple helices (e.g., see Froehler et al., WO 91/06626 or Toole, WO 92/10590). Preferred oligonucleotides for triple helix formation are oligonucleotides which have inverted polarities for at least two regions of the oligonucleotide (Id.). Such oligonucleotides comprise tandem sequences of opposite polarity such as 3'- - -5'-L-5' - - - 3', or 5' - - - 3'-L-3' - - - 5', wherein L represents a 0-10 base oligonucleotide linkage between oligonucleotides. The inverted polarity form stabilizes single-stranded oligonucleotides to exonuclease degradation (Froehler et al., supra). The criteria for selecting such inverted polarity oligonucleotides is known in the art, and such preferred triple helix-forming oligonucleotides of the invention are based upon SEQ ID NO:1, SEQ ID NO:2, SEQ ID NO:3, SEQ ID NO:4, SEQ ID NO:35, SEQ ID NO:36 or SEQ ID NO:38.

In therapeutic application, the triple helix-forming oligonucleotides can be formulated in pharmaceutical preparations for a variety of modes of administration, including systemic or localized administration, as described above.

The antisense oligonucleotides of the present invention may be prepared according to any of the methods that are well known to those of ordinary skill in the art, as described above.

Generally, RNAi technology is limited to tissue-specific or organ-specific areas of the subject using tissue specific gene promoters or transcription factors. Promoters are nucleic acids that are generally located in the 5' region of a gene, proximal to the start codon or nucleic acid which encodes untranslated RNA. The transcription of an adjacent nucleic acid segment is initiated at the promoter region. Any suitable promoter may be used to control the production of RNA from the nucleic acid molecules of the invention. Promoters may be those recognized by any polymerase enzyme; for example, promoters may be promoters for RNA polymerase II or polymerase III. Suitable promoters are known in the art and are within the scope of the present invention. Recombinant DNA methods, such as those that might be used to prepare constructs of a tissue-specific promoter operably linked to a coding region coding for mRNA are well known in the art.

The dsRNA molecules are digested in vivo to 21-23 nt fragment small interfering RNAs (siRNAs) which mediate the RNAi effect. In *C. elegans* and *Drosophila*, RNAi is induced by delivery of long dsRNA (up to 1-2 kb) produced by in vitro transcription. In mammalian cells, introduction of long dsRNA elicits a strong antiviral response that blocks any gene-specific silencing. However, introduction of 21 nt siRNAs with 2 nt 3' overhangs into mammalian cells does not stimulate the antiviral response and effectively targets specific mRNAs for gene silencing. The specificity of this gene silencing mechanism is extremely high, blocking expression only of targeted genes, while leaving other genes unaffected. Expression of androgen receptor splice variant transcripts of the invention may be turned off, for example, by delivery of siRNAs or vectors encoding the same into gonads or early embryos. In another embodiment, the siRNAs are delivered to cells or tissues to turn off expression of one or more androgen receptor splice variants. In one embodiment, the cells are androgen refractory prostate cancer cells. The artisan will appreciate that the siRNAs may be delivered to cells using an in vivo or ex vivo approach. Preferred ex vivo approaches involve transferring siRNAs to blood cells, bone marrow-derived cells, or stem cells.

The siRNAs or vectors encoding the same may be delivered to cells by techniques known in the art as described above. Further, the siRNAs may be prepared by any methods that are known in the art, including, but not limited to, oligonucleotide synthesis, in vitro transcription, ribonuclease digestion, or generation of siRNAs in vivo. In one embodiment, the siRNAs may be produced from vectors that are introduced into cells. The vectors may be introduced by any known methods in the art, including but not limited to transfection, electroporation, or viral delivery systems. In some embodiments, the vectors are the pSilencer siRNA expression vectors, pSilencer 2.0-U6 and pSilencer 3.0-H1. In a further embodiment, transcription of the siRNAs is driven by a RNA polymerase III (pol III) promoter. The pol III promoter may be derived from any gene that is under the control of RNA polymerase III, including but not limited to H1 or U6.

A small hairpin RNA or short hairpin RNA (shRNA), or nucleic acids encoding them can also be introduced into cells to produce siRNA. Short hairpin RNA is a sequence of RNA that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it.

In some embodiments, the siRNAs of the invention are encoded by nucleotide sequences within SEQ ID NO:1, SEQ ID NO:2, SEQ ID NO:3, SEQ ID NO:4, SEQ ID NO:35, SEQ ID NO:36 or SEQ ID NO:38. In one embodiment, the siRNAs are about 20-1000 nucleotides in length. In another embodiment, the siRNAs are about 20-500 nucleotides in length. In another embodiment, the siRNAs are about 20-100 nucleotides in length. In another embodiment, the siRNAs are about 20-50 nucleotides in length. In another embodiment, the siRNAs are about 21-23 nucleotides in length. The siRNAs may be produced by PCR amplification of genomic DNA or cDNA, using primers derived from androgen receptor splice variant sequence, and cloned into expression vectors for siRNA production. In another embodiment, oligonucleotides that correspond to androgen receptor splice variant sequence may be chemically synthesized and inserted into expression vectors for siRNA production. The siRNAs or vectors encoding the same are introduced into cells to block expression of the androgen receptor splice variant polypeptides. siRNA can also be produced by chemical synthesis of oligonucleotide of RNA of 21-23 nucleotides. In some embodiments, the androgen receptor splice variants to be knocked down using RNAi are selected from the group consisting of AR3, AR4, Ar4b, AR5 and ARB. In some embodiments, the androgen receptor to be knocked down is AR3. In some embodiments, short hairpin RNA is used to knock down AR3. In some embodiments, the short hairpin RNA is shAR3-1 (made using SEQ ID NOS:13 and 14) or shAR3-2 (made using SEQ ID NOs:15-16). In some embodiments, siRNA directed against SEQ ID NO:30 encoding AR8 is used to knock down AR8 in cells.

In one embodiment, the siRNAs are composed of nucleotides A, G, T, C, or U. Additionally, the siRNAs may be composed of unusual or modified nucleotides including but not limited to inosinic acid, 1-methyl inosinic acid, 1-methyl guanylic acid, NN-dimethyl guanylic acid, pseudouridylic acid, ribothymidylic acid, 5-hydroxymethylcytosine, and 5-hydroxymethyluridine. RNA may be synthesized either in vivo or in vitro and later introduced into cells. Endogenous RNA polymerase of the cell may mediate transcription in vivo, or cloned RNA polymerase can be used for transcription in vitro. For transcription from a transgene in vivo or an expression construct, a regulatory region (e.g., promoter, enhancer, silencer, splice donor and acceptor, polyadenylation) maybe used to transcribe the RNA strand (or strands); the promoters may be known inducible promoters that respond to infection, stress, temperature, wounding, or chemicals. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874; 5,698,425; 5,712,135; 5,789,214; and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA containing nucleotide sequence identical to a fragment of the androgen receptor splice variant sequences are preferred for inhibition; however, RNA sequences with insertions, deletions, and point mutations relative to the androgen receptor splice variant sequences of the invention can also be used for inhibition. Sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

In some embodiments, the invention is directed to a method for treating cancer in an animal comprising administering to the animal an isolated short interfering RNA molecule that inhibits expression of an androgen receptor splice variant selected from the group consisting of AR3 (SEQ ID NO:1), AR4 (SEQ ID NO:2 or 35), AR4b (SEQ ID NO:36 or 38), AR5 (SEQ ID NO:3) and AR8 (SEQ ID NO:4).

Ribozymes may also be used for gene silencing. For example, antisense RNA/ribozyme fusions which comprise (1) antisense RNA corresponding to a target gene and (2) one or more ribozymes which cleave RNA can be used, as well as vectors which express these fusions, methods for producing these vectors, and methods for using these vectors.

Preferred targets for ribozymes are androgen receptor splice variant nucleotide sequences. In some embodiments, the ribozyme molecule of the present invention is designed based upon the chloramphenicol acetyltransferase ribozyme or hairpin ribozymes. Alternatively, ribozyme molecules are designed as described by Eckstein et al., (International Publication No. WO 92/07065) who disclose catalytically active ribozyme constructions which have increased stability against chemical and enzymatic degradation, and thus are useful as therapeutic agents.

In an alternative approach, an external guide sequence (EGS) can be constructed for directing the endogenous ribozyme, RNase P, to intracellular mRNA, which is subsequently cleaved by the cellular ribozyme (Altman et al., U.S. Pat. No. 5,168,053). Preferably, the EGS comprises a ten to fifteen nucleotide sequence complementary to an mRNA and a 3'-NCCA nucleotide sequence, wherein N is preferably a purine (Id.). After EGS molecules are delivered to cells, as described below, the molecules bind to the targeted mRNA species by forming base pairs between the mRNA and the complementary EGS sequences, thus promoting cleavage of mRNA by RNase P at the nucleotide at the 5' side of the base-paired region (Id.).

Included as well in the present invention are pharmaceutical compositions comprising an effective amount of at least one ribozyme or EGS of the invention in combination with a pharmaceutically acceptable carrier. Preferably, the ribozyme or EGS is coadministered with an agent which enhances the uptake of the ribozyme or EGS molecule by the cells. For example, the ribozyme or EGS may be combined with a lipophilic cationic compound which may be in the form of liposomes, as described above. Alternatively, the ribozyme or EGS may be combined with a lipophilic carrier such as any one of a number of sterols including cholesterol, cholate and deoxycholic acid. A preferred sterol is cholesterol.

The ribozyme or EGS, and the pharmaceutical compositions of the present invention may be administered by any means that achieve their intended purpose. For example, administration may be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired. For example, as much as 700 milligrams of antisense oligodeoxynucleotide has been administered intravenously to a patient over a course of 10 days (i.e., 0.05 mg/kg/hour) without signs of toxicity (Sterling, "Systemic Antisense Treatment Reported," Genetic Engineering News 12(12):1, 28 (1992)).

Compositions within the scope of this invention include all compositions wherein the ribozyme or EGS is contained in an amount which is effective to achieve inhibition of proliferation and/or stimulate differentiation of the subject cancer cells, or alleviate AD. While individual needs vary, determination of optimal ranges of effective amounts of each component is with the skill of the art.

In addition to administering the antisense oligonucleotides, ribozymes, or EGS as a raw chemical in solution, the therapeutic molecules may be administered as part of a pharmaceutical preparation containing suitable pharmaceutically acceptable carriers comprising excipients and auxiliaries which facilitate processing of the antisense oligonucleotide, ribozyme, or EGS into preparations which can be used pharmaceutically.

Suitable formulations for parenteral administration include aqueous solutions of the antisense oligonucleotides, dsRNAs, ribozymes, EGS in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Alternatively, antisense RNA molecules, ribozymes, and EGS can be coded by DNA constructs which are administered in the form of virions, which are preferably incapable of replicating in vivo (see, for example, Taylor, WO 92/06693). For example, such DNA constructs may be administered using herpes-based viruses (Gage et al., U.S. Pat. No. 5,082,670). Alternatively, antisense RNA sequences, ribozymes, and EGS can be coded by RNA constructs which are administered in the form of virions, such as retroviruses. The preparation of retroviral vectors is well known in the art (see, for example, Brown et al., "Retroviral Vectors," in DNA Cloning: A Practical Approach, Volume 3, IRL Press, Washington, D.C. (1987)).

Specificity for gene expression may be conferred by using appropriate cell-specific regulatory sequences, such as cell-specific enhancers and promoters. Such regulatory elements are known in the art, and their use enables therapies designed to target specific tissues, such as liver, lung, prostate, kidney, pancreas, etc., or cell populations, such as lymphocytes, neurons, mesenchymal, epithelial, muscle, etc.

In the method of treating an androgen receptor splice variant-associated disease (preferably, prostate cancer, in particular, androgen refractory prostate cancer) in a patient in need of such treatment, in some embodiments, gene replacement ("knock out") technology is used that would replace or delete the disease causing androgen receptor splice variant sequences to treat the disease (specifically, prostate cancer or androgen refractory prostate cancer).

Included as well in the invention are pharmaceutical compositions comprising an effective amount of at least one androgen receptor splice variant antisense oligonucleotide, in combination with a pharmaceutically acceptable carrier. Such antisense oligos include, but are not limited to, at least one nucleotide sequence which is complementary to exons encoding androgen receptor splice variants; a DNA sequence of SEQ ID NO:1, 2, 3, 4, 35, 36 or 38; or a DNA sequence encoding at least 4 amino acids of SEQ ID NO:1, SEQ ID NO:2, SEQ ID NO:3, SEQ ID NO:4, SEQ ID NO:35, SEQ ID NO:36 or SEQ ID NO:38.

Alternatively, the androgen receptor splice variant nucleic acid can be combined with a lipophilic carrier such as any one of a number of sterols including cholesterol, cholate and deoxycholic acid. A preferred sterol is cholesterol.

The androgen receptor splice variant nucleic acids and the pharmaceutical compositions of the invention can be administered by any means that achieve their intended purpose. For example, administration can be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the androgen receptor splice variant antisense oligonucleotide is contained in an amount effective to achieve decreased expression of the androgen receptor splice variant mRNA encoded by the androgen receptor gene. While individual needs vary, determination of optimal ranges of effective amounts of each component is within the skill of the art. Typically, the androgen receptor splice variant nucleic acid can be administered to mammals, e.g. humans, at a dose of 0.005 to 1 mg/kg/day, or an equivalent amount of the pharmaceutically acceptable salt thereof, per day of the body weight of the mammal being treated.

Suitable formulations for parenteral administration include aqueous solutions of the androgen receptor splice variant nucleic acid in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances which increase the viscosity of the suspension include, for example, sodium carboxymethyl cellulose, sorbitol, and/or dextran. Optionally, the suspension can also contain stabilizers.

Many vector systems are known in the art to provide such delivery to human patients. For example, retrovirus systems can be used, especially modified retrovirus systems and especially herpes simplex virus systems (Gage et al., U.S. Pat. No. 5,082,670). Such methods are provided for, in, for example, the teachings of Breakefield, X. A. et al., The New Biologist 3:203 218 (1991); Huang, Q. et al., Experimental Neurology 115:303 316 (1992); WO93/03743; WO90/0944; Taylor, WO 92/06693; Mulligan, R. C., Science 260:926 932 (1993); and Brown et al., "Retroviral Vectors," in DNA Cloning: A Practical Approach, Volume 3, IRL Press, Washington, D.C. (1987).

The means by which the vector carrying the nucleic acid can be introduced into the cell include but is not limited to, microinjection, electroporation, transduction, or transfection using DEAE-Dextran, lipofection, calcium phosphate or other procedures known to one skilled in the art (Molecular Cloning, A Laboratory Manual, Sambrook et al., eds., Cold Spring Harbor Press, Plainview, N.Y. (1989)).

Further methods which can be used to transfer nucleic acid to a patient are set forth in Chatterjee and Wong, Current Topics in Microbiol. Immuno., 218: 61 73 (1996); Zhang, J. Mol. Med. 74:191 204 (1996); Schmidt-Wolf and Schmidt-Wolf, J. of Hematotherapy 4:551 561 (1995); Shaughnessy et al., Seminars in Oncology 23 (1): 159 171 (1996); and Dunbar Annu. Rev. Med. 47:11 20 (1996).

Specificity for gene expression in prostate cancer cells can be conferred by using appropriate cell-specific regulatory sequences, such as cell-specific enhancers and promoters.

Other methods of inhibiting the activity of these novel androgen receptor splice variants include the use of antibodies or functional fragments, or other antagonists which bind the androgen receptor. As used herein, the term antibody includes at least monoclonal antibodies and polyclonal antibodies and functional fragments of an antibody. Antibodies or functional fragments thereof can be used as agonists or antagonists of AR3, AR4, AR4b, AR5, or ARB. Use of functional fragments, such as the Fab, Fab', or F(ab')2 fragments are often suitable, especially in a therapeutic context, as these fragments are generally less immunogenic than the whole immunoglobulin.

Antibodies are prepared by well-known methods in the art, such as immunizing suitable mammalian hosts in appropriate immunization protocols using AR fragments or peptides or polypeptides as discussed above. These peptides, polypeptides or fragments can be conjugated to suitable carriers such as BSA (bovine serum albumin), KLH (Keyhole limpet hemocyanin), or the like.

While the polyclonal antisera produced in this way be satisfactory for some applications, for pharmaceutical application, use of monoclonal preparations is also suitable. Immortalized cell lines which secrete the desired monoclonal antibodies may be prepared using the standard method of Kohier and Milstein or modification which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured in vitro or by production in ascites fluid. The desired monoclonal antibodies can then be recovered from the culture supernatant.

The antibodies or fragments may also be produced by recombinant methods. Regions that bind specifically to the desired regions of the AR or its downstream effector molecules can also be produced in the context of chimeras with multiple species origin. Humanized and fully human antibodies, such as those identified by phage display or produced by a Xenomouse, are also contemplated. Antibody reagents so created are contemplated for use diagnostically or as stimulants or inhibitors of the activity of androgen receptor (AR) splice variants herein described.

In some embodiments, the antibodies are directed against AR3 (SEQ ID NO:5), AR4 (SEQ ID NO:6), AR4b (SEQ ID NO: 37), AR5 (SEQ ID NO:7) or AR8 (SEQ ID NO:8) polypeptides.

In one embodiment, the invention includes methods for treating a subject having a neoplastic disorder, such as prostate cancer or androgen refractory prostate cancer, comprising administering to a subject in need of treatment a pharmaceutical formulation comprising (i) one or more antibodies that specifically bind an androgen receptor splice variant and (ii) a pharmaceutically acceptable carrier, thereby treating a subject having a neoplastic disorder. In one aspect, the one or more antibodies inhibit an activity of the AR8 androgen receptor splice variant. In a particular embodiment, the invention includes methods for treating a subject having a neoplastic disorder, such as prostate cancer or androgen refractory prostate cancer, comprising administering to a subject in need of treatment a pharmaceutical formulation comprising (i) two or more antibodies that specifically bind two different androgen receptor splice variants and (ii) a pharmaceutically acceptable carrier, thereby treating a subject having a neoplastic disorder. In one aspect, the antibodies are antibodies that bind AR4 and AR8. In a further aspect, the one or more antibodies are coupled to a therapeutic moiety, such as a radionuclide, cytotoxic agent and/or a cytotoxic drug.

Treatment comprises parenterally administering a single or multiple doses of the antibody, fragment or derivative. Preferred for human pharmaceutical use are high affinity potent androgen receptor splice variant-inhibiting and/or neutralizing murine and chimeric antibodies, fragments and regions of this invention.

In some embodiments, the invention is directed to methods for inhibiting the activity of androgen splice receptor variants AR3, AR4, AR4b, AR5 or AR8 in a prostate cancer cell comprising administering to said cell an antibody or functional fragment of said antibody which binds the androgen receptor. In another embodiment, the invention is directed to methods for inhibiting the activity of two or more androgen splice receptor variants, selected from AR3, AR4, AR4b, AR5 and AR8, in a prostate cancer cell comprising administering to said cell two or more antibodies or functional fragments of said antibodies which binds androgen receptors in the cell. In one aspect, antibodies against both AR4 and AR8 are administered to a subject having prostate cancer.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

For parenteral administration, the antibody can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of Remington's Pharmaceutical Sciences, A. Osol, a standard reference text in this field.

The antibodies of the present invention can also be used therapeutically as immunoconjugates (see for review: Dillman, R. O., Ann. Int. Med. 111:592 603 (1989)). The antibodies can be coupled to a therapeutic moiety, such as a radionuclide, a cytotoxic agent and/or a cytotoxic drug. Cytotoxic agents, include, but are not limited to, Ricin-A, *Pseudomonas* toxin, and Diphtheria toxin. Toxins conjugated to antibodies or other ligands, are known in the art (see, for example, Olsnes, S. et al., Immunol. Today 10:291 295 (1989)). Plant and bacterial toxins typically kill cells by disrupting the protein synthetic machinery.

Examples of radionuclides which can be coupled to antibodies and delivered in vivo to sites of antigen include $^{212}$Bi, $^{131}$I, $^{186}$Re, and $^{90}$Y, which list is not intended to be exhaustive. The radionuclides exert their cytotoxic effect by locally irradiating the cells, leading to various intracellular lesions, as is known in the art of radiotherapy.

Cytotoxic drugs which can be conjugated to antibodies and subsequently used for in vivo therapy include, but are not limited to, daunorubicin, doxorubicin, methotrexate, and Mitomycin C. Cytotoxic drugs interfere with critical cellular processes including DNA, RNA, and protein synthesis. For a fuller exposition of these classes of drugs which are known in the art, and their mechanisms of action, see Goodman, A. G., et al., Goodman and Gilman's THE PHARMACOLOGICAL BASIS OF THERAPEUTICS, 7th Ed., Macmillan Publishing Co., 1985.

The antibodies of this invention may be advantageously utilized in combination with other monoclonal or murine and chimeric antibodies, fragments and regions, or with lymphokines or hematopoietic growth factors, etc., which serve to increase the number or activity of effector cells which interact with the antibodies.

Application of the teachings of the present invention to a specific problem or environment is within the capabilities of one having ordinary skill in the art in light of the teaching contained herein. Examples of the products and processes of the invention appear in the following non-limiting Examples.

EXAMPLES

Example 1

Identification of Novel Androgen-Independent AR Alternative Splicing Isoforms

Figure 7:
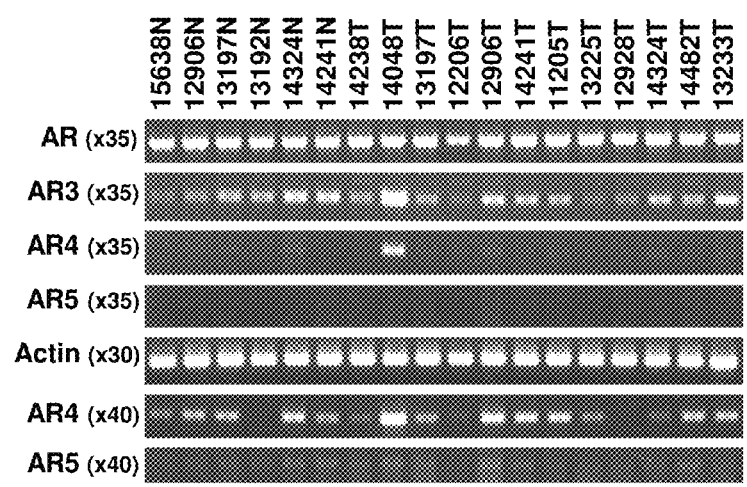
FIG. 7. Expression of AR, AR3, AR4, and AR5 in human normal and malignant prostate tissues.
Figure 8:
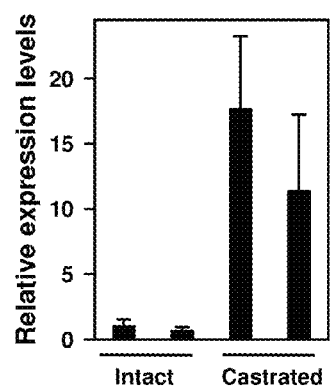
FIG. 8. Increased AR3 expression in hormone refractory prostate tumor xenografts.

We examined the expression of AR protein in a panel of PCA cell lines using an antibody recognizing the N-terminus of AR. In addition to the well characterized 110 kD AR protein, we detected one band approximately 80 kD in the LNCaP derivative C-81, CWR-R1 and 22Rv1 cells which are known to grow in the androgen-depleted medium (FIG. 1a). This short form of AR (ARs) appeared to correspond to the truncated AR previously reported in CWR-R1 and 22Rv1 cells. On the other hand, the 80 kD ARs was barely detectable in the androgen-dependent LAPC4 and LNCaP cells. These data implied an inverse correlation between the ARs and androgen-dependency of these cell lines in cell culture. To confirm that the 80 kD ARs was indeed derived from the AR gene, we treated CWR-R1 with a panel of shRNAs specifically targeting distinct regions of the AR gene. These shRNAs could differentially knock down AR and ARs, suggesting that AR and ARs may be translated from more than one transcript. ARs was efficiently knocked down by shARc targeting at the 1st Exon but barely affected by the shARb or shARa targeting at Exon 5 and 8 respectively. This finding implies that the transcript encoding the ARs may contain Exon 1 but may not have intact Exons 5 and 8. Similar effects were also observed in the 22Rv1 cells (data not shown). These findings prompted us to clone possible alternative splice variants of AR in these cells by using the 3' RACE with a primer corresponding to the shARc target sequence. As shown in FIG. 1c, multiple PCR products resulted from the 3' RACE were detected. Subsequent cloning and sequencing analysis revealed that the major band around 2 kb turned out to be the 110 kD prototype AR. The other bands were found to be-the result of alternative splicing through various mechanisms including exon skipping, cryptic splicing donor or acceptor usage, cryptic exon inclusion, etc. More than 20 splicing variants have been identified so far. Among them, three variants (designated as AR3, AR4 and AR5) were predicted to be translated into a protein around 80 kD, similar to the one we and other detected in CWR-R1 and 22Rv1 cells (FIGS. 11-13). The schematic gene structures of these AR variants are shown in FIG. 1d. They contain-the intact NTD and the DBD but lack the hinge region and the LBD. Instead, they contain 16-53 unique amino acids, which are not present in AR, at their C-termini respectively. We then designed the isoform specific primers that only recognize the unique junction sequence present in each isoform. These isoforms were detected in a panel of human benign and malignant prostate tissues by RT-PCR (FIG. 7). FIG. 1e shows that AR3 appeared to be one of the most frequently and abundantly expressed isoforms detected in all three hormone refractory cell lines in our real-time PCR analysis. Consistent with the Western Blot data in FIG. 1a, the expression level of AR3 is significantly increased in the high passage androgen-independent LNCaP derivative C-81, compared with the parental androgen-sensitive LNCaP cells (FIG. 1e right panel). We also detected an increase of AR3 expression in hormone refractory CWR22 xenografts compared to the hormone naïve counterparts (FIG. 8), suggesting a role of AR3 in androgen independence. Previous studies have shown that the deletion of the ligand binding domain of AR leads to constitutive activation of its transcriptional activity. Therefore, these AR splice variants may be constitutively active in their host cells and exert its transcriptional activity in a true androgen-independent manner. The AR isoforms were transiently transfected into COS-1 cells and their effects on the ARE-containing promoter reporter activity were tested. As expected, all the three AR isoforms induced androgen independent activation of the reporter. AR3 appeared to be most active in the luciferase assay compared to the other two splice variants (FIG. 10. We therefore focused our functional study on AR3. In addition, the AR3 activity was increased in a dose-dependent manner, however, unlike the prototype AR whose activity was dramatically stimulated by addition of DHT, the transcriptional activity of AR3 is completely independent of androgen (FIG. 1g). We also overexpressed AR3 in LNCaP cells and examined whether its activity could be modulated by AR, androgen or anti-androgen. FIG. 1h shows that inhibition of AR either by the specific shRNA or casodex did not affect AR3 activity regardless of DHT treatment while the activity of the endogenous AR or the exogenous codon-switched wild-type AR (ARcs, as described previously (Guo, Z. et al., Cancer Cell 10, 309-19 (2006)) was induced by DHT and blocked by casodex as expected. Thus, AR3 activity is not controlled by DHT, casodex or the status of AR, suggesting that AR3 may be a true androgen independent transcription factor.

Figure 2:
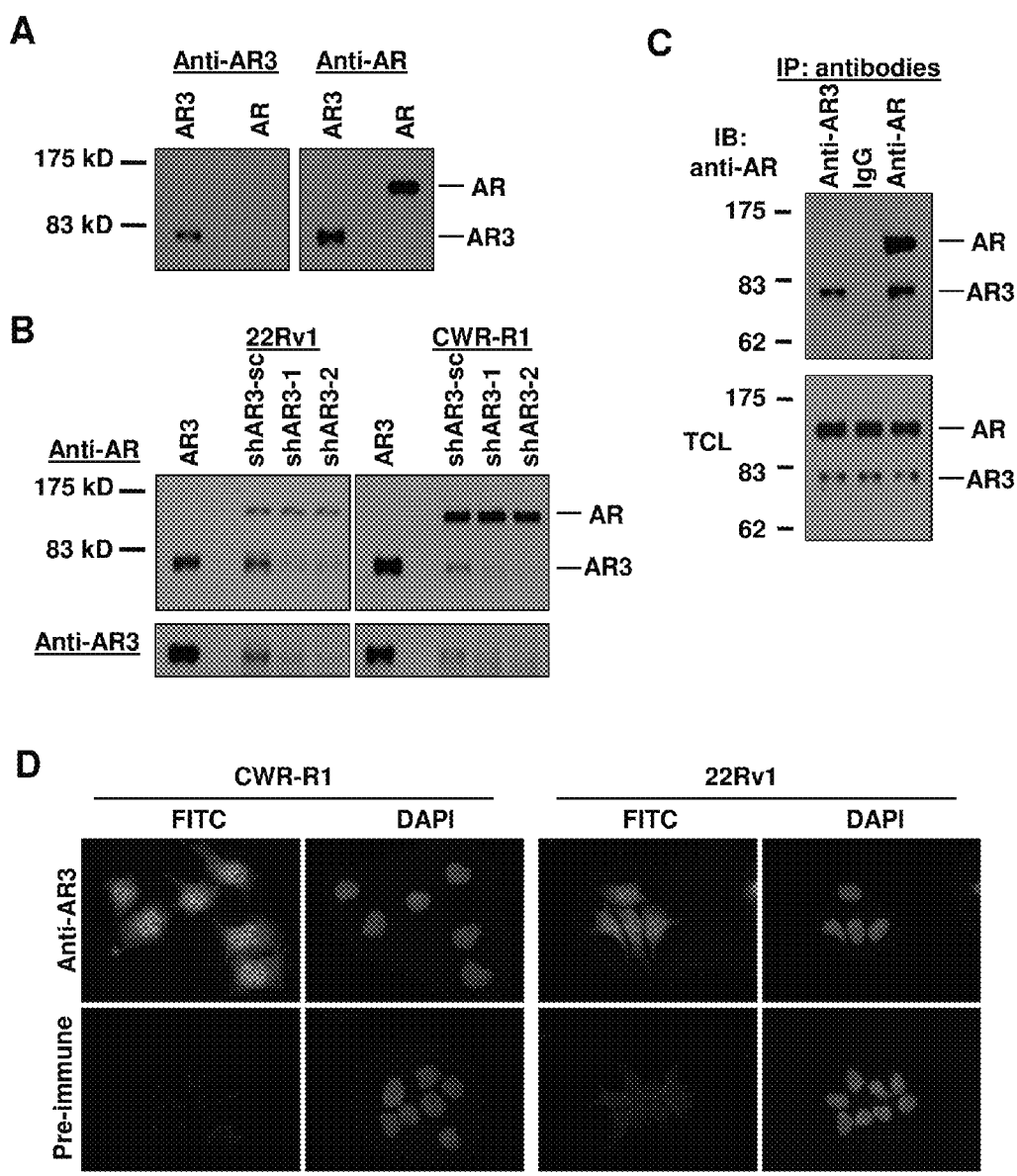
FIGS. 2A-D: Detection of AR3 isoform in hormone refractory prostate cancer cells by the anti-AR3 antibody. (A) COS-1 cells were transfected with AR3 or AR expression vector. The total protein lysates were immunoblotted with anti-AR3 and anti-AR antibodies, respectively. (B) CWR-R1 and 22Rv1 cells were infected with lentivirus encoding AR3 shRNA-1, -2 (shAR3-1, -2) or the scrambled control AR3 shRNA (shAR3-sc). At 48 hr postinfection, the cells were lysed and subjected to immunoblotting with anti-AR (441) and anti-AR3 antibodies, respectively. The lysates of COS-i cells overexpressing AR.3 were used as a positive control (first lane). (C) The lysates of CWR-R1 cells were split into three equal aliquots and immnuoprecipitated with anti-AR3 antibody, control antibody IgG and anti-AR antibody, respectively. The resultant immunoprecipitates and the input total cell lysates (TCL) were immunoblotted with anti-AR. antibody. (D) Subcellular Localization of AR3. CWR-R1 and 22Rv1 cells were subjected to immunofluorescence staining with anti-AR3 antibody or the control pre-immune serum. The nucleus was visualized with DAPI staining.

To further characterize the endogenous AR3, we developed a polyclonal antibody which specifically recognizes the unique sequence at the C-terminus of AR3. FIG. 2a shows that the anti-AR3 antibody only detected the overexpressed AR3 but not AR in COS-1 cells. Knock-down of AR3 expression in 22Rv1 and CWR-R1 cells by treatment with the specific shRNAs for AR3 diminished the immunoreactivity of the anti-AR3 as well as the anti-AR with the 80 kD ARs but it had little effect on the anti-AR reactivity with the 110 kD AR (FIG. 2b). The anti-AR3 antibody could efficiently and selectively immunoprecipitate the endogenous AR3 but not AR (FIG. 2c). Immunofluorescence staining revealed that AR3 was present in both nucleus and cytoplasm in CWR-R1 and 22Rv1 cells (FIG. 2d). Western Blot analysis showed AR3 is expressed in all tested AR-positive prostate cancer cell lines. It is noteworthy that the level of AR3 in the androgen-independent LNCaP derivatives C81, C4-2 and C4-2B was significantly higher than that in the androgen-sensitive parental line (FIG. 3a). Immunohistochemistry analysis on human prostate tissue microarrays revealed a marked change in AR3 expression level and pattern in malignant prostate tissues compared to the benign counterparts (FIG. 3b). In benign prostate tissues, the anti-AR3 antibody mainly stained the basal cells as well as the stroma cells but most of luminal cells were barely stained (the mean cytoplasmic staining score 1.52±0.34) (FIG. 3c and FIG. 10). On the other hand, the majority of luminal cells in the malignant glands showed strong cytoplasmic staining by the AR3 antibody (mean score 4.74±0.13). In addition, a significant redistribution of AR3 protein to the nucleus was observed in the hormone refractory tumor tissue samples (44% nuclear positive) compared to the hormone naïve counterparts (9% nuclear positive). Thus, nuclear translocation of AR3 is significantly increased in hormone refractory prostate tumors. To assess whether AR3 could be used as a potential prognostic marker for prostate cancer, clinical outcome analysis was performed on 224 PCA patient samples with clinicopathological information. Patients with elevated PSA levels following radical prostatectomy are at a high risk to develop distant metastases and die of prostate cancer. Clinical failure was defined as a PSA elevation of greater than 0.2 ng/ml following radical prostatectomy with successive increasing PSA values. Kaplan-Meier analysis indicated that prostate cancer patients that have higher cytoplasmic staining of AR3 (staining score>=6) have a greater risk for PSA recurrence after radical prostatectomy (FIG. 3d, log-rank test, p<0.0001). To test whether overexpression of AR3 in prostate cancer cells could confer androgen-independent growth, LNCaP cells were infected with the lentivirus encoding AR3 and maintained in the medium supplemented with the charcoal-stripped serum. As shown in FIG. 4a, overexpression of AR3 in LNCaP cell promoted growth in androgen-depleted medium. Such growth enhancement was also observed in the castrated SCID mice xenograft models (FIG. 4b). We further investigated whether expression of AR3 in hormone refractory prostate cancer cells is required for androgen-independent growth by specifically knocking down AR3. As shown in FIGS. 4c and 4d, treatment of both 22Rv1 and CWR-R1 cells with the lentivirus encoding the shRNA specific for AR3 attenuated their growth in the androgen-depleted medium as well as in the castrated nude mice, suggesting that AR3 activity is required for prostate cancer cell growth in both cell culture and xenograft models under androgen-depleted conditions. It should be noted that knockdown of AR3 in these cells did not alter the expression of AR, therefore, AR3 may play an indispensable role in promoting androgen-independent growth of prostate cancer, possibly through regulating a different subset of target genes that are not shared with AR.

Figure 5:
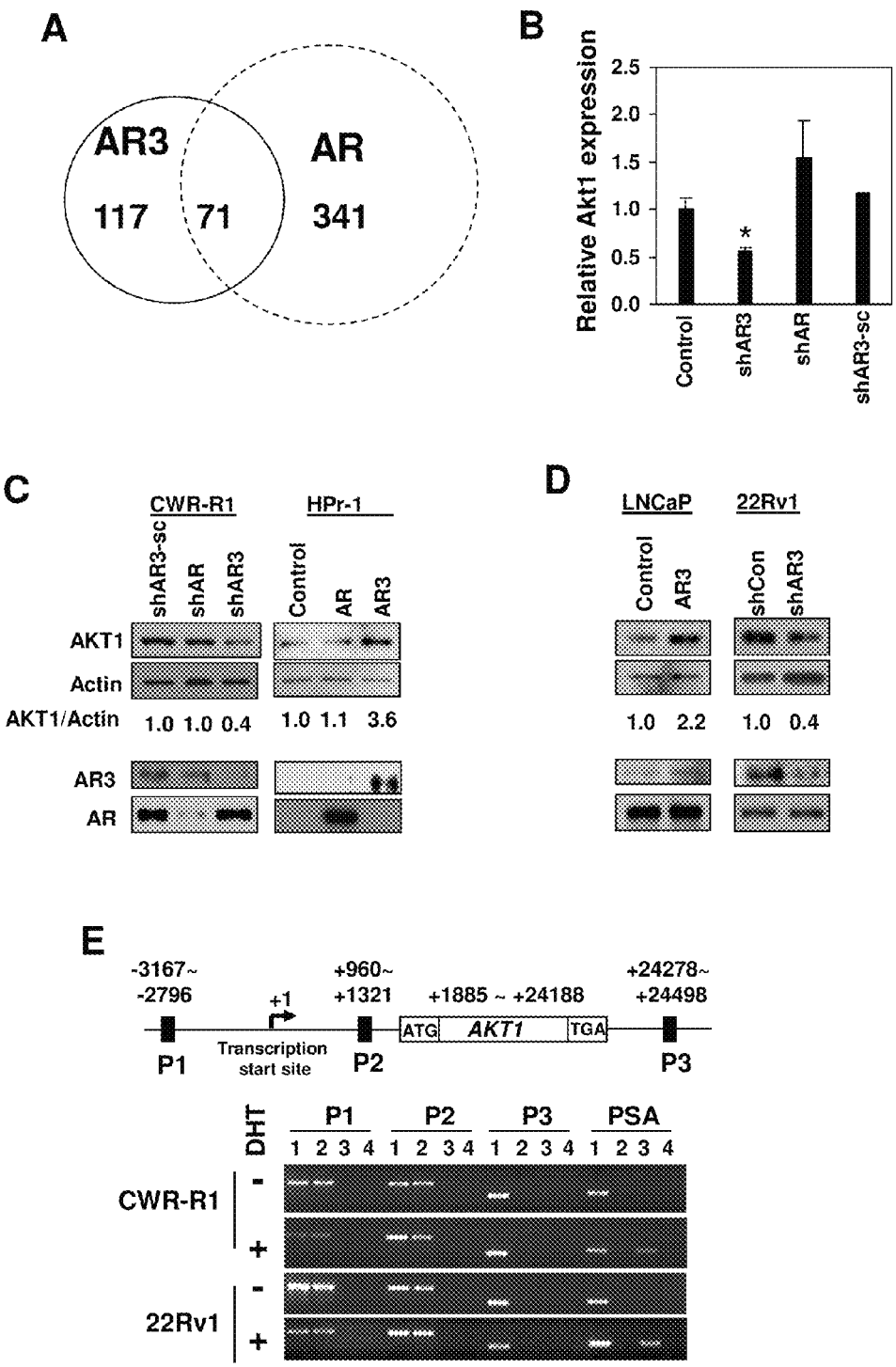
FIGS. 5A-E: AKT1 is a target gene regulated by AR3. (A) Schematic representation of the AR3 and AR regulated genes. (B) The effects of AR3 shRNA on the transcription of endogenous AKT1. The CWR-R1 cells were infected with lentivirus encoding AR3 shRNA-1 (shAR3), AR shRNA (shAR) or AR3 shRNA scrambled control (shAR3-sc). At 48 hr post infection, the total RNA was isolated and reverse transcribed. The relative expression levels of AKT1 transcripts compared with the vector (Control) was quantified by real-time PCR ($*p<0.05$). (C) CWR-R1 cells were infected with the lentivirus encoding shAR3, shAR and shAR3-sc. 1IPr-1 cells were infected with the lentivirus encoding AR, AR3 or the vector control. At 48 hr post infection, the cells were lysed and the protein levels of AKT1, Actin, AR3 and AR were detected by immunoblotting. The levels of AKT1 from the immunoblots were normalized by calculating the ratios of AKT1/actin. The changes in fold compared to the control were shown (bottom). (D) The lysates of LNCaP and 22Rv1 xenograft tumors from FIGS. 4a and 4b were subjected to immunoblotting as described in (c). (E) CWR-R1 and 22Rv1 cells were treated with or without DHT (10 nM) for 1 hr. The binding of AR3 and AR to the different putative ARE sites (P1, P2 and P3) of human AKT1 gene was analyzed by the ChIP assay An ARE binding site at the PSA enhancer region (PSA) was used as a positive control for AR. PCR products from input (1), immunoprecipitation with anti-AR3 antibody (2), anti-AR antibody (3) or the control antibody (4), were resolved on agarose gels.
Figure 6:
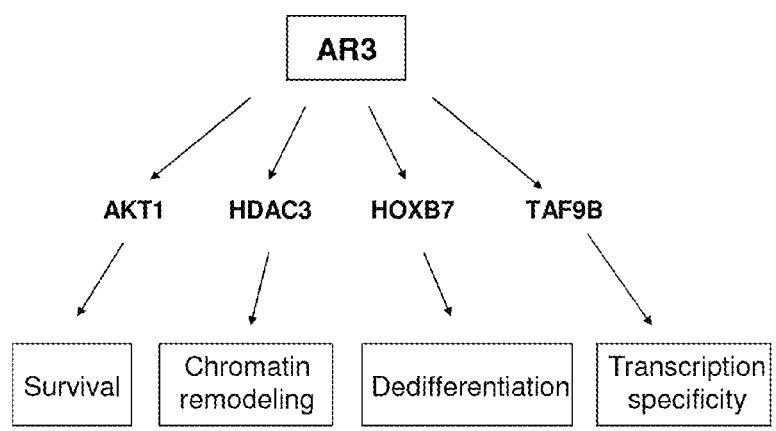
FIG. 6. The postulated role of AR3 in prostate cancer cells.

To identify potential AR3 target genes in hormone refractory prostate cancer cells, we selectively knocked down AR3 or AR by the specific shRNAs in two different cell lines CWR-R1 and 22Rv1. The differential gene expression resulted from AR3 or AR knockdown were determined by microarray analysis. The differential expression of a set of 188 genes was consistently detected in both cell lines when AR3 was specifically knocked down while the expression of 412 genes was altered in both cell lines when AR was specifically inhibited (FIG. 5a). Among them, 71 genes are commonly regulated by both AR and AR3. A partial list of these genes is summarized in Table 1. Several known AR target genes such as IGFBP3 and FKBP5 are also regulated by AR3. However, many classical AR target genes such as CLU, TMEPAI, KLK3 (PSA) and CLDN4 were not affected by AR3 knock-down (Table 2). Among the 117 genes that are exclusively regulated by AR3 (Table 3), there are a number of genes, such as MAP4K4, Mdm4, TAF9B, HOXB7 and ELKJ, have been found to be upregulated in hormone refractory or metastatic prostate cancers in previous gene profiling studies on human tissue or xenograft samples (Chen, C. D. et al., Nat Med 10, 33-9 (2004); Best, C. J. et al., Clin Cancer Res 11, 6823-34 (2005); Varambally, S. et al., Cancer Cell 8, 393-406 (2005)). Interestingly, the serine/threonine kinase AKT1, which has been implicated in prostate cancer development and progression, appeared to be regulated by AR3 as well. We further validated the microarray results by the real-time PCR. As shown in FIG. 5b, the level of AKT1 transcript in AR3-knockdown cells is significantly less than that in the cells treated with the control scrambled shRNA or the shRNA specific for AR. The protein level of AKT1 was also reduced accordingly in AR3-knockdown CWR-R1 cells (FIG. 5c). In addition, overexpression of AR3 in an immortalized human normal prostate epithelial cell line HPr-1, which expresses little or no AR3, led to an increase of AKT1 expression while no effect was detected in HPr-1 cells overexpressing AR. We also examined the level of AKT1 protein in the xenograft tumors described in FIG. 4. Consistent with the results in the cell lines, AKT1 protein level is increased in the xenograft tumor of LNCaP overexpressing AR3 and decreased in the xenograft tumor of 22Rv1 with AR3 knock-down (FIG. 5d), suggesting that the level of AKT1 may also be regulated by AR3 in these xenograft tumors and correlated with the tumor growth under androgen-depleted conditions. Furthermore, we identified at least two putative ARE sites in the AKT1 regulatory region and showed that AR3 but not AR was able to bind to these ARE sites determined by the chromatin immunoprecipitation (ChIP) assays (FIG. 5e), suggesting that AR3 may directly regulate AKT1 at the transcriptional level. On the other hand, AR3 failed to bind to the ARE site located at the regulatory region of the PSA gene, a well established AR target gene. Taken together, our data suggest that AR3 and AR may play an overlapping but yet distinct roles in prostate cells by regulating transcription of a subset of common target genes as well as a different set of target genes unique to each receptor. Aberrant expression of AR3 in prostate cancer may contribute to androgen-independence in advanced PCA through regulation of a series of genes functioning in survival, dedifferentiation, chromatin remodeling and transcription specificity (FIG. 6).

TABLE 1

Genes commonly regulated by AR3 and AR

| Gene symbol | Biological process | Change upon knockdown |
|---|---|---|
| STK32B | Cell signaling | up |
| SYT4 | vesicular trafficking and exocytosis | |
| CPA1 | Cell signaling proteolysis, zymogen inhibition | |
| GIPR | secretion of insulin, anabolic response | |
| GPR101 | cell signaling | |
| MAGEA10 | embryonic development, tumor transformation and progression | |
| OTOR | cartilage development and maintenance | |
| ONECUT1 | transcriptional activator, liver gene transcription | |
| IFNA10 | inflammatory response | |
| ZNF624 | Transcriptional regulation | |
| NBN | cellular response to DNA damage | |
| ITTH5 | hyaluronan metabolic process | |
| ZNF624 | transcriptional regulation | |
| DYNLT3 | motor activity | |
| B4GALT4 | cell metabolism | |
| IGFBP3 | growth factor signaling | |
| PNPLA4 | lipid metabolism | |
| PTPRK | regulation of processes involving cell contact and adhesion | |
| ANKRA2 | cell endocytosis | |
| PCDH10 | cell adhesion, mesoderm development | |
| CD19 | B cell receptor signaling pathway | |
| CDH18 | cell adhesion | |
| ZNF589 | DNA binding protein, transcription regulation | down |
| ANGPTL4 | inhibiting vascular activity as well as tumor cell motility and invasiveness | |
| PDXP | coenzyme for biochemical homeostasis | |
| CSRP1 | neuronal development | |
| PPP5C | RNA biogenesis and/or mitosis | |
| TRAF4 | adapter protein and signal transducer | |
| NT5DC3 | lipid metabolism | |
| PPFIA3 | disassembly of focal adhesions | |
| SRF | MAPK signaling pathway | |
| GAS1 | tumor suppressor gene | |
| LDHA | pyruvate metabolism | |
| CHRNA2 | modulation of ion-conducting channels | |
| TMEM81 | transmembrane cell component | |
| SLC25A37 | protein transportation | |
| UBE2M | protein-ubiquitination pathway | |
| DHRS2 | reactive carbonyls metabolism | |
| SNRPB | pre-mRNA splicing or in snRNP structure | |
| TPM1 | striated muscle contraction | |
| SNAP23 | transport vesicle docking and fusion | |
| FKBP5 | protein binding, immunoregulation | |
| PRKAR2A | protein transport | |
| HNRPA0 | pre-mRNA splicing or in snRNP structure | |
| TMED9 | protein transportation and localization | |

TABLE 2

Genes preferentially regulated by AR

| Gene symbol | Biological process | Change upon knockdown |
|---|---|---|
| PCDH11Y | cell-cell recognition | up |
| HOXA13 | transcription factor, involved in embryonic development | |
| CDKN1A | cell cycle progression | |
| PCDH9 | neuronal connections and signal transduction | |
| FAS | apoptosis | |
| MYBL1 | proto-oncogene, transcription activator | |
| TAF9B | DNA-binding, transcription regulation | |
| AR | transcription factor | down |
| CLU | inhibit apoptosis | |
| WNK3 | serine-threonine protein kinase, cell signaling | |
| TCF3 | transcription factor in cell differentiation | |
| IL6ST (gp130) | cytokine signal transduction | |
| TERT | oncogenesis cellular senescence | |
| DACH2 | transcriptional cofactor | |
| TMEPAI | Androgen induced gene | |
| KLK3 | serine proteases, biomarker for prostate cancer | |
| KLK15 | serine proteases, cancer biomarker | |
| CLDN4 | component of cell tight junctions | |
| CDC2 | cell cycle regulation | |
| WNT3 | embryogenesis | |
| WNT10B | Inhibition of adipogenesis | |

TABLE 3

Genes preferentially regulated by AR3

| Gene symbol | Biological process | Change upon knockdown |
|---|---|---|
| EPHA3 | Ephrin receptor, cell signaling | up |
| AF268194 (IRA2) | cell signaling | |
| Neuralin-1 | BMP (bone morphogenetic protein) pathway | |
| OPTN | TNF-alpha signaling pathway | |
| RYR2 | Cardiac muscle ryanodine receptor | |
| SCML2 | transcription repression | |
| RFX3 | transcription factor | |
| AI278811 (MYC like) | transcription factor, proto-oncogene | |
| EFCBP2 | EF-band calcium binding protein 2 | |
| TES | Zinc finger ion binding protein | |
| SLC40A1 | solute carrier, iron-regulated transporter | |
| SLC7A11 | amino acid transport | |
| RGMB | cell membrane lipid-anchor | |
| SYTL2 | vesicle trafficking | |
| APOLD1 | angiogenesis | |
| DMD | actin binding, cytoskeletal anchoring | |
| NTNG1 | neurite outgrowth | |
| GLUD1 | nitrogen metabolism | |
| AKT1 | Proto-oncogene, Serine/threonine-kinase | Down |
| AKT1S1 | Akt-mTOR pathway | |
| WNK1 | Serine/threonine-kinase, signal transduction | |
| MAP4K4 | MAP Kinase Pathways | |
| ADCY6 | signal transduction | |
| PICK1 | organize subcellular localization of membrane proteins | |
| HDAC3 | chromatin modification, epigenetic | |
| SELENBP1 | Golgi protein transport | |
| EVI5 | regulator of cell cycle progression | |
| ELK1 | Ets family transcriptional factor, proto-oncogene | |
| SLC2A4RG | transcription factor | |
| ARFGAP1 | membrane trafficking and vesicle transport | |
| PRG2 | immune response | |
| PLEKHA3 | lipid binding | |
| DNM2 | receptor mediated endocytosis | |
| MDM4 | Proto-oncogene, p53 binding protein | |
| RAP1GAP | GTPase activity, cell signaling | |
| CD2BP2 | mRNP assembly | |
| FXR2 | RNA binding | |
| CUBE1 | adhesive molecule | |
| TPM1 | striated muscle contraction | |
| AP3M1 | vesicles trafficking | |
| KDELR2 | endoplasmic reticulum protein trafficking | |
| RAB6IP1 | Rabb-mediated GTPase signaling | |
| TSR2 | signal transduction | |
| GYS1 | glycogen synthase 1, glucose metabolism | |
| LIMD1 | tumor-suppressor gene | |
| ARNTL2 | circadian rhythms | |
| EMD | nuclear envelope assembling | |
| METTL7A | methyltransferase, chromatin modification | |

TABLE 3-continued

Genes preferentially regulated by AR3

| Gene symbol | Biological process | Change upon knockdown |
|---|---|---|
| HOXB7 | transcription factor, inhibition of differentiation | |
| MDFI | transcription repressor, inhibition of differentiation | |
| TAF9B | DNA binding, transcription regulation | |

Example 2

Cell Culture and Transfection

LNCaP, PC-3, 22Rv1 and COS-i cells were purchased from the American Type Culture Collection. Hormone refractory prostate cancer cell lines C—Si, C4-2, C4-2B and CWR-R1 were kindly provided by Drs. Ming Fong Lin (Igawa, T. et al., Prostate 50, 222-35 (2002)), Donald Tindall, Christopher Gregory and Elizabeth Wilson (Gregory, C. W. et al., Cancer Res 61, 2892-8 (2001)), respectively. LNCaP, PC-3, C-81, C4-2 and C4-2B cells were maintained in RPMI 1640 with 10% FBS. COS-1 cells were grown in DMEM medium with 10% FBS. 22Rv1 and CWR-R1 cells were maintained in RPMI 1640 with 10% heat-inactivated FBS. LAPC-4 cells (kindly provided by Dr. Charles Swayers) were maintained in IMEM supplemented with 15% FBS and 10 nM DHT. The immortalized human normal prostate epithelial cell line HPr-1 described previously (Choo, C. K. et al., Prostate 40, 150-8 (1999)) was kindly provided by Dr. Patrick Ling and maintained in the. SEM keratinocyte medium.

The cells were transfected with FuGENE 6 (Roche) or LipofectAMINE 2000 (Invitrogen) following the manufacturer's instruction.

Example 3

Antibodies

The antibodies used in immunoblot, immunoprecipitation, and immunofluorescence are mouse monoclonal antiAkt1 (2H10) (Cell Signaling), mouse monoclonal anti-AR (441), anti-actin (C2) and rabbit polyclonal anti-AR (H-280) and anti-AR (C-19) (Santa Cruz). The anti-AR3 antibody was developed by immunizing the rabbits with a synthetic peptide corresponding to the C-terminal 16 unique amino acids of AR3 and the terminal bleeds were affinity purified by a commercial carrier.

Example 4

Cloning and Constructs

The primer corresponding to the shARc target sequence (Guo109A, 5'-CAGAGTCGCGACTACTACAACTTTCCA-3') (SEQ ID NO:9) was used to amplify the 3' end of the AR transcripts in CWR-R1 and 22Rv1 cells using the 5'/3'-Rapid Amplification of cDNA Ends (RACE) Kit (Roche Applied Science) according to the manufacturer's instructions. PCRs were carried out using Expand High Fidelity PCR system (Roche Applied Science) which is composed of a unique enzyme mix containing thermostable Taq DNA polymerase and a proofreading polymerase. For the generation of PCR products with high fidelity and specificity, an initial 2-min. denaturation step at 94° C. was followed by 10 cycles of successive incubations at 94° C. (15 s), 65° C. (30 s), and 68° C. (3 min) and 20 cycles of successive incubations at 94° C. (15 s), 65° C. (30 s), and 68° C. (initially 3 min with an increase of 5 s in each successive cycle), and a final 7-min elongation at 72° C. PCR products were electrophoresed on 1% agarose gels and the specific bands/DNA fragments were excised and purified with a Qiagen gel purification kit (Qiagene) according to the manufacturer's instruction. The purified fragments were cloned into the pCR2.1 vector using the PCR TA cloning kit (Invitrogen) and subsequently sequenced (Applied Biosystems sequencer Model 3730). The entire cDNA coding region of the AR isoforms was amplified from cDNA of CWR-R1 or 22Rv1 and first cloned into PCR2.1 vector using a TA cloning kit (Invitrogen). After verification of the sequences, the resulting amplification products were subcloned into a lentivirus expressing vector using BamHI site.

The shRNAs specific for human AR gene in the lentiviral pLKO. 1-puro vector were purchased from Sigma. The sequences of these shRNAs were provided by the manufacture as following:

shARa:
(SEQ ID NO: 10)
CCGGCCTGCTAATCAAGTCACACATCTCGAGATGTGTGACTTGATTAGCA
GGTTTTT;

shARb:
(SEQ ID NO: 11)
CCGGCACCAATGTCAACTCCAGGATCTCGAGATCCTGGAGTTGACATTGG
TGTTTTT;

shARc:
(SEQ ID NO: 12)
CCGGCGCGACTACTACAACTTTCCACTCGAGTGGAAAGTTGTAGTAGTCG
CG UTTT.

The shRNAs specific for AR3 isoform (shAR3) were constructed as described previously (Guo, Z. et al., Cancer Cell 10, 309-19 (2006)). The oligo sequences used were as follows:

shAR3-1 (G622), Guo167a,
(SEQ ID NO: 13)
TGTAATAGTGGTTACCACTCTTCAAGAGAGAGTGGTAACCACTATTACTTTTTTTTC-3',

Guo167b,
(SEQ ID NO: 14)
TCGAGAAAAAAAAGTAATAGTGGTTACCACTCTCTCTTGAAGAGTGGTAACCACTATTACA-3', shAR3-2(G626), Guo171a,
(SEQ ID NO: 15)
5'-TAGGCTAATGAGGTrTATTTCTCAAGAGAAATAAACCTCATTAGCCTTTTTTTTTC-3',

Guo171b,
(SEQ ID NO: 16)
5'-TCGAGAAAAAAAAAGGCTAATGAGGTTTATTTTCCTTGAGAAATAAACCTCATTAGCCTA-3'

-continued shAR3-sc (G627, AR3 scrambled control shRNA sequence): Guo172a,
(SEQ ID NO: 17)
5'-TAAGAAACAGTCCGACTCAATTCAAGAGATTGAGTCGGACTGTTTCTTTCTTTTTTC-3'

Guo172b,
(SEQ ID NO: 18)
5'-TCGAGAAAAAAGAAAGAAACAGTCCGACTCAATCTCTTGAATTGAGTCGGACTGTTTCTTA-3'.

Example 5

Quantitative Real-Time PCR

The primer sequences used for human AKT1 were sense: 5'-TCTATGGCGCTGAGATTGTG-3' (SEQ ID NO:19) and antisense: 5'-CTTAATGTGCCCGTCCTTGT-3' (SEQ ID NO:20). Human Actin sense 5'-GCTATCCAGGCTGTGC-TATC-3' (SEQ ID NO:21) and antisense: 5'-TGTCACG-CACGATTTCC-3' (SEQ ID NO:22). The relative expression levels of Akt1 transcript was quantified by using the comparative $\Delta\Delta C_t$ with Actin as an internal control.

Example 6

Immunofluorescence Microscopy

CWR-R1 and 22Rv1 cells were seeded on the cover slides and allowed to attach to the cover slides for overnight. The cells were then fixed with Lana's fix for 30 min and washed four times with phosphate-buffered saline. The cover slides were blocked in phosphate-buffered saline containing 0.3% Triton-X100, 1% bovine serum albumin, and 1% normal donkey serum 1 hr at room temperature. The newly developed rabbit anti-AR3 antibody was added and incubated for 3 hr at room temperature. After washing with phosphate-buffered saline, the cover slides were incubated with fluorescein isothiocyanatconjugated anti-rabbit secondary antibody for 45 mm at room temperature. Finally, the cells were counterstained with 4',6-diamidino-2-phenylindole (DAPI) to visualize nuclei before mounting. The cover slides were examined by using a Nikon digital microscope system.

Example 7

Immunoprecipitation and Western Blot

The cells were washed twice with ice-cold phosphate-buffered saline and then lysed with lysis buffer (20 mM Tris, pH 7.4, 150 mM NaCl, 1 mM EDTA, 1 mM EGTA, 1% TritonX-100, 2.5 mM sodium pyrophosphate, 1 mM $Na_3VO_4$, 1 µg/ml aprotinin, 1 µg/ml leupeptin, and 1 mM phenylmethylsulfonyl fluoride) at 4° C. for 30 mm. The cell lysates were centrifuged to remove cell debris before incubation with the antibody at 4° C. for 1 hr. The immunocomplexes were collected with protein A-Sepharose beads. The immunoprecipitates were then resuspended in SDS sample buffer and resolved by SDS-polyacrylamide gel electrophoresis. Immunoblotting was performed as described previously (Qiu, Y. et al., Nature 393, 83-5 (1998)).

For the samples from prostate xenograft tumors, the protein lysates were prepared by using the tissue protein extraction reagent (Pierce), and then followed by the same procedures as above. The resulting supernatants of the cell lysates were mixed with SOS sample buffer and resolved by SDS-polyacrylamide gel electrophoresis. Immunoblotting was performed as described. For the prostate tumor samples from mice and patients, the protein lysates were prepared by using the tissue protein extraction reagent (Pierce), and then followed by the same procedures as above.

Example 8

Luciferase Reporter Assay

Luciferase assay was carried out as described previously with minor modifications (Kim, O. et al., Oncogene 23, 1838-44 (2004)). Briefly, cells grown in 24-well plates were transiently transfected with different plasmid constructs using LipofectAM1NE 2000 (Invitrogen) for LNCaP cells and FuGENE HI) (Roche) for COS-1 cells following the manufacturer's instruction. At 24 hr post transfection, the cells were incubated with fresh phenol-red free serum-free medium, or in the experiments with DHT, with phenol-red free medium containing 5% charcoal-stripped FBS, for 24 hr. Dual-Luciferase assays were performed according to the protocol from the manufacturer (Promega). The results are presented as the relative promoter activity that is the changes of luciferase activity relative to the untreated control.

Example 9

Chromatin Immunoprecipitation

CWR-R1 cells were cultured in phenol-red free RPMI 1640 medium containing 5% charcoal-stripped serum for 2 days and then the treatment with vehicle or 10 nM DHT for 1 hr. Cells were cross-linked with 1% formaldehyde and then sonicated, the soluble chromatins were immunoprecipitated as described previously.

The PCR primers were as follows:

```
AKT1 P1 ARE, Q377A,
                                        (SEQ ID NO: 23)
sense 5'-CCACAGAGCACCTCAGCAGTCC-3', antisense Q377B,
                                        (SEQ ID NO: 24)
5'-GAGCAGGGCACCCTCTCATGG-3'

AKT1 P2 ARE Q378A,
                                        (SEQ ID NO: 25)
5'-GCTCCTCACTGACGGACTTGTCTG-3
and Q378B,
                                        (SEQ ID NO: 26)
5'-CCCCTGGTGACAGATGGCC-3'

AKT1 P3 ARE Q380A,
                                        (SEQ ID NO: 33)
5'-GTGCATTTGAGAGAAGCCACGCTG-3'
and Q380B,
                                        (SEQ ID NO: 27)
5'-CACATTGCGCATAGCTGCAGAAG-3'

PSA Enhancer ARE Guo43A,
                                        (SEQ ID NO: 28)
5'-ACAGACCTACTCTGGAGGAAC-3';
and
```

-continued

Guo43B (SEQ ID NO: 29)

5'-AAGACAGCAACACCTTTTT-3'.

Example 10

In vitro cell growth assay and In vivo tumor growth in xenograft models LNCaP, CWR-R1 and 22Rv1 cells were infected with the lentiviruses bearing the shRNA sequences and the AR3 expression constructs as indicated. At 48 hr postinfection, the cells were cultured in phenol red-free RPMI1640 medium containing 5% charcoal-stripped serum for 2 weeks. The cell colonies were visualized by Coomassie Blue staining. The tumor growth of LNCaP, 22Rv1 and CWR-R1 in the xenograft models was carried out as described previously. (Craft, N. et al., Nat Med 5, 280-5 (1999); Long, B. J. et al., Cancer Res 60, 663 0-40 (2000)). Briefly, at 48 hr postinfection, $10^6$ cells were mixed with 100 µl of Matrigel and then subcutaneously (s.c.) injected in the left or right flank of the castrated male SCID/nude mice as indicated in the figure legends. The volumes of the tumors formed on both sides were measured weekly and calculated by using the formula: $0.5236 \times r_1^2 \times r_2$ $(r_1 < r_2)$. The differences in the sizes of the tumors formed on both sides were compared by the paired t-test.

Example 11

Immunohistochemical Analysis

The prostate tissue microarrays used in this study were prepared by NYU Cooperative Prostate Cancer Tissue Resource as described previously. (Guo, Z. et al., Cancer Cell 10, 309-19 (2006)). The Vectastain Elite ABC Kit (Vector Laboratories) was used for immunohistochemical staining. Sections were deparaffinized with xylene and rehydrated through graded alcohol washes followed by antigen retrieval in a water bath at 98° C. for 45 mm in an antigen unmasking solution (Vector Laboratories). Slides were incubated in 0.3% hydrogen peroxide to quench endogenous horseradish peroxidase for 30 min, and then blocked by normal goat serum and subsequently incubated with the anti-AR3 or anti-AR antibody at 4° C. overnight. The slides were then treated with biotin-labeled anti-rabbit IgG and incubated with preformed avidun biotin peroxidase complex. Finally, the sections were counterstained with hematoxylin, dehydrated, mounted and examined. The pair-wise group comparison was conducted by non-parametric Kruskal-Wallis test. Kaplan-Meier analysis was used for testing the association of AR3 staining and PCA recurrence. The statistical analyses were carried out by using SAS version 9.1 software (SAS Institute Inc. Cary, N.C., USA).

Example 12

Microarray Analysis

Total RNA was extracted from CWR-R1 or 22Rv1 cells treated with shAR3-1, shARa and the scrambled shRNA control, respectively. RNA quality and quantity were evaluated using the RNA 6000 Nano kit on Agilent Bioanalyzer (Agilent technologies, Palo Alto, Calif.). For each cell line, mRNA from treated cell line and control, labeled with fluorescent dyes, Cy5 and Cy3 respectively, was reverse-transcribed to cDNA and simultaneously hybridized to an Agilent microarray containing 44k 60mers in the sense orientation. Fluorescent labeling of RNA samples was performed according to standard labeling protocols and kits designed for Agilent Human Whole Genome Expression system (Agilent Technologies, Palo Alto, Calif.). Hybridization was carried out using the conditions specified in the Agilent Human Whole Genome Expression system. Scanned images were processed for quality assessment and preprocessing of image data using the Agilent Feature Extraction software (Agilent Technologies). The software quantifies feature signals and their background, performs dye normalization and calculates feature log ratios and error estimates. The error estimates, based on an extensive error model and pixel level statistics calculated from the feature and background for each spot, are used to generated a p-value for each log ratio. The differential expressed genes were identified by their p-value<0.05 and a minimal 1.4 fold change in both cell lines treated with a given specific shRNA compared to the scrambled control. The changes of some identified genes were validated by the quantitative real-time PCR.

Example 13

Overexpression of AR3 Promotes Proliferation in Prostate Gland

Figure 16:
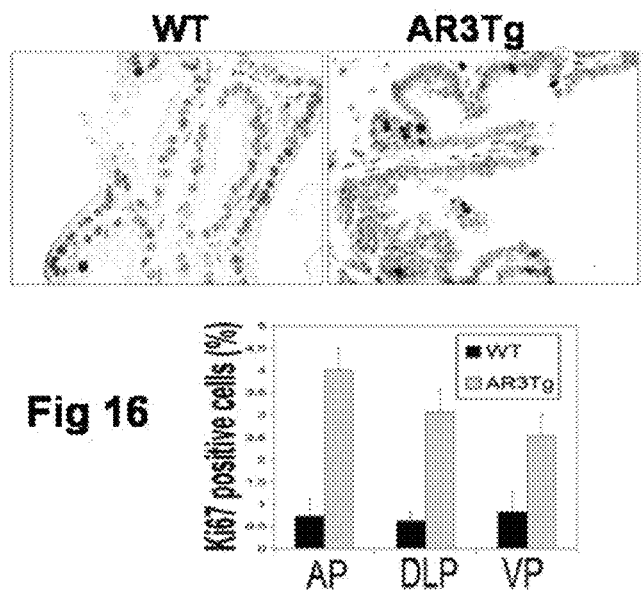
FIG. 16. AR3Tg exhibited an increase in Ki67-positive cells.
Figure 17:
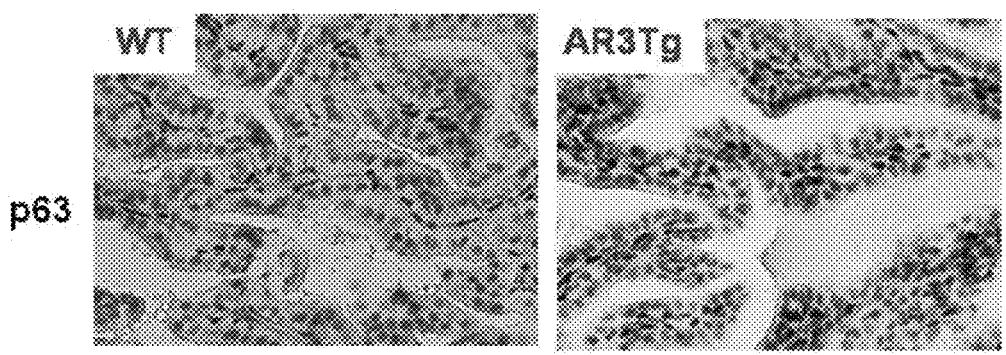
FIG. 17. The number of p63-positive cells is significantly increased in AR3Tg prostates.

To better understand the role of human AR3 in prostate cancer, the AR3 transgenic (AR3Tg) mouse has been established by using the modified probasin promoter ARR2PB which is positively regulated by androgen and expressed in the prostate epithelium of sexually mature mice (FIG. 14A). The genotypes of the offspring were determined by tail snipping and followed by PCR with a pair of primers specific for human AR3 (FIG. 14B). The expression of human AR3 transcript and protein in the transgenic prostate was confirmed by RT-PCR and Western Blot (FIG. 14C). The transgene positive mice and their negative littermates were sacrificed at 2-month old. The prostate gland was dissected and fixed in Formalin. The serial sections of paraffin-embedded tissues were stained with Hematoxylin and Eosin (H & E). Histological analysis of tissue sections revealed that the AR3Tg displayed extensive hyperplasia in all three lobes (FIG. 15), which was accompanied with an increase in Ki67-positive cells (FIG. 16). Interestingly, the number of p63-positive cells is significantly increased in AR3Tg prostates (FIG. 17), suggesting that overexpression of AR3 may promote expansion of basal cells or compromise terminal differentiation of luminal epithelial cell.

Overexpression of AR3 modulates multiple signaling pathways and promotes expansion of Sca-1+ cell population in mouse prostate.

To delineate the mechanisms by which AR3 exerts its biological activity in prostates, we performed gene microarray analysis using Affymatrix Mouse Gene-1.0st-v1 arrays to identify differentially expressed genes in AR3Tg prostates (n=3) in comparison with the age-matched two-month-old WT littermates (n=3). Our initial analysis revealed that 96 genes were down-regulated and 138 genes were up-regulated at least 2-fold (with p<0.05) in AR3Tg. The Ingenuity Pathway analysis suggested that AR3 may be involved in regulation of multiple signaling pathways activated by growth factors. This was supported by the elevated MAPK and Akt pathways in AR3Tg prostate determined by Western blot with anti-phosphoMAPK and pan anti-phospho AKT-substrates antibodies, respectively (FIG. 18). FIG. 19 summarized a partial list of genes regulated by AR3 in mouse prostate. One of the most up-regulated genes is the prohormone convertase Pcskl which was increased 48 fold in addition to some well-established AR target genes such as kallikrein family proteins (Klk1 and Klk1b27) and androgen-binding proteins (Abpb and Abpd). Because Pcskl is known to process pro-TGF-13, we examined the level of mature TGF-β in AR3Tg by Western Blot under reducing conditions using a pan anti-TGF-β antibody. FIG. 20 shows that the level of mature TGF-β monomers (doublet suggesting at least two members of TGF-β family may be processed in prostate) was dramatically elevated in AR3Tg prostate compared to the WT control. As a result, both SMAD1 and SMAD3 phosphorylation is elevated FIG. 20. Klk1 was reported to be able to degrade IGFBP3 (Rajapakse, S. et al., Mol Reprod Dev, 74: 1053-1063, 2007).

Increased Klk1 is expected to free more biological active IGF1 to bind to its receptors. Akt1, previously identified as an AR3 preferred target in human PCA cells, was modestly but significantly elevated in AR3Tg (FIG. 19). Thus, the elevated Akt activity detected in AR3Tg prostate (FIG. 18) may possibly, at least in part, due to increase of free IGF1 level and Akt1 protein level. These changes appear to be consistent with our observation in human PCA cell lines that MAPK, Akt and TGF-β signaling pathways are altered when AR3 is knocked-down (Guo, Z., et al., Cancer Res, 69: 2305-2313, 2009).

Interestingly, two highly related androgen-binding protein genes Abpb (down 100 fold) and Abpd (up 96 fold) located closely on Chromosome 7 were differentially regulated by AR3, suggesting that the effects of AR3 on its target genes are dependent on promoter and/or cell context. Most intriguingly, a modest but significant increase of a set of genes associated with stem/progenitor cells was detected in AR3Tg including Ly6a/Sca-1, Kit, aldehyde dehydrogenase (Aldh1a1), Notch1, Jag1, Frizzled homolog 6 (Fzd6) (FIG. 19). To determine expression of Sca-1 and α6 integrin (CD49f), prostates from 5-week-old AR3Tg or WT littermates were dissected and digested in 0.5% collagenase. The dissociated prostate cells were stained with FITC-anti-Sca-1 and PE-anti-CD49f antibodies. Fluorescence-activated cell sorting (FACS) analysis of double-stained cells was performed on a FACS-Calibur flow cytometer, using vendor-provided CellQuest software. FIG. 21 shows that the number of Sca-1 and a6 integrin double positive cells was increased at least two fold to 35% in AR3Tg prostates compared to 16% in the WT littermate controls, suggesting that the stem/progenitor cell population may expand in AR3Tg prostates. To test whether the AR3 Tg prostate contains more stem/progenitor cells that is capable to generate spheres from a single cell, we further performed prostatic sphere formation in MatriGel as described previously (Xin, L., et al., Stem Cells, 25: 2760-2769, 2007). FIG. 22 shows that the prostatic cells from the AR3Tg appeared to form more spheres than those from the WT littermate controls and AR3 transgene is highly expressed in the basal compartment of the sphere. These data are consistent with our observation in human prostate tissues and suggest that AR3 plays a role in regulating prostate stem/progenitor activity.

Figure 23:
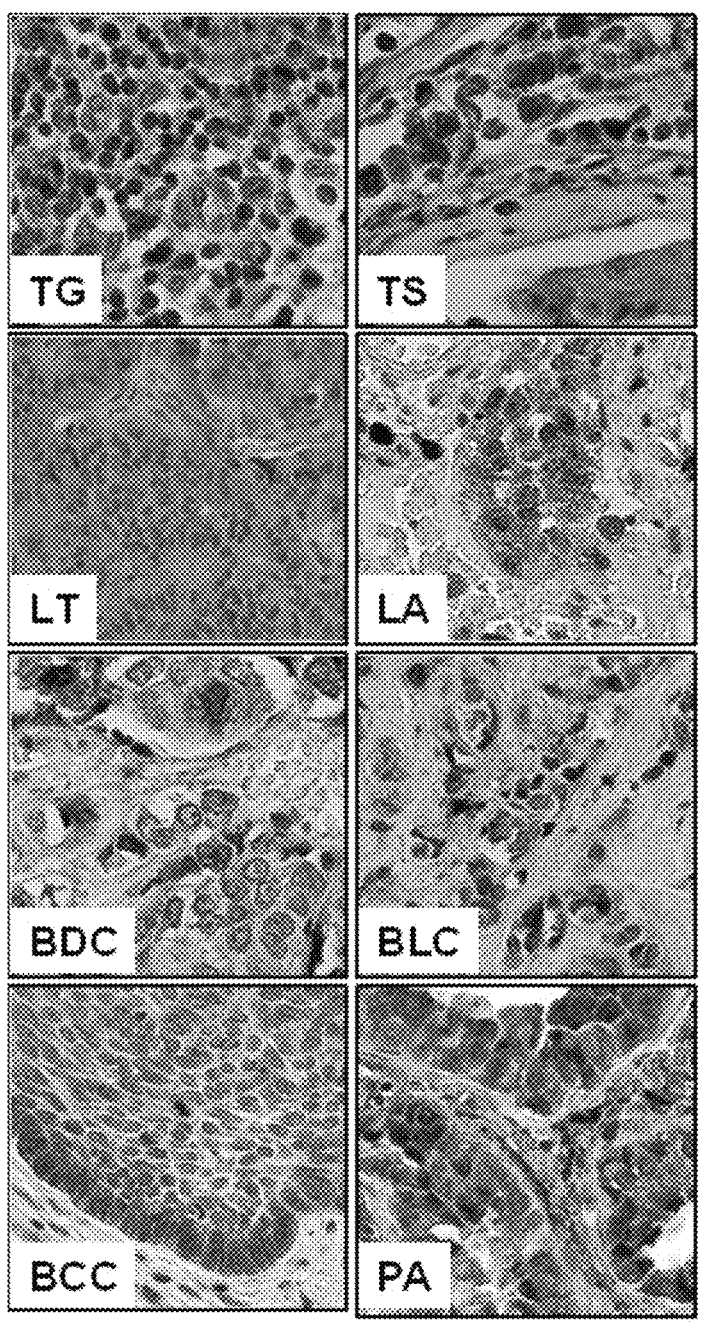
FIG. 23. IHC screening performed on multi-tumor tissues arrays revealed that AR3 appeared to be detected in many types of tumors, including Testis Seminom, Testis Germ cell tumor, Lung Carcinoid tumor, Lung Adenocarcinoma, Breast Ductal Carcinoma, Breast Invasive Lobular Carcinoma, Basal Cell Carcinoma and Pancreas Adenocarcinoma. TS: Testis Seminoma; TG: Testis Germ cell tumor; LT: Lung Carcinoid tumor; LA: Lung Adenocarcinoma; BDC: Breast Ductal Carcinoma; BLC: Breast Invasive Lobular Carcinoma; BCC: Basal Cell Carcinoma; PA: Pancreas Adenocarcinoma.

Our IHC screening performed on multi-tumor tissues arrays revealed that AR3 appeared to be detected in many types of tumors (FIG. 23), including Testis Seminom, Testis Germ cell tumor, Lung Carcinoid tumor, Lung Adenocarcinoma, Breast Ductal Carcinoma, Breast Invasive Lobular Carcinoma, Basal Cell Carcinoma and Pancreas Adenocarcinoma.

Association of AR and AR Splicing Isoforms with Mitochondria

When we overexpressed AR4 in COS-1 cells and performed immunofluorescence staining with anti-AR (N-20), AR4 (green) is primarily detected in punctuate structures in the cytoplasm, which are labeled by the mitotracker (red) (FIG. 24A), suggesting that AR4 may be present in mitochondria instead of nuclei. This possibility is further supported by the fractionation experiments shown in FIG. 24B. It appeared that a portion of AR and AR splicing variants are detected in the mitochondria fraction isolated by using the Mitochondria Isolation kit (Pierce). The detected bands were diminished in cells treated with a cocktail of shRNAs for AR Exon 1 and Exon 5, suggesting that these bands are indeed AR and AR isoforms.

Example 14

Cloning and Characterization of AR8

Figure 25:
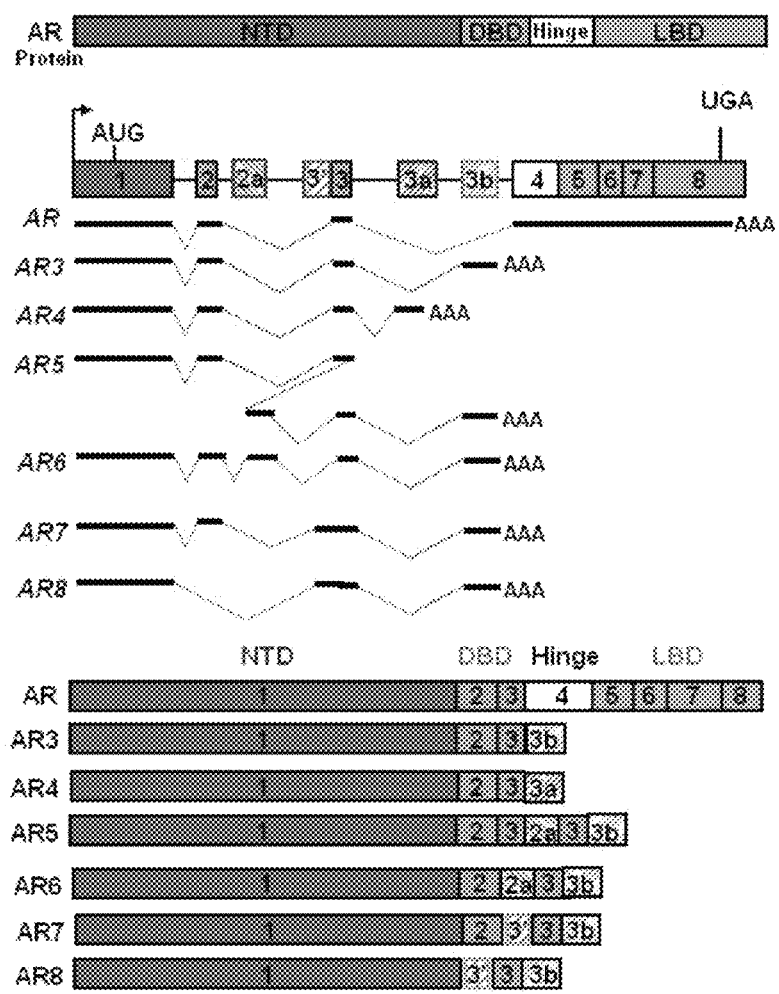
FIGS. 25A-B. Novel AR splicing variant AR8 (FIG. 25A) and its nucleotide sequence is shown in FIG. 25B (SEQ ID NO:4). Schematic structure of the human AR splice variants. The hatched cassettes stand for the cryptic exons. Solid thick lines represent the transcribed exon sequences.
Figure 28:
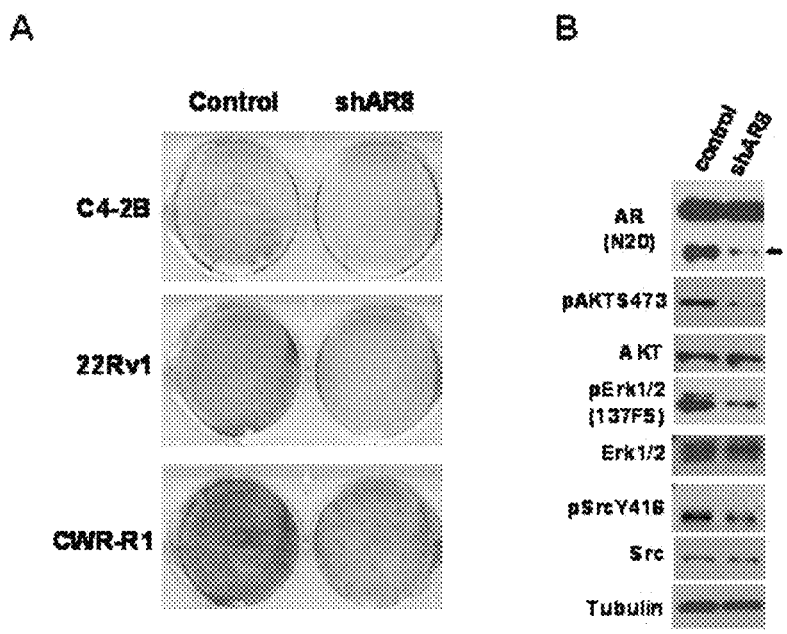
FIGS. 28A-B. Hormone-resistant prostate cancer cell lines C4-2, 22Rv1 and CWR-R1 treated with the lentivirus encoding the shRNA specific for AR8 exhibit attenuated growth (FIG. 28A). This is accompanied with the reduced activity of Akt, MAPK and Src kinases (FIG. 28B). Prostate cancer cells were infected with the lenti-virus encoding shRNA specific for AR8 (shAR8, target sequence: CTCATTATCAGGTC-TATCA (SEQ ID NO:30)). After 2 weeks culture in androgen-depleted condition, the cells were visualized by coomassie blue staining (FIG. 28A). CWR-R1 cells were treated with the control or shAR8 for 48 hrs and cell lysates were subjected to immunoblotting with the indicated antibodies (FIG. 28B). The position of AR8 is marked by an arrow.

We have cloned a novel AR splicing variant AR8 (FIG. 25A) and its nucleotide sequence is shown in FIG. 25B. AR8 contains the NTD and a 33-a.a. unique sequence derived from a cryptic exon 3' located in the Intron 2 (FIGS. 25A & 26A). When we overexpressed AR8 in COS-1 cells and performed immunofluorescence staining with anti-AR (N-20), AR8 is primarily present on the plasma membrane (FIG. 26B). We have identified two Cysteine residues (C558 &569) in the C-terminal unique sequence as potential palmitoylation sites (underlined in FIG. 26A). Substitution of these two Cys with Ala residues dramatically diminished plasma membrane targeting of AR8 (FIG. 26B). The real-time PCR analysis revealed that AR8 expression is elevated in hormone resistant CWR22R xenografts (HR) compared to hormone sensitive counterpart (HS) (FIG. 27A) and AR8 level is also increased in hormone resistant LNCaP derivatives C4-2 and C4-2B compared to hormone sensitive parental LNCaP cells (FIG. 27B). When we treated hormone-resistance prostate cancer cell lines C4-2B, 22Rv1 and CWR-R1 with the lentivirus encoding the shRNA specific for AR8 (target sequence: CTCATTATCAGGTCTATCA) (SEQ ID NO:30), growth of these cells was attenuated (FIG. 28A). This is accompanied with the reduced activity of Akt, MAPK and Src kinases (FIG. 28B). We further examined the effects of AR8 knock-down on cell proliferation and apoptosis as described previously. We were able to show that AR knock-down led to inhibition of proliferation (FIG. 29A) and increase of apoptosis in CWR-R1 cells (FIG. 29B).

What is claimed is:

1. A purified antibody that specifically binds an epitope of the AR8 androgen receptor splice variant polypeptide set forth in SEQ ID NO:8, wherein the epitope is positioned within amino acids 540-573 of SEQ ID NO:8.

2. The antibody of claim 1, wherein the antibody was raised against an antigen comprising amino acids 500-573 of SEQ ID NO:8.

3. The antibody of claim 1, wherein the antibody was raised against an antigen comprising amino acids 540-573 of SEQ ID NO:8.

4. The antibody of claim 1, wherein the antibody is a polyclonal antibody, a monoclonal antibody, a humanized antibody, a human antibody, or a fragment thereof.

* * * * *